US008716320B2

(12) United States Patent
Guiles et al.

(10) Patent No.: US 8,716,320 B2
(45) Date of Patent: May 6, 2014

(54) ANTIBACTERIALL HETEROCYCLIC UREAS

(75) Inventors: Joseph Guiles, Lafayette, CO (US); Thale Jarvis, Boulder, CO (US); Sarah Strong, Louisville, CO (US); Xicheng Sun, Superior, CO (US)

(73) Assignee: Replidyne, Inc., Louisville, CO (US)

( * ) Notice: Subject to any disclaimer, the term of this patent is extended or adjusted under 35 U.S.C. 154(b) by 1320 days.

(21) Appl. No.: 11/880,501

(22) Filed: Jul. 23, 2007

(65) Prior Publication Data
US 2008/0207703 A1 Aug. 28, 2008

Related U.S. Application Data

(60) Provisional application No. 60/820,025, filed on Jul. 21, 2006.

(51) Int. Cl.
| *A61K 31/426* | (2006.01) |
| *A61K 31/427* | (2006.01) |
| *A61K 31/17* | (2006.01) |
| *C07D 277/38* | (2006.01) |
| *C07D 277/48* | (2006.01) |
| *C07C 275/04* | (2006.01) |
| *C07C 275/26* | (2006.01) |

(52) U.S. Cl.
CPC ............ *A61K 31/426* (2013.01); *A61K 31/427* (2013.01); *A61K 31/17* (2013.01); *C07D 277/38* (2013.01); *C07D 277/48* (2013.01); *C07C 275/04* (2013.01); *C07C 275/26* (2013.01)
USPC ........... 514/362; 514/371; 514/588; 548/196; 564/58; 564/59; 564/60

(58) Field of Classification Search
CPC ... A61K 31/426; A61K 31/427; A61K 31/17; C07D 277/38; C07D 277/48; C07C 275/04; C07C 275/26
USPC .......................................... 548/196; 514/371
See application file for complete search history.

(56) References Cited

U.S. PATENT DOCUMENTS

| 4,522,811 | A | 6/1985 | Eppstein et al. .................. 514/2 |
| 6,100,282 | A * | 8/2000 | Alig et al. ...................... 514/371 |
| 6,569,874 | B1 | 5/2003 | Pruitt et al. | |
| 6,863,647 | B2 * | 3/2005 | Pevarello et al. ............. 548/196 |
| 7,105,508 | B1 | 9/2006 | Kling et al. | |
| 2005/0261294 | A1 | 11/2005 | Mjalli et al. | |
| 2007/0155706 | A1 | 7/2007 | Andersch et al. | |
| 2010/0286169 | A1 | 11/2010 | Guiles et al. | |
| 2012/0015941 | A1 | 1/2012 | Guiles et al. | |

FOREIGN PATENT DOCUMENTS

| WO | WO 00/66618 | * 11/2000 |
| WO | WO 01/10847 | 2/2001 |
| WO | WO/2006/071255 | 7/2006 |
| WO | WO 2009/015193 | 1/2009 |
| WO | WO 2009/015208 | 1/2009 |

OTHER PUBLICATIONS

Jacobsen et al., J. Med. Chem. 1999, 42, 1525-1536.*
Zechel et al., Bioorganic & Medicinal Chemistry Letters (2003), 13(2), p. 165-169.*
Lange et al. (2002) Bioorganic & Medicinal Chemistry Letters 12:1379-1382.
Antimicrobial Resistance (1999) General Accounting Office (GAO/RCED-99-132).
S. Berge et al. (1977) Journal of Pharmaceutical Sciences 66(1):1-19.
P. Gould (1986) International J. of Pharmaceutics 33:201-217.
Ochsner et al. (2005) Antimicrobial Agents Chemo. 49:4253-62.
Notice of Allowance mailed Dec. 29, 2011 with respect to U.S. Appl. No. 12/669,634.

* cited by examiner

*Primary Examiner* — Yong Chu
(74) *Attorney, Agent, or Firm* — Swanson & Bratschun L.L.C.

(57) ABSTRACT

The present invention provides novel heterocyclic urea compounds having useful antibacterial activity, pharmaceutical compositions comprising one or more of these compounds, methods of making the same, and methods of using the same.

25 Claims, No Drawings

ANTIBACTERIALL HETEROCYCLIC UREAS

CROSS REFERENCE TO RELATED APPLICATIONS

This application claims the benefit under 35 U.S.C. §119, of U.S. Provisional Patent Application Ser. No. 60/820,025, entitled "Antibacterial Heterocyclic Ureas," filed Jul. 21, 2006, and incorporated by reference herein in its entirety.

TECHNICAL FIELD

Incorporated by reference herein in its entirety is the Sequence Listing entitled "0345_rd_21_us_ST25", created Thursday, Jul. 15, 2010, size of 4.00 kilobytes.

BACKGROUND OF THE INVENTION

Antibacterials kill or inhibit the growth of bacteria by interfering with major processes of cellular function that are essential for survival. The development of antibacterial agents has significantly reduced the morbidity and mortality associated with bacterial infections over the last century, particularly in developed countries. However, the emergence of drug-resistant bacterial strains threatens the resurgence of bacterial-borne diseases long thought to have been conquered.

Resistance to antibacterials can occur when the target of a drug mutates so that it can still function, but is no longer inhibited by the drug (e.g., mutations in the quinolone resistance determining regions of bacterial gyrases and topisomerase enzymes that confer resistance to the fluoroquinolones). In a recent congressional report, the General Accounting Office (GAO) has summarized the current and future public health burden resulting from drug-resistant bacteria (Antimicrobial Resistance (1999). General Accounting Office (GAO/RCED-99-132)). According to this report, the number of patients treated in a hospital setting for an infection with drug-resistant bacteria has doubled from 1994 to 1996 and again almost doubled from 1996 to 1997. The same GAO report also provides clear evidence that previously susceptible bacteria are increasingly becoming resistant and spreading around the world. As a consequence of the increase and prevalence of resistant bacteria there is a growing need to identify new antibacterial agents.

SUMMARY OF THE INVENTION

It has now been found that heterocyclic urea compounds are useful in the treatment of bacterial infections. The present invention relates to antibacterial compounds and salts thereof, pharmaceutical compositions comprising these compounds and methods of use thereof in the treatment of bacterial infections, including resistant bacterial infections.

In one aspect the invention provides compounds of the Formula (I):

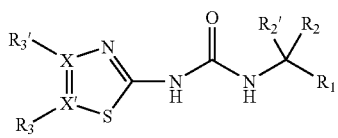

in which $R_1$ is selected from the group consisting of a substituted or unsubstituted aryl, substituted or unsubstituted arylalkyl and substituted or unsubstituted heteroaryl;

$R_2$ and $R_{2'}$ are independently selected from the group consisting of H, substituted or unsubstituted linear, cyclic or branched alkyl, and perfluoroalkyl;

X and X' are independently selected from the group consisting of a C and N atom;

$R_3$ and $R_{3'}$ are independently selected from the group consisting of null, H, halogen, and

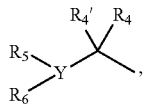

wherein either of $R_3$ or $R_{3'}$ but not both is

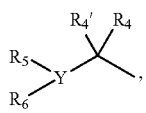

and wherein $R_3$ or $R_{3'}$ is null when X or X', respectively, is N;

Y is independently selected from the group consisting of a CH, C, O, S and N atom;

$R_4$ and $R_{4'}$ are independently selected from the group consisting of H, substituted or unsubstituted linear, cyclic or branched alkyl, perfluoroalkyl and O when taken together; and $R_5$ and $R_6$ are independently selected from the group consisting of null, H, OH, O, substituted or unsubstituted O-alkyl, substituted or unsubstituted aryl, substituted or unsubstituted arylalkyl, substituted or unsubstituted linear, cyclic or branched alkyl, and perfluoroalkyl, wherein when Y is O or S, $R_6$ is null, and wherein when Y is C, either $R_5$ or $R_6$ must be O, and further wherein when Y is N or CH, $R_5$ and $R_6$ together can form a 4, 5, or 6 member saturated ring comprising carbon atoms or at least one carbon atom and one or more heteroatoms selected from O and $NR_7$, and wherein $R_7$ is selected from the group consisting of H, substituted or unsubstituted $C_{(1-6)}$alkyl, substituted or unsubstituted $C_{(1-6)}$acyl, substituted or unsubstituted aryl, substituted or unsubstituted heteroaryl, and wherein $R_5$, $R_6$, and $NR_7$ together can form a 4,4-, 4,5-, 5,5-, 5,6-, or 6,6-saturated bicyclic ring system comprising carbon atoms or at least one carbon atom and one or more heteroatoms selected from O and N.

These and various other features as well as advantages which characterize the invention will be apparent from a reading of the following detailed description and a review of the appended claims.

DETAILED DESCRIPTION OF THE INVENTION

The present invention relates to antibacterial compounds and salts thereof, pharmaceutical compositions comprising these compounds and methods of use thereof. The compounds of the present invention are useful in the protection of patients from bacterial infections, including antibiotic resistant bacterial infections.

Compounds of the invention include novel heterocyclic urea compounds. In one embodiment, the invention provides compounds of Formula (I):

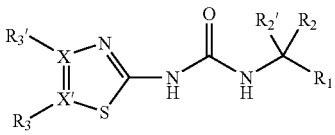

(I)

in which $R_1$ is preferably a substituted or unsubstituted phenyl group or thiophene group, for example, a phenyl group which has one or more substituents independently selected from halogen, cyano, $(C_{1-6})$alkyl, mono to perfluoro$(C_{1-3})$alkyl, $(C_{3-7})$cycloalkyl, $(C_{2-6})$alkenyl, $(C_{1-6})$alkoxy, $(C_{2-6})$alkenoxy, hydroxy, amino, mono- or di-$(C_{1-6})$alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$alkyl, carboxy$(C_{1-6})$alkyl, $(C_{1-6})$alkylcarbonyloxy, carboxy$(C_{1-6})$alkyloxy, $(C_{1-6})$alkoxycarbonyl$(C_{1-6})$alkoxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl, carbamoyl. Suitable identities for $R_1$ include, but are not limited to 3-fluorophenyl, 4-fluorophenyl, 3-chlorophenyl, 4-chlorophenyl, 3-bromophenyl, 4-bromophenyl, 3-iodophenyl, 4-iodophenyl, 3-methoxyphenyl, 4-methoxyphenyl, 3-methylphenyl, 4-methylphenyl, 3-trifluoromethylphenyl, 4-trifluoromethylphenyl, 3,4-methylendioxyphenyl, 3,4-difluorophenyl, 3,4-dichlorophenyl, 3,4-dibromophenyl, 3,4-dimethylphenyl, 3,4-(-$CH_2CH_2CH_2$-)phenyl, 3,4-(-$OCH_2CH_2O$-)phenyl, 3-chloro-4-fluorophenyl, benzo[1,3]dioxyl-5-yl, 3-cyanophenyl, thiophen-2-yl, thiophen-3-yl, 4,5-di-bromo-thiophen-2-yl, 5-chloro-thiophen-2-yl, and 5-bromo-thiophen-2-yl.

X and X' are independently selected from C or N atom. Preferred identities for X and X' include both being C forming a thiazole ring, include wherein X is N and X' is C forming a 3,4-thiadiazole and wherein X is C and X' is N forming a 3,5-thiadiazole ring.

Y is independently a CH, C, O, S or N atom. Preferred identities include wherein Y is C forming an alkyl, wherein Y is O forming an ether, wherein Y is S forming a thioether, and wherein Y is N forming an amine.

$R_2$ and $R_{2'}$ are independently selected from the group consisting of H, substituted or unsubstituted linear, cyclic or branched alkyl, or perfluoroalkyl. Preferred identities for $R_2$ and $R_{2'}$ include H, and $C_{(1-6)}$alkyl.

$R_3$ and $R_{3'}$ are independently selected from the group consisting of null, H, halogen, and

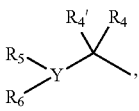

wherein either of $R_3$ or $R_{3'}$ but not both is

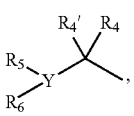

and wherein $R_3$ or $R_{3'}$ is null when X or X', respectively, is N. Preferred identities for $R_3$ and $R_{3'}$ include null, H, Br, Cl, and F, and

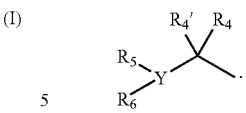

$R_4$ and $R_{4'}$ are independently selected from the group consisting of H, O, substituted or unsubstituted linear, cyclic or branched alkyl, or perfluoroalkyl. Preferred identities for $R_4$ and $R_{4'}$ include H, $C_{(1-6)}$alkyl, and O for both $R_4$ and $R_{4'}$ to form a carbonyl.

$R_5$ and $R_6$ are independently selected from the group consisting of H, O, OH, substituted or unsubstituted aryl, substituted or unsubstituted arylalkyl, substituted or unsubstituted linear, cyclic or branched alkyl, or perfluoroalkyl. When Y is O or S, $R_6$ is null. When Y is C, $R_5$ or $R_6$ must be O. When Y is N or CH, $R_5$ and $R_6$ together can form a 4, 5, or 6 membered saturated ring comprising carbon atoms or comprising at least one carbon atom and one or more heteroatoms selected from O and $NR_7$, wherein $R_7$ is a hydrogen or substituted or unsubstituted $C_{(1-6)}$alkyl, substituted or unsubstituted $C_{(1-6)}$acyl, substituted or unsubstituted aryl, substituted or unsubstituted heteroaryl, or $R_5$, $R_6$, and $R_7$ can together form a 4,4-, 4,5-, 5,5-, 5,6-, or 6,6-saturated bicyclic ring system comprising carbon atoms or comprising at least one carbon atom and one or more heteroatoms selected from O and N.

Preferred identities for $R_5$ and $R_6$ are hydrogen, methyl, ethyl, hydroxyl, methoxy, carboxymethyl, hydroxymethyl, 2-methoxyethyl, butyl, phenoxyethyl, 3-methoxypropyl, 2-ethoxyethyl, 2-(dimethylamino)-ethyl, methylthioethyl, 2-(methylsulfone)ethyl, 2-(methylsulfoxyl)ethyl, 2-tert-Butoxy-ethyl, 2-hydroxyethyl, phenyl, 2-(tert-butyl carbamate)-ethyl, 2-aminoethyl, 2-(morpholin-4-yl)-ethyl, 2-(acetamide)-ethyl, 2-(2-methoxyethoxy)ethyl, 2-(4-methyl-piperazin-1-yl)-ethyl, 2-(imidazol-1-yl)-ethyl, 2-(2-(2-methoxyethoxy)ethoxy)ethyl, 2-(1-methyl-1H-imidazol-2-ylsulfanyl)-ethyl, 2-(4-methyl-thiazol-5-yl)-ethyl, allyl, 2,3-dihydroxypropyl, 3-pyridin-2-yl-propyl, 2-pyridin-3-yl-ethyl, octahydro-quinolizin-1-ylmethyl, 2-pyrrolidin-1-yl-ethyl, 1-methyl-piperidin-4-yl, 2-(2-oxooxazolidin-3-yl)ethyl, 2-(methylsulfonamido)ethyl, 3-methylcarboxylate-pyrazin-2-yl, 4-formyl-piperazin-1-ylmethyl, 3-methylpyrazin-2-yl, ethyl-phosphoramidic acid diethyl ester, 2-(carbamic acid methyl ester)ethyl, 2-(3-ethyl-ureido)-ethyl, acetic acid tert-butyl ester, acetic acid, 2-diethylamino-ethyl, 3-dimethylamino-propyl, 1,1-dioxo-tetrahydro-1-lambda$^6$-thiophen-3-yl, 4-hydroxy-1,1-dioxo-tetrahydro-1-lambda$^6$-thiophen-3-yl, N-(1,1-dioxo-tetrahydro-1lambda$^6$-thiophen-3-yl)-acetamide-, o-tolyl, pyridin-2-yl, 3,5-dimethylisoxazol-4-yl-methyl, 2,4-dimethoxy-benzyl, 3-(hydroxymethyl)-5-methylisoxazol-4-yl)methyl, 2,3,4-trimethoxy-benzyl, 4-methoxyphenyl, 4-Fluoro-phenyl, 4-acetamido-phenyl, 3,4-dimethoxy-phenyl, 2-(pyrazin-2-yl)ethyl, 4-methyl-4H-1,2,4-triazol-3-yl, 1,3,4-thiadiazol-2-yl, thiazol-2-yl, 1-methyl-1H-tetrazol-5-yl, 4,5-dimethyl-4H-1,2,4-triazol-3-yl.

Preferred identifies for $R_5$ and $R_6$ together, and/or $R_5$, $R_6$, and $NR_7$ together include 4-formyl-piperazin-1-yl, 4-methylpiperazin-1-yl, 4-ethylpiperazin-1-yl, 4-phenylpiperazin-1-yl, 4-pyrimidin-2-yl-piperazin-1-yl, 4-(hexahydro-pyrrolo[1,2-a]imidazol-1-yl, morpholin-4-yl, 4-hydroxy-isoxazolidin-2-yl, 1,1-dioxo-1-lamda$^6$-thiomorpholin-4-yl.

When used herein, the term "alkyl" and similar terms such as "alkoxy" include all straight chain, branched, and cyclic isomers. Representative examples thereof include methyl, ethyl, n-propyl, iso-propyl, cyclobutyl, cyclopropyl, cyclopentyl, cyclohexyl, n-butyl, sec-butyl, iso-butyl, t-butyl, n-pentyl and n-hexyl. Optionally fluorosubstituted alkyls may have 1 or more substitutions of F for H on the alkyl chain. A representative example of an optionally fluorosubstituted alkyl is trifluoromethyl.

When used herein, the terms "alkenyl" and "alkynyl" include all straight chain, branched and cyclic isomers. Representative examples thereof include vinyl, ethynyl and 1-propynyl. Optionally fluorosubstituted alkenyls may have 1 or more substitutions of F for H on the alkenyl chain. A representative example of an optionally fluorosubstituted alkenyl is fluorovinyl.

Preferred substituents for alkyl and alkenyl groups include, for example, and unless otherwise defined, halogen, cyano, azido, nitro, carboxy, $(C_{1-6})$alkoxycarbonyl, carbamoyl, mono- or di-$(C_{1-6})$alkylcarbamoyl, sulpho, sulphamoyl, mono- or di-$(C_{1-6})$alkylsulphamoyl, amino, mono- or di-$(C_{1-6})$alkylamino, acylamino (e.g., pyridyloxy), ureido, $(C_{1-6})$alkoxycarbonylamino, 2,2,2-trichloroethoxycarbonylamino, aryl, heteroaryl, heterocyclyl, hydroxy, $(C_{1-6})$alkoxy (e.g., ethoxy, isopropoxy), acyloxy (e.g., phenyloxy, benzyloxy, phenethoxy), oxo, acyl, 2-thienoyl, $(C_{1-6})$alkylthio, $(C_{1-6})$alkylsulphinyl, $(C_{1-6})$alkylsulphonyl, hydroxyimino, $(C_{1-6})$alkoxyimino, hydrazino, hydrazono, benzohydroximoyl, guanidino, amidino and iminoalkylamino. Also preferred are 4-formyl-piperazin-1-yl, 4-methylpiperazin-1-yl-, 4-ethylpiperazin-1-yl-, 4-phenylpiperazin-1-yl-, 4-pyrimidin-2-yl-piperazin-1-yl, Hexahydroxy-pyrrolo[1,2-a]imidazole-1-yl, Morpholin-4-yl, 3-(2-methoxy-ethyl)-methyl-amino, and 3-(2-methoxy-ethyl)-methyl-amino. Other appropriate substituents include alkylthio meaning an alkyl-S— group in which the alkyl group is as previously described. Non-limiting examples of suitable alkylthio groups include methylthio and ethylthio. The bond to the parent moiety is through the sulfur. Substituents further include alkoxycarbonyl meaning an alkyl-O—CO— group. Non-limiting examples of suitable alkoxycarbonyl groups include methoxycarbonyl and ethoxycarbonyl. The bond to the parent moiety is through the carbonyl. Another suitable substituent is alkylsulfonyl meaning an alkyl-$SO_2$ group. Preferred alkylsulfonyl groups are those in which the alkyl group is a lower alkyl. The bond to the parent moiety is through the sulfonyl.

When used herein, the term "aryl" means an aromatic monocyclic or multicyclic ring system with each ring comprising from about 6 to about 14 carbon atoms, preferably about 6 to about 10 carbon atoms. The aryl group can be optionally substituted with one or more "ring system substituents" and optionally substituted with up to five, preferably up to three substituents which may be the same or different, and are as defined herein. Non-limiting examples of suitable aryl groups include phenyl, naphthyl, anthracenyl, phenanthrenyl, indanyl, indenyl, and the like. Aryl moieties are well known and described, for example, in Hawley's Condensed Chemical Dictionary (13 ed.), R. J. Lewis, ed., J. Wiley & Sons, Inc., New York (1997). Aryl groups can be substituted or unsubstituted.

When substituted, an aryl group may have up to three substituents. Preferred substituents for an aryl group (a "ring system substituent") include, for example, and unless otherwise defined, halogen, cyano, $(C_{1-6})$alkyl, mono to perfluoro $(C_{1-3})$alkyl, $(C_{3-7})$cycloalkyl, $(C_{2-6})$alkenyl, $(C_{1-6})$alkoxy, $(C_{2-6})$alkenoxy, aryl$C_{(1-6)}$alkoxy, halo$(C_{1-6})$alkyl, hydroxy, amino, mono- or di-$(C_{1-6})$alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$alkyl, carboxy$(C_{1-6})$alkyl, $(C_{1-6})$alkylcarbonyloxy, carboxy$(C_{1-6})$alkyloxy, $(C_{1-6})$alkoxycarbonyl$(C_{1-6})$alkoxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl, heteroaryl and heterocyclyl. Other preferred aryl groups include arylalkyl meaning an alkyl substituted aryl group. Other preferred aryl groups include aryloxy meaning an aryl-O— group in which the aryl group is as previously described. Non-limiting examples of suitable aryloxy groups include phenoxy and naphthoxy. The bond to the parent moiety is through the ether oxygen. Arylalkyloxy meaning an arylalkyl-O— group in which the arylalkyl group is as previously described. Non-limiting examples of suitable arylalkyloxy groups include benzyloxy and phenethyloxy. The bond to the parent moiety is through the ether oxygen. Another preferred aryl is an arylthio meaning an aryl-S— group in which the aryl group is as previously described. Non-limiting examples of suitable arylthio groups include phenylthio and naphthylthio. The bond to the parent moiety is through the sulfur. Other preferred aryls include arylalkylthio meaning an arylalkyl-S— group in which the arylalkyl group is as previously described. Non-limiting example of a suitable arylalkylthio group is benzylthio. The bond to the parent moiety is through the sulfur. Other preferred aryls is an aryloxycarbonyl meaning an aryl-O—C(O)— group. Non-limiting examples of suitable aryloxycarbonyl groups include phenoxycarbonyl and naphthoxycarbonyl. The bond to the parent moiety is through the carbonyl. Another such group is an arylalkoxycarbonyl meaning an arylalkyl-O—C(O)— group. Non-limiting example of a suitable aralkoxycarbonyl group is benzyloxycarbonyl. The bond to the parent moiety is through the carbonyl. Yet another such group is an arylsulfonyl meaning an aryl-$SO_2$— group. The bond to the parent moiety is through the sulfonyl.

When used herein, the term "heteroaryl" monocyclic and polycyclic aromatic hydrocarbons include at least one heteroatom ring member such as sulfur, oxygen, or nitrogen alone or in combination. Preferably the heteroaryl ring comprises from 4 to 7, and preferably 5 to 6, ring atoms. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-S-oxide, 2,3-dihydrobenzothienyl-5-dioxide, benzoxazolin-2-on-yl, indolinyl, benzodioxolanyl, benzodioxane, and the like. Heteroaryl groups can be substituted or unsubstituted. A fused heteroaryl ring system may include carbocyclic rings and need only include one heterocyclic ring.

When used herein, the term "heterocyclyl" means an aromatic or non-aromatic saturated monocyclic or multicyclic (preferably bicyclic) ring system comprising about 3 to about 10 ring atoms, preferably about 5 to about 10 ring atoms, in which one or more of the atoms in the ring system is an element other than carbon, for example nitrogen, oxygen or sulfur, alone or in combination. Suitably the heterocyclic ring comprises from 4 to 7, preferably 5 to 6, ring atoms. A fused heterocyclic ring system may include carbocyclic rings and need only include one heterocyclic ring. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, pyrimidyl, oxazolidinyl, and the like.

When substituted, a heteroaryl or a heterocyclyl group may have up to three substituents. Preferred such substituents include those previously mentioned for an aryl group as well as oxo.

When used herein, the terms "halogen" and "halo" include fluorine, chlorine, bromine and iodine and fluoro, chloro, bromo and iodo, respectively.

When used herein, the term "acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

When used herein, the term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent. The term "optionally substituted" means optional substitution with the specified groups, radicals or moieties.

It should also be noted that any heteroatom with unsatisfied valences in the text, schemes, examples and Tables herein is assumed to have the hydrogen atom to satisfy the valences. When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, N.Y.

When any variable (e.g., aryl, heterocycle, $R_2$, etc.) occurs more than one time in any constituent or in Formula (I), its definition on each occurrence is independent of its definition at every other occurrence.

When used herein, the term "composition" is intended to encompass a product comprising the specified ingredients in the specified amounts, as well as any product which results, directly or indirectly, from combination of the specified ingredients in the specified amounts.

The compounds according to the invention are suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

It will be appreciated that certain compounds of the present invention may comprise one or more chiral centers so that compounds may exist as stereoisomers, including diastereoisomers and enantiomers. The present invention covers all such stereoisomers, and mixtures thereof, including racemates.

Accordingly, the invention provides the following preferred compounds:

1-(3,4-dichlorobenzyl)-3-(4-(methoxymethyl)thiazol-2-yl) urea;
1-(3,4-dichlorobenzyl)-3-(4-((2-methoxyethoxy)methyl) thiazol-2-yl)urea;
1-(3,4-dichlorobenzyl)-3-(4-(butoxymethyl)thiazol-2-yl) urea;
1-(3,4-dichlorobenzyl)-3-(4-((2-phenoxyethoxy)methyl) thiazol-2-yl)urea;
1-(3,4-dichlorobenzyl)-3-(4-((3-methoxypropoxy)methyl) thiazol-2-yl)urea;
1-(3,4-dichlorobenzyl)-3-(4-((2-ethoxyethoxy)methyl)thiazol-2-yl)urea;
1-(3,4-dichlorobenzyl)-3-(4-((2-(dimethylamino)ethoxy) methyl)thiazol-2-yl)urea;
1-(3,4-dichlorobenzyl)-3-(4-((2-(methylthio)ethoxy)methyl)thiazol-2-yl)urea;
1-(3,4-dichloro-benzyl)-3-[4-(2-methanesulfinyl-ethoxymethyl)-thiazol-2-yl]-urea;
1-(3,4-dichlorobenzyl)-3-(4-((2-(methylsulfonyl)ethoxy) methyl)thiazol-2-yl)urea;
1-(3-fluoro-benzyl)-3-[4-(2-methoxy-ethoxymethyl)-thiazol-2-yl]-urea;
1-[4-(2-tert-butoxy-ethoxymethyl)-thiazol-2-yl]-3-(3,4-dichloro-benzyl)-urea;
1-(3,4-dichloro-benzyl)-3-[4-(2-hydroxy-ethoxymethyl)-thiazol-2-yl]-urea;
1-(3,4-dichloro-benzyl)-3-(4-phenoxymethyl-thiazol-2-yl)-urea;
1-(3-fluoro-benzyl)-3-[4-(2-methanesulfonyl-ethoxymethyl)-thiazol-2-yl]-urea;
5-{2-[3-(3,4-dichloro-benzyl)-ureido]-thiazol-4-yl}-pyrrolidin-3-yl ester;
Ethyl 2-(2-(3-(3,4-dichlorobenzyl)ureido)thiazol-4-yl)acetate;
1-(3,4-dichlorobenzyl)-3-(4-(2-hydroxyethyl)thiazol-2-yl) urea;
1-(3-fluorobenzyl)-3-(4-(2-hydroxyethyl)thiazol-2-yl)urea;
Ethyl 2-(3-(3,4-dichlorobenzyl)ureido)thiazole-4-carboxylate;
1-(3,4-dichlorobenzyl)-3-(4-(hydroxymethyl)thiazol-2-yl) urea;
1-(3-bromo-benzyl)-3-(4-{[(2-methoxy-ethyl)-methyl-amino]-methyl}-thiazol-2-yl)-urea;
1-(3-chloro-benzyl)-3-(4-{[(2-methoxy-ethyl)-methyl-amino]-methyl}-thiazol-2-yl)-urea;
1-(3-fluoro-benzyl)-3-(4-{[(2-methoxy-ethyl)-methyl-amino]-methyl}-thiazol-2-yl)-urea;
1-(3-chloro-4-fluoro-benzyl)-3-(4-{[(2-methoxy-ethyl)-methyl-amino]-methyl}-thiazol-2-yl)-urea;
1-(3,4-dimethyl-benzyl)-3-[4-(2-methoxy-ethoxymethyl)-thiazol-2-yl]-urea;

1-(3-bromo-benzyl)-3-[4-(2-methoxy-ethoxymethyl)-thiazol-2-yl]-urea;
1-(4-chloro-3-trifluoromethyl-benzyl)-3-[4-(2-methoxy-ethoxymethyl)-thiazol-2-yl]-urea;
1-benzo[1,3]dioxol-5-ylmethyl-3-[4-(2-methoxy-ethoxymethyl)-thiazol-2-yl]-urea;
1-(3-chloro-4-fluoro-benzyl)-3-[4-(2-methoxy-ethoxymethyl)-thiazol-2-yl]-urea;
1-(3-chloro-benzyl)-3-[4-(2-methoxy-ethoxymethyl)-thiazol-2-yl]-urea;
1-(3-iodo-benzyl)-3-[4-(2-methoxy-ethoxymethyl)-thiazol-2-yl]-urea;
1-(4-bromobenzyl)-3-(4-((2-methoxyethoxy)methyl)thiazol-2-yl)urea;
1-(1-(4-bromophenyl)ethyl)-3-(4-((2-methoxyethoxy)methyl)thiazol-2-yl)urea;
1-(4-chloro-3-fluoro-benzyl)-3-[4-(2-methoxy-ethoxymethyl)-thiazol-2-yl]-urea;
1-(3-bromo-4-chloro-benzyl)-3-[4-(2-methoxy-ethoxymethyl)-thiazol-2-yl]-urea;
1-(3,5-difluoro-benzyl)-3-[4-(2-methoxy-ethoxymethyl)-thiazol-2-yl]-urea;
1-[4-(2-methoxy-ethoxymethyl)-thiazol-2-yl]-3-(3,4,5-trifluoro-benzyl)-urea;
1-(4,5-dibromo-thiophen-2-ylmethyl)-3-[4-(2-methoxy-ethoxymethyl)-thiazol-2-yl]-urea;
1-(2,2-difluoro-benzo[1,3]dioxol-5-ylmethyl)-3-[4-(2-methoxy-ethoxymethyl)-thiazol-2-yl]-urea;
1-(3-chloro-5-fluoro-benzyl)-3-[4-(2-methoxy-ethoxymethyl)-thiazol-2-yl]-urea;
1-[4-(2-methoxy-ethoxymethyl)-thiazol-2-yl]-3-thiophen-3-ylmethyl-urea;
1-[4-(2-methoxy-ethoxymethyl)-thiazol-2-yl]-3-thiophen-2-ylmethyl-urea;
1-(5-bromo-thiophen-2-ylmethyl)-3-[4-(2-methoxy-ethoxymethyl)-thiazol-2-yl]-urea;
1-(5-chloro-thiophen-2-ylmethyl)-3-[4-(2-methoxy-ethoxymethyl)-thiazol-2-yl]-urea;
1-(4-fluoro-benzyl)-3-[4-(2-methoxy-ethoxymethyl)-thiazol-2-yl]-urea;
1-(3-chloro-benzyl)-3-[4-(2-methanesulfonyl-ethoxymethyl)-thiazol-2-yl]-urea;
1-(3-bromo-benzyl)-3-[4-(2-methanesulfonyl-ethoxymethyl)-thiazol-2-yl]-urea;
tert-butyl 2-((2-(3-(3,4-dichlorobenzyl)ureido)thiazol-4-yl)methoxy)-ethylcarbamate;
1-(3,4-dichlorobenzyl)-3-(4-((2-aminoethoxy)methyl)thiazol-2-yl)urea;
1-(3,4-dichloro-benzyl)-3-[4-(2-morpholin-4-yl-ethoxymethyl)-thiazol-2-yl]-urea;
N-(2-{2-[3-(3,4-dichloro-benzyl)-ureido]-thiazol-4-ylmethoxy}-ethyl)-acetamide;
1-(benzo[d][1,3]dioxol-5-ylmethyl)-3-(4-((2-(methylthio)ethoxy)methyl)thiazol-2-yl)urea;
1-(benzo[d][1,3]dioxol-5-ylmethyl)-3-(4-((2-(methylsulfoxyl)ethoxy)methyl)thiazol-2-yl)urea;
1-(benzo[d][1,3]dioxol-5-ylmethyl)-3-(4-((2-(methylsulfone)ethoxy)methyl)thiazol-2-yl)urea;
1-(3,4-dichlorobenzyl)-3-(4-((2-(2-methoxyethoxy)ethoxy)methyl)thiazol-2-yl)urea;
1-(3,4-dichlorobenzyl)-3-(4-((2-(4-methylpiperazin-1-yl)ethoxy)methyl)thiazol-2-yl)urea;
1-(3,4-dichloro-benzyl)-3-[4-(2-imidazol-1-yl-ethoxymethyl)-thiazol-2-yl]-urea;
1-(3,4-dichlorobenzyl)-3-(4-((2-(2-(2-methoxyethoxy)ethoxy)methyl)thiazol-2-yl)urea;
1-(3,4-dichloro-benzyl)-3-{4-[2-(1-methyl-1H-imidazol-2-ylsulfanyl)-ethoxymethyl]-thiazol-2-yl}-urea;
1-(3,4-dichloro-benzyl)-3-{4-[2-(4-methyl-thiazol-5-yl)-ethoxymethyl]-thiazol-2-yl}-urea;
1-(3,4-dichlorobenzyl)-3-(4-(allyloxymethyl)thiazol-2-yl)urea;
1-(3,4-dichlorobenzyl)-3-(4-((2,3-dihydroxypropoxy)methyl)thiazol-2-yl)urea;
1-(3,4-dichloro-benzyl)-3-[4-(3-pyridin-2-yl-propoxymethyl)-thiazol-2-yl]-urea;
1-(3,4-dichloro-benzyl)-3-[4-(2-pyridin-3-yl-ethoxymethyl)-thiazol-2-yl]-urea;
1-(3,4-dichloro-benzyl)-3-[4-(octahydro-quinolizin-1-yl-methoxymethyl)-thiazol-2-yl]-urea;
1-(3,4-dichlorobenzyl)-3-(4-((2-(pyrrolidin-1-yl)ethoxy)methyl)thiazol-2-yl)urea;
1-(3,4-dichloro-benzyl)-3-[4-(1-methyl-piperidin-4-yloxymethyl)-thiazol-2-yl]-urea;
1-(3,4-dichlorobenzyl)-3-(4-((2-(2-oxooxazolidin-3-yl)ethoxy)methyl)thiazol-2-yl)urea;
1-(3,4-dichlorobenzyl)-3-(4-((2-(methylsulfonamido)ethoxy)methyl)thiazol-2-yl)urea;
methyl 3-((2-(3-(3-fluorobenzyl)ureido)thiazol-4-yl)methoxy)pyrazine-2-carboxylate;
1-(3-fluorobenzyl)-3-(4-((3-methylpyrazin-2-yloxy)methyl)thiazol-2-yl)urea;
1-(3,4-dichloro-benzyl)-3-[4-(4-formyl-piperazin-1-ylmethyl)-thiazol-2-yl]-urea;
[2-({2-[3-(3,4-dichloro-benzyl)-ureido]-thiazol-4-ylmethyl}-methyl-amino)-ethyl]-carbamic acid tert-butyl ester;
1-(4-{[(2-amino-ethyl)-methyl-amino]-methyl}-thiazol-2-yl)-3-(3,4-dichloro-benzyl)-urea;
1-(3,4-dichlorobenzyl)-3-(4-((4-methylpiperazin-1-yl)methyl)thiazol-2-yl)urea;
1-(3,4-dichlorobenzyl)-3-(4-((4-ethylpiperazin-1-yl)methyl)thiazol-2-yl)urea;
1-(3,4-dichlorobenzyl)-3-(4-((4-phenylpiperazin-1-yl)methyl)thiazol-2-yl)urea;
1-(3,4-dichloro-benzyl)-3-[4-(4-pyrimidin-2-yl-piperazin-1-ylmethyl)-thiazol-2-yl]-urea;
1-(4-{[bis-(2-methoxy-ethyl)-amino]-methyl}-thiazol-2-yl)-3-(3,4-dichloro-benzyl)-urea;
({2-[3-(3,4-dichloro-benzyl)-ureido]-thiazol-4-ylmethyl}-methyl-amino)-acetic acid tert-butyl ester;
({2-[3-(3,4-dichloro-benzyl)-ureido]-thiazol-4-ylmethyl}-methyl-amino)-acetic acid;
1-(3,4-dichloro-benzyl)-3-[4-(hexahydro-pyrrolo[1,2-a]imidazol-1-ylmethyl)-thiazol-2-yl]-urea;
1-(3,4-dichloro-benzyl)-3-{4-[(2-methoxy-ethylamino)-methyl]-thiazol-2-yl}-urea;
1-(3,4-dichloro-benzyl)-3-(4-{[(2-methoxy-ethyl)-methyl-amino]-methyl}-thiazol-2-yl)-urea;
1-(3,4-dichloro-benzyl)-3-(4-morpholin-4-ylmethyl-thiazol-2-yl)-urea;
1-(3,4-dichloro-benzyl)-3-(4-{[(2-dimethylamino-ethyl)-methyl-amino]-methyl}-thiazol-2-yl)-urea;
1-(3,4-dichloro-benzyl)-3-(4-{[ethyl-(2-methoxy-ethyl)-amino]-methyl}-thiazol-2-yl)-urea;
1-(3,4-dichloro-benzyl)-3-(4-((dimethylamino)methyl)thiazol-2-yl)urea;
1-(benzo[d][1,3]dioxol-5-ylmethyl)-3-(4-(((2-methoxyethyl)(methyl)amino)methyl)thiazol-2-yl)urea;
1-(benzo[d][1,3]dioxol-5-ylmethyl)-3-(4-(((2-(dimethylamino)ethyl)(methyl)amino)methyl)thiazol-2-yl)urea;
1-(3,4-dichloro-benzyl)-3-(4-{[(2-diethylamino-ethyl)-methyl-amino]-methyl}-thiazol-2-yl)-urea;

1-(3,4-dichloro-benzyl)-3-(4-{[(3-dimethylamino-propyl)-methyl-amino]-methyl}-thiazol-2-yl)-urea;
1-(3,4-dichloro-benzyl)-3-(4-{[(1,1-dioxo-tetrahydro-1-lambda$^6$-thiophen-3-yl)-methyl-amino]-methyl}-thiazol-2-yl)-urea;
1-(3,4-dichloro-benzyl)-3-(4-{[(4-hydroxy-1,1-dioxo-tetrahydro-1-lambda$^6$-thiophen-3-yl)-methyl-amino]-methyl}-thiazol-2-yl)-urea;
1-(3,4-dichloro-benzyl)-3-{4-[(4-hydroxy-1,1-dioxo-tetrahydro-1-lambda$^6$-thiophen-3-ylamino)-methyl]-thiazol-2-yl}-urea;
1-(4-{[(1,1-Dioxo-tetrahydro-1lambda$^6$-thiophen-3-yl)-methyl-amino]-methyl}-thiazol-2-yl)-3-(3-fluoro-benzyl)-urea;
1-(3,4-dichloro-benzyl)-3-(4-{[(2,3-dihydroxy-propyl)-methyl-amino]-methyl}-thiazol-2-yl)-urea;
1-(3,4-dichlorobenzyl)-3-(4-((4-hydroxyisoxazolidin-2-yl)methyl)thiazol-2-yl)urea;
1-(3,4-dichloro-benzyl)-3-[4-(1,1-dioxo-1-lambda$^6$-thiomorpholin-4-ylmethyl)-thiazol-2-yl]-urea;
2-({2-[3-(3,4-dichloro-benzyl)-ureido]-thiazol-4-ylmethyl}-methyl-amino)-N-(1,1-dioxo-tetrahydro-1 lambda$^6$-thiophen-3-yl)-acetamide;
1-(3-fluoro-benzyl)-3-{4-[(methyl-o-tolyl-amino)-methyl]-thiazol-2-yl}-urea;
1-(3-fluoro-benzyl)-3-{4-[(methyl-pyridin-2-yl-amino)-methyl]-thiazol-2-yl}-urea;
1-(3,4-dichloro-benzyl)-3-(4-methylaminomethyl-thiazol-2-yl)-urea;
1-(3,4-dichlorobenzyl)-3-(4-((((3,5-dimethylisoxazol-4-yl)methyl)(methyl)amino)methyl)thiazol-2-yl)urea;
1-(3,4-dichloro-benzyl)-3-(4-{[(2,4-dimethoxy-benzyl)-methyl-amino]-methyl}-thiazol-2-yl)-urea;
1-(3-fluorobenzyl)-3-(4-((((3-(hydroxymethyl)-methylisoxazol-4-yl)methyl)(methyl)amino)methyl)thiazol-2-yl)urea;
1-(3,4-dichloro-benzyl)-3-{4-[(2,3,4-trimethoxy-benzylamino)-methyl]-thiazol-2-yl}-urea;
1-(3,4-dichloro-benzyl)-3-{4-[(2,4-dimethoxy-benzylamino)-methyl]-thiazol-2-yl}-urea;
1-(3,4-dichloro-benzyl)-3-{4-[(2-hydroxy-ethylamino)-methyl]-thiazol-2-yl}-urea;
2-(3-(3,4-dichlorobenzyl)ureido)-N-(2-methoxyethyl)-N-methylthiazole-4-carboxamide;
1-(3-fluorobenzyl)-3-(4-((methyl(3-methylpyrazin-2-yl)amino)methyl)thiazol-2-yl)urea;
1-(3,4-dichlorobenzyl)-3-(4-((2-(methylsulfonamido)ethoxy)methyl)thiazol-2-yl)urea;
Diethyl 2-((2-(3-(3,4-dichlorobenzyl)ureido)thiazol-4-yl)methoxy)ethylphosphor-amidate;
(2-{2-[3-(3,4-dichloro-benzyl)-ureido]-thiazol-4-ylmethoxy}-ethyl)-carbamic acid methyl ester;
1-(3,4-dichloro-benzyl)-3-{4-[2-(3-ethyl-ureido)-ethoxymethyl]-thiazol-2-yl}-urea;
1-(3,4-dichlorobenzyl)-3-(4-((4-methoxyphenylthio)methyl)thiazol-2-yl)urea;
1-(3,4-dichlorobenzyl)-3-(4-((4-fluorophenylthio)methyl)thiazol-2-yl)urea;
1-(3,4-dichlorobenzyl)-3-(4-((4-acetamidophenylthio)methyl)thiazol-2-yl)urea;
1-(3,4-dichlorobenzyl)-3-(4-((3,4-dimethoxyphenylthio)methyl)-thiazol-2-yl)urea;
1-(3,4-dichlorobenzyl)-3-(4-((2-(pyrazin-2-yl)ethylthio)methyl)thiazol-2-yl)urea;
1-(3,4-dichlorobenzyl)-3-(4-((4-methyl-4H-1,2,4-triazol-3-ylthio)methyl)thiazol-2-yl)urea;
1-(4-((1,3,4-thiadiazol-2-ylthio)methyl)thiazol-2-yl)-3-(3,4-dichlorobenzyl)urea;
1-(3,4-dichlorobenzyl)-3-(4-((thiazol-2-ylthio)methyl)thiazol-2-yl)urea;
1-(3,4-dichlorobenzyl)-3-(4-((1-methyl-1H-tetrazol-5-ylthio)methyl)thiazol-2-yl)urea;
1-(3,4-dichlorobenzyl)-3-(4-((4,5-dimethyl-4H-1,2,4-triazol-3-ylthio)methyl)thiazol-2-yl)urea;
1-(3,4-dichloro-benzyl)-3-(3-{[(2-methoxy-ethyl)-methyl-amino]-methyl}-[1,2,4]thiadiazol-5-yl)-urea;
1-(3-fluoro-benzyl)-3-(3-{[(2-methoxy-ethyl)-methyl-amino]-methyl}-[1,2,4]thiadiazol-5-yl)-urea;
1-(3-fluorobenzyl)-3-(3-((2-methoxyethoxy)methyl)-1,2,4-thiadiazol-5-yl)urea;
1-(3,4-dichloro-benzyl)-3-[3-(2-methoxy-ethoxymethyl)-[1,2,4]thiadiazol-5-yl]-urea;
1-(3,4-dichloro-benzyl)-3-(3-{[(1,1-dioxo-tetrahydro-1l6-thiophen-3-yl)-methyl-amino]-methyl}-[1,2,4]thiadiazol-5-yl)-urea;
1-(3-{[(1,1-dioxo-tetrahydro-1l6-thiophen-3-yl)-methyl-amino]-methyl}-[1,2,4]thiadiazol-5-yl)-3-(3-fluoro-benzyl)-urea;
1-(3-{[(3,5-dimethyl-isoxazol-4-ylmethyl)-methyl-amino]-methyl}-[1,2,4]thiadiazol-5-yl)-3-(3-fluoro-benzyl)-urea;
1-(3-fluorobenzyl)-3-(3-((2-(methylsulfonyl)ethoxy)methyl)-1,2,4-thiadiazol-5-yl)urea;
1-(3-fluorobenzyl)-3-(3-((2-(methylsulfinyl)ethoxy)methyl)-1,2,4-thiadiazol-5-yl)urea; and
1-(5-Bromo-4-((2-methoxyethoxy)methyl)thiazol-2-yl)-3-(3,4-dichlorobenzyl)urea.

Preferred compounds of the present invention also include compounds of Formula (Ia), (Ib), (Ic), (Id), (Ie), and (If) as described in Tables 1-6.

TABLE 1

Compounds of Formula (Ia)

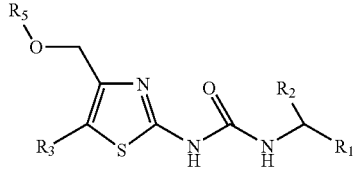

(Ia)

| Example # | R$_5$ | R$_1$ | R$_2$ | R$_3$ |
|---|---|---|---|---|
| 19 | Me- | 3,4-diClPh | H | H |
| 20 | MeO(CH$_2$)$_2$— | 3,4-diClPh | H | H |

TABLE 1-continued

Compounds of Formula (Ia)

(Ia)

| Example # | R$_5$ | R$_1$ | R$_2$ | R$_3$ |
|---|---|---|---|---|
| 21 | CH$_3$(CH$_2$)$_3$— | 3,4-diClPh | H | H |
| 22 | PhO(CH$_2$)$_2$— | 3,4-diClPh | H | H |
| 23 | MeO(CH$_2$)$_3$— | 3,4-diClPh | H | H |
| 24 | EtO(CH$_2$)$_2$— | 3,4-diClPh | H | H |
| 25 | (CH$_3$)$_2$N(CH$_2$)$_2$— | 3,4-diClPh | H | H |
| 26 | CH$_3$S(CH$_2$)$_2$— | 3,4-diClPh | H | H |
| 27 | CH$_3$S(O)(CH$_2$)$_2$— | 3,4-diClPh | H | H |
| 28 | CH$_3$S(O)$_2$(CH$_2$)$_2$— | 3,4-diClPh | H | H |
| 29 | MeO(CH$_2$)$_2$— | 3-FPh | H | H |
| 30 | (CH$_3$)$_3$CO(CH$_2$)$_2$— | 3,4-diClPh | H | H |
| 31 | HO(CH$_2$)$_2$— | 3,4-diClPh | H | H |
| 32 | Ph- | 3,4-diClPh | H | H |
| 33 | CH$_3$S(O)$_2$(CH$_2$)$_2$— | 3-FPh | H | H |
| 49 | MeO(CH$_2$)$_2$— | 3,4-diMePh | H | H |
| 50 | MeO(CH$_2$)$_2$— | 3-BrPh | H | H |
| 51 | MeO(CH$_2$)$_2$— | 3-CF$_3$, 4-ClPh | H | H |
| 52 | MeO(CH$_2$)$_2$— | Benzo [1,3]dioxol-5-yl | H | H |
| 53 | MeO(CH$_2$)$_2$— | 3-Cl, 4-FPh | H | H |
| 54 | MeO(CH$_2$)$_2$— | 3-ClPh | H | H |
| 55 | MeO(CH$_2$)$_2$— | 3-IPh | H | H |
| 56 | MeO(CH$_2$)$_2$— | 4-BrPh | H | H |
| 57 | MeO(CH$_2$)$_2$— | 4-BrPh | CH$_3$ | H |
| 58 | MeO(CH$_2$)$_2$— | 3-F, 4-ClPh | H | H |
| 59 | MeO(CH$_2$)$_2$— | 3-Br, 4-ClPh | H | H |
| 60 | MeO(CH$_2$)$_2$— | 3,5-diFPh | H | H |
| 61 | MeO(CH$_2$)$_2$— | 3,4,5-triFPh | H | H |
| 62 | MeO(CH$_2$)$_2$— | 4,5-diBr, 2-thiophene | H | H |
| 63 | MeO(CH$_2$)$_2$— | 2,2-diF Benzo [1,3]dioxol-5-yl | H | H |
| 64 | MeO(CH$_2$)$_2$— | 3-Cl, 5-FPh | H | H |
| 65 | MeO(CH$_2$)$_2$— | 3-thiophene | H | H |
| 66 | MeO(CH$_2$)$_2$— | 2-thiophene | H | H |
| 67 | MeO(CH$_2$)$_2$— | 5-Br, 2-thiophene | H | H |
| 68 | MeO(CH$_2$)$_2$— | 5-Cl, 2-thiophene | H | H |
| 69 | MeO(CH$_2$)$_2$— | 4-FPh | H | H |
| 70 | CH$_3$S(O)$_2$(CH$_2$)$_2$— | 3-ClPh | H | H |
| 71 | CH$_3$S(O)$_2$(CH$_2$)$_2$— | 3-BrPh | H | H |
| 77 | BocNH(CH$_2$)$_2$— | 3,4-diClPh | H | H |
| 78 | H$_2$N(CH$_2$)$_2$— | 3,4-diClPh | H | H |
| 79 | Morpholin-4-yl-(CH$_2$)$_2$— | 3,4-diClPh | H | H |
| 80 | AcNH(CH$_2$)$_2$— | 3,4-diClPh | H | H |
| 81 | CH$_3$S(CH$_2$)$_2$— | Benzo [1,3]dioxol-5-yl | H | H |
| 82 | CH$_3$S(O)(CH$_2$)$_2$— | Benzo [1,3]dioxol-5-yl | H | H |
| 83 | CH$_3$S(O)$_2$(CH$_2$)$_2$— | Benzo [1,3]dioxol-5-yl | H | H |
| 84 | MeO(CH$_2$)$_2$O(CH$_2$)$_2$— | 3,4-diClPh | H | H |
| 85 | 4-Me-piperazin-1yl-(CH$_2$)$_2$— | 3,4-diClPh | H | H |
| 86 | 2-imidazol-1-yl-(CH$_2$)$_2$— | 3,4-diClPh | H | H |
| 87 | MeO(CH$_2$)$_2$O(CH$_2$)$_2$O(CH$_2$)$_2$— | 3,4-diClPh | H | H |
| 88 | (1-Me-1H-imidazol-2-yl)-S(CH$_2$)$_2$— | 3,4-diClPh | H | H |
| 89 | (4-Me-thiazol-5-yl)-(CH$_2$)$_2$— | 3,4-diClPh | H | H |
| 90 | Allyl- | 3,4-diClPh | H | H |
| 91 | HOCH$_2$CH(OH)CH$_2$— | 3,4-diClPh | H | H |
| 92 | (Pyridine-2-yl)-(CH$_2$)$_3$— | 3,4-diClPh | H | H |
| 93 | (Pyridine-3-yl)-(CH$_2$)$_2$— | 3,4-diClPh | H | H |
| 94 | (Octahydro-quinolizine-1-yl)-CH$_2$— | 3,4-diClPh | H | H |
| 95 | (Pyrrolidin-1-yl)-(CH$_2$)$_2$— | 3,4-diClPh | H | H |
| 96 | 1-Me-piperidin-4-yl | 3,4-diClPh | H | H |
| 97 | 2-oxooxazolidin-3-yl | 3,4-diClPh | H | H |
| 98 | (methylsulfonamido)-(CH$_2$)$_2$— | 3-FPh | H | H |
| 99 | 3-methylcarboxylate-pyrazin-2-yl | 3-FPh | H | H |

TABLE 1-continued

Compounds of Formula (Ia)

(Ia)

| Example # | R$_5$ | R$_1$ | R$_2$ | R$_3$ |
|---|---|---|---|---|
| 100 | 3-Me-pyrazin-2-yl | 3-FPh | H | H |
| 142 | CH$_3$S(O)$_2$NH(CH$_2$)$_2$— | 3,4-diClPh | H | H |
| 143 | (CH$_3$CH$_2$O)$_2$P(O)$_2$NH(CH$_2$)$_2$— | 3,4-diClPh | H | H |
| 144 | CH$_3$OC(O)NH(CH$_2$)$_2$— | 3,4-diClPh | H | H |
| 145 | CH$_3$CH$_2$NHC(O)NH(CH$_2$)$_2$— | 3,4-diClPh | H | H |
| 173 | MeO(CH$_2$)$_2$— | 3,4-diClPh | H | Br |

TABLE 2

Compounds of Formula (Ib)

(Ib)

| Ex # | R$_5$ | R$_6$ | R$_1$ |
|---|---|---|---|
| 45 | MeO(CH$_2$)$_2$— | —CH$_3$ | 3-BrPh |
| 46 | MeO(CH$_2$)$_2$— | —CH$_3$ | 3-ClPh |
| 47 | MeO(CH$_2$)$_2$— | —CH$_3$ | 3-FPh |
| 48 | MeO(CH$_2$)$_2$— | —CH$_3$ | 3-Cl, 4-FPh |
| 102 | t-BuOC(O)NHCH$_2$CH$_2$— | —CH$_3$ | 3,4-diClPh |
| 103 | NH$_2$CH$_2$CH$_2$— | —CH$_3$ | 3,4-diClPh |
| 108 | MeOCH$_2$CH$_2$— | MeOCH$_2$CH$_2$— | 3,4-diClPh |
| 109 | (CH$_3$)$_3$COC(O)CH$_2$— | —CH$_3$ | 3,4-diClPh |
| 110 | HOC(O)CH$_2$— | —CH$_3$ | 3,4-diClPh |
| 112 | MeO(CH$_2$)$_2$— | H | 3,4-diClPh |
| 113 | MeO(CH$_2$)$_2$— | —CH$_3$ | 3,4-diClPh |
| 115 | (CH$_3$)$_2$NCH$_2$CH$_2$— | —CH$_3$ | 3,4-diClPh |
| 116 | MeO(CH$_2$)$_2$— | —CH$_2$CH$_3$ | 3,4-diClPh |
| 117 | CH$_3$— | —CH$_3$ | 3,4-diClPh |
| 118 | MeO(CH$_2$)$_2$— | —CH$_3$ | Benzo[1,3]dioxol-5-yl |
| 119 | (CH$_3$)$_2$NCH$_2$CH$_2$— | —CH$_3$ | Benzo[1,3]dioxol-5-yl |
| 120 | (CH$_3$CH$_2$)$_2$NCH$_2$CH$_2$— | —CH$_3$ | 3,4-diClPh |
| 121 | (CH$_3$)$_2$NCH(CH$_2$)$_2$— | —CH$_3$ | 3,4-diClPh |
| 122 | 1,1-dioxo-tetrahydro-1-lambda$^6$-thiophen-3-yl | —CH$_3$ | 3,4-diClPh |
| 123 | 4-hydroxy-1,1-dioxo-tetrahydro-1-lambda$^6$-thiophen-3-yl | —CH$_3$ | 3,4-diClPh |
| 124 | 4-hydroxy-1,1-dioxo-tetrahydro-1-lambda$^6$-thiophen-3-yl | H | 3,4-diClPh |
| 125 | 1,1-dioxo-tetrahydro-1-lambda$^6$-thiophen-3-yl | —CH$_3$ | 3-FPh |
| 126 | HOCH$_2$CH(OH)CH$_2$— | —CH$_3$ | 3,4-diClPh |
| 129 | N-(1,1-dioxo-tetrahydro-1lambda$^6$-thiophen-3-yl)-acetamide | —CH$_3$ | 3,4-diClPh |
| 130 | o-tolyl- | —CH$_3$ | 3-FPh |
| 131 | pyridin-2-yl | —CH$_3$ | 3-FPh |
| 132 | CH$_3$— | H | 3,4-diClPh |
| 133 | (3,5-dimethylisoxazol-4-yl)-CH$_2$— | —CH$_3$ | 3,4-diClPh |
| 134 | 2,4-dimethoxy-benzyl | —CH$_3$ | 3,4-diClPh |
| 135 | 3-(hydroxymethyl)-5-methylisoxazol-4-yl)-CH$_2$— | —CH$_3$ | 3-FPh |
| 136 | 2,3,4-trimethoxy-benzyl | H | 3,4-diClPh |
| 137 | 2,4-dimethoxy-benzyl | H | 3,4-diClPh |
| 138 | HO(CH$_2$)$_2$— | H | 3,4-diClPh |
| 140 | 3-Me-pyrazin-2-yl | —CH$_3$ | 3-FPh |

TABLE 3

Compounds of Formula (Ic)

(Ic)

| Ex. # | N/R₅/R₆ | R₁ |
|---|---|---|
| 101 | 4-formyl-piperazin-1-yl | 3,4-diClPh |
| 104 | 4-methylpiperazin-1-yl- | 3,4-diClPh |
| 105 | 4-ethylpiperazin-1-yl- | 3,4-diClPh |
| 106 | 4-phenylpiperazin-1-yl- | 3,4-diClPh |
| 107 | 4-pyrimidin-2-yl-piperazin-1-yl | 3,4-diClPh |
| 111 | Hexahydroxy-pyrrolo[1,2-a]imidazole-1-yl | 3,4-diClPh |
| 114 | Morpholin-4-yl | 3,4-diClPh |
| 127 | 4-hydroxyisoxazolidin-2-yl | 3,4-diClPh |
| 128 | 1,1-dioxo-1-lambda⁶-thiomorpholin-4-yl | 3,4-diClPh |

TABLE 4

Compounds of Formula (Id)

(Id)

| Ex # | R₄, R₄' | Y | R₅, R₆ | R₁ |
|---|---|---|---|---|
| 35 | H | C | O, OEt | 3,4-diClPh |
| 36 | H | C | OH, H | 3,4-diClPh |
| 37 | H | C | OH, H | 3-FPh |
| 38 | O | O | Et, null | 3,4-diClPh |
| 39 | H | O | H, null | 3,4-diClPh |
| 139 | O | N | CH₃, MeO(CH₂)₂— | 3,4-diClPh |

TABLE 5

Compounds of Formula (Ie)

(Ie)

| Ex. # | R₅ |
|---|---|
| 147 | 4-MeO-Ph |
| 148 | 4-F-Ph |
| 149 | 4-acetamido-Ph |
| 150 | 3,4-dimethoxy-Ph |
| 151 | (Pyrazin-2-yl)-(CH₂)₂— |
| 152 | 4-methyl-4H-1,2,4-triazol-3-yl |
| 153 | 1,3,4-thiadiazol-2-yl |
| 154 | thiazol-2-yl |

TABLE 5-continued

Compounds of Formula (Ie)

(Ie)

| Ex. # | R₅ |
|---|---|
| 155 | 1-methyl-1H-tetrazol-5-yl |
| 156 | 4,5-dimethyl-4H-1,2,4-triazol-3-yl |

TABLE 6

Compounds of Formula (If)

(If)

| Ex. # | Y | R₅ | R₆ | R₁ |
|---|---|---|---|---|
| 164 | N | MeO(CH₂)₂— | CH₃ | 3,4-diClPh |
| 165 | N | MeO(CH₂)₂— | CH₃ | 3-FPh |
| 166 | O | MeO(CH₂)₂— | null | 3-FPh |
| 167 | O | MeO(CH₂)₂— | null | 3,4-diClPh |
| 168 | N | 1,1-dioxo-tetrahydro-1-lambda⁶-thiophen-3-yl | CH₃ | 3,4-diClPh |
| 169 | N | 1,1-dioxo-tetrahydro-1-lambda⁶-thiophen-3-yl | CH₃ | 3-FPh |
| 170 | N | 3,5-Dimethyl-isoxazol-4-ylmethyl- | CH₃ | 3-FPh |
| 171 | O | CH₃S(O)₂(CH₂)₂— | null | 3-FPh |
| 172 | O | CH₃S(O)(CH₂)₂— | null | 3-FPh |

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula (I) or a salt and/or solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

When used herein, the term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

When used herein, the term "hydrate" is a solvate wherein the solvent molecule is H₂O.

As used herein, the phrases "effective amount" or "therapeutically effective amount" are meant to describe an amount of compound or a composition of the present invention effective in inhibiting bacterial replication and thus producing the desired therapeutic, ameliorative, inhibitory or preventative effect.

The compounds of Formula (I), (referral to Formula (I) herein by definition includes compounds of Formulas (Ia), (Ib), (Ic), (Id), (Ie) and (If)) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates, or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by S. Berge et al, Journal of Pharmaceutical Sciences (1977) 66(1)119; P. Gould, International J. of Pharmaceutics (1986) 33 201 217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), arylalkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula (I) and salts, solvates and prodrugs thereof, may exist in their tautomeric form (for example, as an amide or imino ether). All such tautomeric forms are contemplated herein as part of the present invention. All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Compounds of Formula (I) are inhibitors of PolC, a type II DNA Polymerase III, which is the major replicative polymerase responsible for chromosomal replication in low GC Gram-positive bacteria. Compounds of Formula (I) are generally selective for PolC, showing little or no inhibition of the eukaryotic replicative polymerase, i.e., provides an optimal combination of high activity against various pathogenic bacteria and low or no activity against mammalian calls, allowing the use of compounds of the invention in the treatment of mammals, and in particular humans.

Compounds of the present invention show antibacterial activity against clinically relevant Gram-positive pathogens, including *S. pyogenes, S. aureus, S. pneumoniae* and *E. faecalis*. Compounds of the present invention demonstrate preferential inhibition of DNA synthesis over RNA, protein, or cell wall synthesis in whole cell assays. Therapeutic compositions of the present invention have antibacterial activity against clinically important Gram-positive pathogens, including *staphylococci* and *streptococci*, and particularly including isolates resistant to currently marketed agents.

Another aspect of this invention is a method of protecting a patient from a bacterial infection. A patient may be an animal, preferably a mammal and even more preferably a human having or susceptible to a disease or condition associated with a bacterial infection. Protecting may be prophylactic, i.e., administering a compound of the present invention in the absence of a diagnosed bacterial infection, or therapeutic, i.e., administering a compound of the present invention upon diagnosis of a bacterial infection. Protection may be achieved by administering a therapeutically effective amount of at least one compound of Formula (I), or a pharmaceutically acceptable salt or solvate of said compound to the patient. A preferred dosage is about 0.001 to 500 mg/kg of body weight/day of the compound of Formula (I) or a pharmaceutically acceptable salt or solvate of said compound. An especially preferred dosage is about 0.01 to 25 mg/kg of body weight/day of a compound of Formula (I), or a pharmaceutically acceptable salt or solvate of said compound.

Methods to diagnose bacterial infection in patients are known in the art. Preferred bacterial infections to treat include bacterial infections caused by any bacteria type or species against which the compounds of the present invention have an antibacterial effect. Particularly preferred bacteria types or species include Gram-positive and Gram-negative bacteria and most preferred bacterial types include Gram-positive bacteria.

In order to protect an animal from bacterial infection, a therapeutic or prophylactic composition of the present invention is administered to the animal in an effective manner such that bacterial infection is minimized and/or reduced. Preferably, the bacterial infection and/or bacterial burden of the infectious bacteria is reduced by at least about 50%, at least about 70%, and more preferably at least about 90%, 95% or 97%.

Suitable patients to treat include humans; birds such as chickens, ostriches, quail, and turkeys; mammals such as companion animals (including dogs, cats, and rodents) and economic food and/or fur or other product animals, such as horses, cattle, llamas, chinchillas, ferrets, goats, sheep, rodents, minks, rabbits, raccoons, and swine.

The compounds of this invention can also be useful in combination (administered together or sequentially) with one or more of antibacterial treatments, such as, for example, treatment with other known antibacterial drug classes such as, for example, β-lactams, glycopeptides, oxazolidinones, macrolides, ketolides, quinolones, fluoroquinolones, aminoglycosides, tetracyclines, and lipopeptides. If formulated as a fixed dose, such combination products employ the compounds of this invention within the dosage range described herein and the other pharmaceutically active agent or treatment within its dosage range. Compounds of Formula (I) may also be administered sequentially with known antibacterial agents when a combination formulation is inappropriate. The invention is not limited in the sequence of administration; compounds of Formula (I) may be administered either prior to or after administration of the known antibacterial agent. Such techniques are within the skills of persons skilled in the art as well as attending physicians.

Accordingly, in an aspect, this invention includes combinations comprising an amount of at least one compound of Formula (I), or a pharmaceutically acceptable salt or solvate thereof, and an amount of one or more antibacterial agents or treatments listed above wherein the amounts of the compounds/treatments result in desired therapeutic effect. The pharmacological properties of the compounds of this invention may be confirmed by a number of pharmacological assays. The exemplified pharmacological assays which are described herein have been carried out with compounds according to the invention and/or their salts.

In another aspect, the invention includes pharmaceutical compositions which comprise at least one compound of Formula (I), or a pharmaceutically acceptable salt or solvate of said compound, and at least one pharmaceutically acceptable carrier. Accordingly, the present invention further includes compositions comprising one or more compounds of Formula (I) and a pharmaceutically acceptable carrier.

When used herein, the phrase "pharmaceutically acceptable carrier" refers to media generally accepted in the art for the delivery of biologically active agents to patients, in particular, mammals. Pharmaceutically acceptable carriers are typically formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 17th ed., Mack Publishing Company, Easton, Pa., 1985, which is incorporated herein by reference in its entirety.

Preparation of Pharmaceutical Compositions of the Invention Include Inclusion of inert, solid or liquid pharmaceutically acceptable carriers. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, silica, sucrose, lactose, starch, or cellulose derivatives. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example, water or water-propylene glycol solutions for parenteral injection or addition of sweeteners and opacifiers for oral solutions, suspensions and emulsions, can be used. Liquid form preparations may also include solutions for intranasal administration. Gelatin capsules can be used to contain the active ingredient and a suitable carrier such as, but not limited to, lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract. Liquid dose forms for oral administration can also contain coloring or flavoring agents to increase patient acceptance.

Typically, water, pharmaceutically acceptable oils, saline, aqueous dextrose, and related sugar solutions and glycols, such as propylene glycol or polyethylene glycol, are suitable carriers for parenteral solutions. Solutions for parenteral administration can contain, for example, a water soluble salt of the active ingredient and suitable stabilizing agent(s). Antioxidizing agents, such as sodium bisulfite, sodium sulfite, or ascorbic acid, either alone or in combination, can act as suitable stabilizing agents. Also suitable as stabilizing agents are citric acid and its salts, and EDTA. In addition, parenteral solutions can contain preservatives such as, for example, benzalkonium chloride, methyl- or propyl-paraben, and chlorobutanol.

Oral compositions are preferred and will generally include an inert diluent or an edible carrier and may be compressed into tablets or enclosed in gelatin capsules. The oral dosage forms are administered to the patient weekly, twice weekly, three times weekly, four times weekly, five times weekly, six times weekly, or 1, 2, 3, or 4 times daily. It is preferred that the compounds of the invention be administered either three or fewer times daily, more preferably once or twice daily. For purposes of oral therapeutic administration, the active compound or compounds can be incorporated with excipients and used in the form of tablets, capsules, lozenges, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes, colorings, and flavors. The active materials can also be mixed with other active materials that do not impair the desired action, or with materials that supplement the desired action.

Solutions or suspensions used for parenternal, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenternal preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known, for example, as described in U.S. Pat. No. 4,522,811, which is incorporated by reference herein.

The active compounds may be prepared with carriers that protect the compound against rapid elimination from the body, such as time-release formulations or coatings such as enteric coatings to protect the compounds of the present invention from the acidic environment of the stomach. Enteric coated tablets are well known to those skilled in the art. In addition, capsules filled with small spheres, each coated to protect from the acidic stomach, are also well known to those skilled in the art. Other such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenterally (IV, IM, depo-IM, SQ, and depo-SQ), sublingually, intranasally (inhalation), intrathecally, topically, or rectally. Dosage forms known to those skilled in the art are suitable for delivery of the compounds of the invention.

When administered orally, compounds of the invention can be administered in usual dosage forms for oral administration as is well known to those skilled in the art and are described more fully herein. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The compounds of the invention can be administered parenterally, for example, by IV, IM, depo-IM, SC, or depo-SC. When administered parenterally, a therapeutically effective amount for humans of about 0.5 to about 100 mg/day, preferably from about 5 to about 50 mg daily should be delivered. When a depot formulation is used for injection once a month or once every two weeks, the dose for humans should be about 0.5 mg/day to about 50 mg/day, or a monthly dose of from about 15 mg to about 1,500 mg. Dosing for other types of patients can be estimated from the appropriate human dose.

The compounds of the invention can be administered sublingually. When given sublingually, the compounds of the invention should be given one to four times daily in the amounts described above for IM administration.

The compounds of the invention can also be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenteral dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. When administered topically, the dosage is from about 0.5 mg/day to about 200 mg/day. The compounds of the invention can be administered rectally by suppository as is known to those skilled in the art. When administered by suppository, the therapeutically effective amount is from about 0.5 mg to about 500 mg for humans. The compounds of the invention can be administered by implants as is known to those skilled in the art. When administering a compound of the invention by implant, the therapeutically effective amount is the amount described above for depot administration.

The invention herein is the novel compounds of the invention and new methods of using the compounds of the invention. Given a particular compound of the invention and a desired dosage form, one skilled in the art would know how to prepare and administer the appropriate dosage form.

Where the compounds of the invention exhibit insufficient solubility, methods for solubilizing may be used. Such methods are known and include, but are not limited to, using cosolvents such as dimethylsulfoxide (DMSO), using surfactants such as polysorbates including Tween® and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration. A suitable single dose is a dose that is capable of reducing bacterial infection and/or bacterial burden with the infectious bacteria when administered one or more times over a suitable time period. For example, a preferred single dose of a compound of Formula (I) ranges from about 1 microgram to about 10 milligrams, but can range up to 100 milligrams of the composition per kilogram body weight of the patient.

The active compound is typically included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound of the invention in lyophilized form, and a suitable diluent, may be provided as separated components for combination prior to use. A kit may include a compound of the invention and a second therapeutic agent for co-administration. The compound of the invention and second therapeutic agent may be provided as separate component parts.

A kit herein may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, ointments, and the like for topical administration.

The concentration of active compound in the drug composition will depend on absorption, inactivation, and excretion rates of the active compound, the dosage schedule, and amount administered as well as other factors known to those of skill in the art. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data.

It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the composition(s), and that the concentration ranges set forth herein are exemplary only and are not intended to limit the scope or practice of the claimed compositions.

In one aspect, compounds of Formula (I) may be readily prepared by reacting a compound of Formula (II)

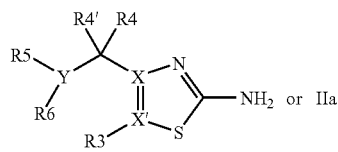

(II)

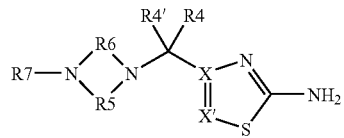

(IIa)

in which $R_3$, $R_4$, $R_{4'}$, $R_5$, $R_6$, $R_7$, X, X' and Y are as hereinbefore defined; with:

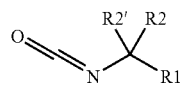

(III)

in which $R_1$, $R_2$, and $R_{2'}$ are as hereinbefore defined. Suitable conditions for the urea formation are well known in the art and include for instance, the use of N,N-diisopropylethylamine in a solvent system such as THF.

Alternatively compounds of Formula (I) may be readily prepared by reaction of a phenyl carbamate compound of formula IV

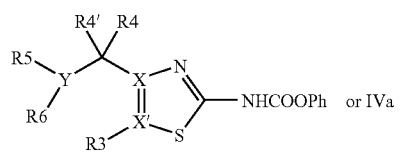

(IV)

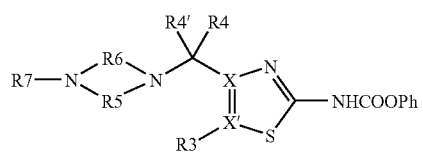

(IVa)

in which $R_3$, $R_4$, $R_{4'}$, $R_5$, $R_6$, $R_7$, X, Y are as hereinbefore defined; with:

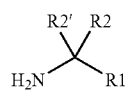

(V)

in which $R_1$, $R_2$ and $R_{2'}$ are as hereinbefore defined, under standard conditions. Condensations with phenylcarbamates are typically carried out in refluxing ethereal solvents for a period of 2-24 h, or alternatively heated in a microwave for 5-30 min at 120°-160° C.

Alternatively, compounds of Formula (I) may be readily prepared by reacting a chloromethyl compound of Formula (VI)

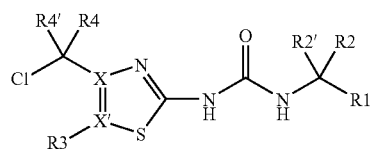

(VI)

in which $R_1$, $R_2$, $R_4$ and X are as hereinbefore defined and the chloro atom services as a leaving group; with either (a) an alcohol of Formula (VIIa):

(VIIa)

in which $R_5$ is an alkyl as hereinbefore defined under standard alkylation conditions;

(b) a mercaptan of Formula (VIIb):

(VIIb)

in which $R_5$ is an alkyl as hereinbefore defined under standard alkylation conditions;

(c) an amine of Formula (VIIc)

(VIIc)

in which $R_5$ and $R_6$ are independently selected from H, substituted or unsubstituted alkyl, or substituted or unsubstituted O-alkyl as hereinbefore defined under standard alkylation conditions; or (d) an amine of Formula (VIId)

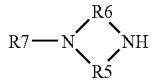

(VIId)

in which $R_5$, $R_6$, $R_7$ are as hereinbefore defined, under standard alkylation conditions;

alkylation of alcohol or mercaptan is well known in the art and include for instance, use of sodium hydride and 15-Crown-5 in a solvent system such as THF and are carried out 0° C. for 2-16 h. Alkylation of an amine is well known in the art and includes for instance, N,N-diisopropylethylamine in a solvent system such as THF and are carried out in refluxing THF for a period of 6-24 h, or alternatively heated in a microwave for 30 min at 150° C.

The invention disclosed herein is exemplified by the following preparations and examples which should not be construed to limit the scope of the disclosure. Alternative mechanistic pathways and analogous structures will be apparent to those skilled in the art.

EXAMPLES

The following abbreviations are provided for convenience of review of Examples 1-173:
TLC=thin layer chromatography
eq.=equivalents
equiv.=equivalents
THF=tetrahydrofuran
DIPEA=diisopropylethylamine
DIEA=diisopropylethylamine
DCM=dichloromethane
MeOH=methanol
EtOAc=ethyl acetate
BOC$_2$O=di-tert-butyl dicarbonate
mCPBA=3-chloroperbenzoic acid
DMAP=4-(Dimethylamino)pyridine
TFA=trifluoroacetic acid
DMA=N,N-dimethylacetamide
TBTU=O-(Benzotriazol-1-yl)-N,N,N',N'-tetramethyluronium tetrafluoroborate
DMSO=dimethyl sulfoxide
Et$_2$O=diethyl ether
MeCN=acetonitrile
DMF=N,N-dimethylformamide
NMP=1-Methyl-2-pyrrolidinone Example 1

Demonstration of Antibacterial Effect and Mechanism of Action

The polC gene from *Streptococcus pyogenes* was overexpressed and PolC was purified as described in PCT/JUS05/15548. Primer extension activity of PolC was measured using 1 μM oligonucleotide primer-template (primer strand 5'-ACCAGTGAGACGGGCAACA (SEQ ID NO: 1), template strand 5'-TGAATTATAGGCCCTGTTGCCCGTCTCACTGGT SEQ ID NO: 2)). Reactions contained 10 mM magnesium acetate, 50 mM Tricine/Tris pH 7.8, 2.4% (w/v) polyethylene glycol (~8000 MW), 0.024% pluronic F68, 1 mM dithiothreitol, 20 μM dATP, 20 μM dCTP, 0.5 μM dGTP, 0.72 μM dTTP, 0.28 μM 3H-dTTP (0.005 μCi/μL), 8% DMSO and 15 nM PolC. Reactions (25 μL) were incubated for 10 minutes at room temperature and stopped by addition of an equal volume of 100 mM EDTA. Incorporation of radiolabelled dTTP was measured by scintillation proximity assay by addition of 100 μL of 1 mg/mL PEI-PVT beads in 300 mM citrate pH 3.0.

Compounds of formula (I) were tested for inhibition of *S. pyogenes* PolC activity. Serial 2-fold dilutions of compounds were tested for inhibition of PolC activity and IC$_{50}$'s were determined (XLfit). Compounds described in Examples 19, 21-32, 34-37, 39, 47-48, 52-54, 56, 59-63, 67-69, 77-130, 132-140, 142-145, 147-156, and 164-172 had IC$_{50}$'s of 0.11-25 μM. These compounds were specific for prokaryotic DNA polymerase, showing little or no inhibition of eukaryotic *S. cerevisiae* polymerase delta at concentrations up to 160 μM.

A subset of these analogs were tested for inhibition of macromolecular biosynthesis in whole cell *S. aureus* assays as described by Ochsner et al. (Antimicrobial Agents Chemo. 49:4253-62, 2005). All tested analogs were potent inhibitors of DNA synthesis, with IC$_{50}$'s of <0.06-12.2 μg/mL; the compounds showed little or no inhibition of other macromolecular synthesis pathways (RNA, protein or cell wall biosynthesis) at concentrations as high as 64 μg/mL.

Compounds of the present invention were tested for antibacterial activity against a variety of pathogenic organisms including *S. aureus, S. pneumoniae, S. pyogenes, E. faecalis, H. influenza* and *M. catarrhalis* using a standard broth microdilution method to determine their minimum inhibitory concentrations (MICs). All compounds were tested using standard methods in accordance with CLSI guidelines (Clinical and Laboratory Standards Institute). Compounds described in Examples 21, 23-31, 33-37, 39, 45-48, 52, 56-65, 67-71, 78-108, 111-140, 142-145, 149, 151-156, and 164-172 had MIC's of 0.12-4.0 μg/mL against some strains of the major Gram-positive organisms *S. aureus, S. pneumoniae, S.* pyogenes, and *E. faecalis*. The compound described in Example 31 was shown to be bactericidal in time kill kinetic studies in *S. aureus, S. pneumoniae*, and *E. faecalis*. Compound 28 was shown to be bactericidal in *S. aureus, S. epidermidis, S. pyogenes, E. faecalis, E. faecium* and *S. pneumoniae*. Compounds of the present invention were not compromised by existing resistance to all drug classes tested, including β-lactams, glycopeptides, oxazolidinones, macrolides, and fluoroquinolones. In particular, the compound described in Example 31 was active against methicillin-(oxacillin-) resistant *S. aureus* (MRSA), vancomycin-intermediate *S. aureus* (VISA), linezolid-resistant *S. aureus*, methicillin-(oxacillin-) resistant *S. epidermidis*, macrolide-resistant *S. pyogenes*, macrolide-, penicillin-, and levofloxacin-resistant *S. pneumoniae*, and vancomycin-resistant *E. faecalis* (VRE). MICs were comparable in sensitive versus drug resistant strains, and ranged from 1-32 µg/mL in clinically relevant resistant strains. The compound described in Examples 28 was shown to be active against methicillin-(oxacillin-) resistant *S. aureus* (MRSA), vancomycin-intermediate *S. aureus* (VISA), linezolid-resistant *S. aureus*, methicillin-(oxacillin-) resistant and mupirocin resistant *S. epidermidis*, macrolide-resistant *S. pyogenes*, macrolide-, penicillin-, and levofloxacin-resistant *S. pneumoniae*, vancomycin-, macrolide-, and ciprofloxacin-resistant *E. faecalis* (VRE) and vancomycin-, macrolide-, and ciprofloxacin-resistant *E. faecium*. MICs were comparable in sensitive versus drug resistant strains, and ranged from 0.5-4 µg/mL in clinically relevant resistant strains.

Compounds of the present invention showed broad spectrum antibacterial activity against Gram-positive bacteria. The compound described in Example 28 exhibited $MIC_{90}$'s ranging from 1-8 µg/mL for methicillin-(oxacillin-) resistant *S. aureus* (MRSA), vancomycin-resistant *E. faecalis* (VRE), vancomycin-resistant *E. faecium* and macrolide-resistant *S. pyogenes*. It exhibited weak Gram-negative antibacterial activity, with MICs of 64->128 µg/mL against *E. coli* tolC, *P. aeruginosa, H. influenzae* and *M. catarrhalis*.

Example 2

Preparation of 2-Amino-4-(chloromethyl)thiazole hydrochloride (Intermediate I)

A solution of thiourea (15.0 g, 197.1 mmol) in acetone (750 ml) was added dropwise over three hours to a stirred solution of 1,3-dichloroacetone (24.9 g, 199.8 mmol) in acetone (120 ml). After complete addition, stirring was continued for 18 hours at ambient temperature. The precipitate was collected by filtration and washed with cold acetone. The white solid was dried under vacuum, yield: 90% (32.8 g, 177.2 mmol).

Or alternatively:

To a solution of 1,3-dichloroacetone (150 g, 1.18 mol) in acetone (600 mL) was added a solution of thiourea (91.7 g, 1.23 mol) in acetone (3000 µL). The mixture was stirred overnight at ambient temperature. The resulting suspension was concentrated to dryness in vacuo. Ethanol (1.2 L) was added and the mixture was stirred for 3 h. The insolubles were removed by filtration and the filtrate was concentrated to 500 mL. Heptane (1.5 L) was slowly added resulting in the formation of a white precipitate. This was isolated by filtration, washed with heptane and dried in vacuo to afford the title compound (I) as a white solid (141.3 g, 0.76 mol, 64%). $^1$H-NMR (300 MHz, DMSO-$d_6$): δ 9.50 (bs, 3H), 7.00 (s, 1H), 4.68 (s, 2H). MS (ES+): M/Z 149 and 151 (M+1).

Example 3

Preparation of tert-Butyl-4-(chloromethyl)thiazol-2-ylcarbamate (Intermediate II)

To a solution of intermediate 1 (3.0 g, 16.2 mmol) in 1,4-dioxane (35 ml) was added triethylamine (3.3 g, 32.6 mmol) and di-tert-butyl dicarbonate (7.11 g, 32.6 mmol) at 2° C. This mixture was stirred for 6 days at ambient temperature. The solvent was removed under reduced pressure and the crude material purified by column chromatography (silica gel, ethyl acetate/heptane 1:3) to give 24% (991 mg, 3.98 mmol) of the title compound as a white solid. $^1$H NMR (300 MHz, $CDCl_3$) δ 1.55 (s, 9H), 4.62 (s, 2H), 6.88 (s, 1H), 9.63 (s, br, 1H). MS (ES+): M/Z 271 and 273 (M+Na).

Example 4

Preparation of tert-Butyl-4-((2-methoxyethoxy)methyl)thiazol-2-ylcarbamate (Intermediate III)

A mixture of the chloride (Intermediate II, 420 mg, 1.69 mmol) and potassium carbonate (818 mg, 5.92 mmol) in 2-methoxyethanol (12 ml) was stirred for 2 hours at 90° C. TLC indicated complete conversion. The mixture was filtered through a pad of celite and the solvent was removed under vacuum. The residue was purified by column chromatography (silica gel, ethyl acetate/heptane, 25-70% gradient) to give 46% (225 mg, 781 µmol) of title compound as pale yellow oil. $^1$H NMR (300 MHz, $CDCl_3$) δ 1.56 (s, 9H), 3.39 (s, 3H), 3.54-3.58 (m, 2H), 3.64-3.69 (m, 2H), 4.58 (s, 2H), 6.82 (s, 1H).

Example 5

Preparation of tert-Butyl-4-(methoxymethyl)thiazol-2-ylcarbamate (Intermediate IV)

To a solution of the chloride II (500 mg, 2.01 mmol) in methanol (25 ml) was added potassium carbonate (1096 mg, 7.93 mmol) and the mixture was stirred for 110 minutes at 75° C. The crude material was evaporated onto celite and purified by column chromatography (silica gel, ethyl acetate/heptane, 25-70% gradient), yielding 54% (266 mg, 1.09 mmol) of title compound as yellow oil. $^1$H NMR (300 MHz, $CDCl_3$) δ 1.54 (s, 9H), 3.43 (s, 3H), 4.46 (s, 2H), 6.79 (s, 1H).

Example 6

Preparation of 4-((2-Methoxyethoxy)methyl)thiazol-2-amine hydrochloride (Intermediate V)

Carbamate III (Example 4) (225 mg, 781 µmol) was stirred at ambient temperature with HCl/dioxane (4 M, 4 ml) for 18 hours. Volatiles were removed under reduced pressure and the residue was azeotroped several times with toluene. $^1$H NMR (300 MHz, $CD_3OD$) δ 3.37 (s, 1H), 3.55-3.59 (m, 2H), 3.64-3.68 (m, 2H), 4.43 (s, 2H), 6.82 (s, 1H).

Example 7

Preparation of 4-(Methoxymethyl)thiazol-2-amine hydrochloride (Intermediate VI)

Carbamate IV (Example 5) (254 mg, 1.04 mmol) was stirred with HCl/dioxane (4 M, 15 mL) for 24 hours, the mixture was allowed to warm from 0° C. to ambient temperature over this period. Volatiles were removed under reduced pressure and the residue was azeotroped several times with toluene. $^1$H NMR (300 MHz, CD$_3$OD) δ 3.37 (s, 3H), 4.34 (s, 2H), 6.82 (s, 1H).

Example 8

Preparation of N-Boc-Thiourea (Intermediate VII)

To a solution of thiourea (5.5 g, 72.3 mmol) in THF (500 mL) at 0° C. was added NaH (6.75 g, 60% dispersion, 168.8 mmol) in portions. The mixture was stirred at 0° C. for 10 min and subsequently treated dropwise with a solution of Boc$_2$O (16.5 g, 77.1 mmol) in THF (100 mL). The resulting thick suspension was thoroughly stirred and was allowed to reach room temperature and stirred for 1 additional hour. The reaction mixture was poured into dichloromethane (500 mL) and was partitioned with saturated NaHCO$_3$, followed by water and finally brine. The organic phase was dried over Na$_2$SO$_4$, filtered, and the volatiles were evaporated in vacuo. The residue was washed with heptane (2×100 mL) and pentane (100 mL) to afford 9.3 g of a white solid (mixture of mono and bis-Boc-thiourea 3:1).

Example 9

Preparation of N-Boc-4-(chloromethyl)thiazol-2-amine (Intermediate VIII)

To a solution of Intermediate VII (3.0 g, 17 mmol) in acetone (75 mL) was added 1,3-dichloroacetone (2.4 g, 18.7 mmol) at once. The mixture was stirred at room temperature for 72 h. The reaction mixture was treated with NaHCO$_3$ (3 g) and stirred for 15 min. The solids were removed by filtration and the filtrate was concentrated in vacuo. Column chromatography (EtOAc/Heptane, 4/1) afforded N-Boc-4-(chloromethyl)thiazol-2-amine (2.9 g, 11.6 mmol, 68%) as a white solid.

Example 10

Preparation of Ether Intermediates

To a suspension of NaH (3 eq.) in THF at 0° C. was added the alcohol (3 eq.) and 15-crown-5. The mixture was stirred at 0° C. for 30 min and N-Boc-4-(chloromethyl)thiazol-2-amine (1 eq.) was added. The mixture was allowed to reach room temperature and stirred overnight. The reaction was quenched upon addition of water. The product was extracted with EtOAc. The combined extracts were partitioned with brine, and then dried over Na$_2$SO$_4$, filtered and concentrated in vacuo. Purification by column chromatography (EtOAc/Heptane, 2/1) afforded the N-Boc-4-(alkoxymethyl)thiazol-2-amine derivatives.

Alternatively, the alkylation was performed by heating a solution of N-Boc-4-(chloromethyl)thiazol-2-amine in the alcohol in the presence of K$_2$CO$_3$ at 70° C.-80° C. for 2 hours. This method does however give lower yields for the alkoxyethoxy derivatives. Workup involves filtration and evaporation of the volatiles. Purification was achieved by column chromatography (EtOAc/Heptane, 2/1).

Intermediates IX-XIV (Examples 11-16) were prepared by the method described in Example 10.

Example 11 tert-Butyl 4-(n-butoxymethyl)thiazol-2-ylcarbamate (Intermediate IX)

Purification by column chromatography was not needed. $^1$H-NMR (300 MHz, CDCl$_3$): δ 6.55 (s, 1H), 4.28 (s, 2H), 3.24 (t, 2H), 1.5-1.1 (m, 4H), 1.40 (s, 9H) 0.80 (t, 3H).

Example 12 tert-Butyl 4-((2-phenoxyethoxy)methyl)thiazol-2-ylcarbamate (Intermediate X)

Purified by column chromatography (EtOAc/Heptane, 2/1), yield 23%. $^1$H-NMR (300 MHz, CDCl$_3$): δ 7.30 (m, 2H), 6.98 (t, 1H), 6.93 (d, 2H), 6.78 (s, 1H), 3.95 (m, 2H), 3.68 (m, 2H), 1.40 (s, 9H).

Example 13 tert-Butyl 4-((2-methoxypropoxy)methyl)thiazol-2-ylcarbamate (Intermediate XI)

Purification by column chromatography was not needed. $^1$H-NMR (300 MHz, CDCl$_3$): δ 6.70 (s, 1H), 4.40 (s, 2H), 3.55 (m, 2H), 3.43 (m, 2H), 3.28 (s, 3H), 1.80 (m, 2H), 1.40 (s, 9H).

Example 14 tert-Butyl 4-((2-ethoxyethoxy)methyl)thiazol-2-yl-carbamate (Intermediate XII)

960 mg of the crude compound was purified by column chromatography (SiO$_2$; Heptane/EtOAc, 1:1; R$_f$: 0.25) affording 160 mg (0.53 mmol; 13%). $^1$H NMR (300 MHz, CDCl$_3$): δ 6.8 (s, 1H); 4.58 (s, 2H); 3.68-3.58 (m, 4H); 3.58-3.45 (q, 2H); 1.5 (s, 9H), 1.2 (t, 3H).

Example 15 tert-Butyl 4-((2-(dimethylamino)ethoxy)methyl)thiazol-2-ylcarbamate (Intermediate XIII)

840 mg of crude material was purified by column chromatography (SiO$_2$; CH$_2$Cl$_2$/MeOH (3.5 M NH$_3$), 94:6; R$_f$: 0.25). 400 mg (1.33 mmol; 33%). $^1$H NMR (300 MHz, CDCl$_3$): δ 6.8 (s, 1H); 4.5 (s, 2H); 3.61 (t, 2H); 2.58 (t, 2H); 2.25 (s, 6H); 1.55 (s, 9H).

Example 16 tert-Butyl 4-((2-(methylthio)ethoxy)methyl)thiazol-2-ylcarbamate (Intermediate XIV)

1.96 g of the crude material was purified by column chromatography (SiO$_2$; Heptane/EtOAc, 75:25; R$_f$: 0.3) to afford 600 mg (1.97 mmol; 49%) of the product. $^1$H NMR (300 MHz, CDCl$_3$): δ 6.8 (s, 1H); 4.58 (s, 2H); 3.7 (t, 2H); 2.7 (t, 2H); 2.12 (s, 3H); 1.55 (s, 9H).

Example 17 tert-Butyl 4-((2-(methylsulfonyl)ethoxy)methyl)thiazol-2-ylcarbamate (Intermediate XV)

tert-Butyl 4-((2-(methylthio)ethoxy)methyl)thiazol-2-ylcarbamate (Example 16) (270 mg; 0.89 mmol) was dissolved in CH$_2$Cl$_2$ (15 mL). mCPBA (75% pure; 418 mg; 1.82 mmol) was added and the solution was stirred at room temperature for 1.5 hour. NaHCO$_3$ (saturated 20 mL) was added and the phases were separated. The aqueous layer was extracted with CH$_2$Cl$_2$ (10 mL). The organic extracts were dried with Na$_2$SO$_4$, filtered and concentrated in vacuo. 370 mg of crude compound was obtained which was then purified by column chromatography (SiO$_2$; Heptane/EtOAc, 34:66; R$_f$: 0.4) 270 mg (0.80 mmol; 66%). $^1$H-NMR (300 MHz, CDCl$_3$): δ 9.4 (bs, 1H); 6.8 (s, 1H); 4.55 (s, 2H); 3.95 (t, 2H); 3.22 (t, 2H); 2.98 (s, 3H); 1.58 (s, 9H).

Example 18

Method A

Preparation of Ureas Via Isocyanate

An N-Boc-4-(substituted) thiazol-2-amine (1 meq) was first dissolved in 1,4-dioxane then treated with HCl (4 N in dioxane) overnight. The resulting mixture was concentrated in vacuo and water was removed by azeotroping with toluene (2 times) to afford the corresponding free amine. This material was suspended in dichloromethane (or THF) and triethylamine or DIPEA (2.2 eq.) was added. To this mixture was added a benzylisocyanate (1.04 eq.). The mixture was stirred for 16-72 h at ambient temperature and the volatiles were removed in vacuo. The product was purified by column chromatography (DCM/2-5% MeOH) and, if needed, by an additional preparative HPLC run (Reversed Phase, water/acetonitrile).

The compounds of Examples 19-39 were prepared using Method A outlined in Example 18 starting with purchased intermediates or from the corresponding intermediates described in Examples 11-17.

Example 19

1-(3,4-Dichlorobenzyl)-3-(4-(methoxymethyl)thiazol-2-yl)urea

The crude material was purified by preparative HPLC to give 20% (72 mg, 208 μmol) of the title compound. $^1$H NMR (300 MHz, CDCl$_3$) δ 3.15 (s, 3H), 4.38-4.42 (m, 4H), 6.77 (s, 1H), 7.15 (d, 2H), 7.35-7.40 (m, 2H), 7.45 (s, br, 1H). MS (ES+): M/Z 346 and 348 (M+H).

Example 20

1-(3,4-Dichlorobenzyl)-3-(4-((2-methoxyethoxy)methyl)thiazol-2-yl)urea

The crude material was first purified by column chromatography (silica gel, ethyl acetate/heptane, 3:1, 5:1, 7:1, 10:1, 15:1) and then by a radial chromatography (silica gel, ethyl acetate/heptane 5:1, 10:1, 15:1, 20:1). The obtained tan coloured solid was triturated with diethyl ether/methanol, yielding 20% (31 mg, 79 μmol) of the title compound as a white solid. $^1$H NMR (300 MHz, CDCl$_3$) δ 3.21 (s, 3H), 3.36-3.40 (m, 2H), 3.47-3.50 (m, 2H), 4.41 (d, 2H), 4.47 (s, 2H), 6.74 (s, 1H), 7.20 (dd, 1H), 7.38 (d, 1H), 7.45 (d, 1H), 7.68 (br s, 1H). MS (ES+): M/Z 390 and 392 (M+H).

Example 21

1-(3,4-Dichlorobenzyl)-3-(4-(butoxymethyl)thiazol-2-yl)urea

Purified by preparative HPLC, 8% yield. $^1$H-NMR (300 MHz, CDCl$_3$): δ 11.50 (bs, 1H), 7.95 (bs 1H), 7.40 (d, 1H), 7.37 (s, 1H), 7.18 (d, 1H), 6.75 (s, 1H), 4.43 (s, 2H), 4.39 (s, 2H), 3.30 (t, 2H), 1.40-1.10 (m, 4H), 0.78 (t, 3H).

Example 22

1-(3,4-Dichlorobenzyl)-3-(4-((2-phenoxyethoxy)methyl)thiazol-2-yl)urea

Purified by preparative HPLC, 6% yield. $^1$H-NMR (300 MHz, CDCl$_3$): δ 7.70 (bs 1H), 7.37 (s, 1H), 7.24 (m, 2H), 7.05 (d, 1H), 6.92 (t, 1H), 6.75 (m, 3H), 4.53 (s, 2H), 4.35 (d, 2H), 3.95 (m, 2H), 3.69 (m, 2H).

Example 23

1-(3,4-Dichlorobenzyl)-3-(4-((3-methoxypropoxy)methyl)thiazol-2-yl)urea

Purified by preparative HPLC, 5% yield. $^1$H-NMR (ppm, CDCl$_3$): δ 7.65 (bs 1H), 7.40 (d, 1H), 7.37 (s, 1H), 7.15 (d, 1H), 6.72 (s, 1H), 4.42 (s, 2H), 4.40 (s, 2H), 3.42 (t, 2H), 3.30 (t, 2H), 3.25 (s, 3H), 1.67 (m, 2H).

Example 24

1-(3,4-Dichlorobenzyl)-3-(4-((2-ethoxyethoxy)methyl)thiazol-2-yl)urea

Crude yield: 300 mg. Purified by column (SiO$_2$; Heptane.EtOAc 75:25 R$_f$: 0.2). Product containing fractions combined and purified by preparative HPLC (20 mg; 0.05 mmol; 6%). $^1$H NMR (300 MHz, CDCl$_3$): δ 11.3 (bs, 1H), 7.75 (bs, 1H), 7.45 (d, 1H), 7.38 (d, 1H), 7.2 (dd, 1H), 6.75 (s, 1H), 4.50-4.35 (m, 4H), 3.54-3.32 (m, 6H), 1.12 (t, 3H).

Example 25

1-(3,4-Dichlorobenzyl)-3-(4-((2-(dimethylamino)ethoxy)methyl)thiazol-2-yl)urea

Purified by column (SiO$_2$; Heptane/EtOAc 80:20; R$_f$: 0.3). The product containing fractions were combined and evaporated to dryness. The compound was further purified by preparative HPLC. 110 mg (0.27 mmol; 19%). $^1$H NMR (300 MHz, CDCl$_3$): δ 7.78 (bs, 1H), 7.42 (d, 1H), 7.35 (d, 1H), 7.16 (dd, 1H), 6.72 (s, 1H), 4.44-4.36 (m, 4H), 3.42 (t, 2H), 2.32 (t, 2H), 2.12 (s, 6H).

Example 26

1-(3,4-Dichlorobenzyl)-3-(4-((2-(methylthio)ethoxy)methyl)thiazol-2-yl)urea

Filtered over SiO$_2$ (Heptane:EtOAc 90:10; R$_f$: 0.3). 200 mg material further purified by preparative HPLC (30 mg; 0.07 mmol; 7%). $^1$H NMR (ppm, CDCl$_3$) δ 11.32 (bs, 1H), 7.62 (bs, 1H), 7.45 (d, 1H), 7.4 (d, 1H), 7.18 (dd, 1H), 6.78 (s, 1H), 4.45 (s, 4H), 3.5 (t, 2H), 2.5 (t, 2H), 2.0 (s, 3H).

Example 27

1-(3,4-Dichloro-benzyl)-3-[4-(2-methanesulfinyl-ethoxymethyl)-thiazol-2-yl]-urea 1-(3,4-Dichlorobenzyl)-3-(4-((2-(methylthio)ethoxy)methyl)thiazol-2-yl)urea (Example 26) (0.98 mmol, 0.4 g) was dissolved in CHCl$_3$ (10 mL) and cooled to 0° C. 3-Chloroperbenzoic acid (1 eq, 0.98 mmol, 0.17 g) was added and the mixture was stirred at room temperature overnight. LC-MS indicated the product was a mixture of sulfoxide and sulfone. Sodium bicarbonate (saturated, 10 mL) was added and the phases were separated. The aqueous phase was extracted with $CH_2Cl_2$ (2×20 mL). The combined organic layers were dried ($Na_2SO_4$), filtered, and concentrated to give an oil. Purification by preparative HPLC yielded 0.048 g of the title compound as a white solid. $^1$H NMR (300 MHz, $CD_3OD$): δ 7.49-7.45 (m, 2H), 7.25 (m, 1H), 6.85 (s, 1H), 4.87 (s, 2H), 4.45 (s, 2H), 3.86 (m, 2H), 3.11-2.91 (m, 2H), 2.65 (s, 3H).

Example 28

1-(3,4-Dichlorobenzyl)-3-(4-((2-(methylsulfonyl) ethoxy)methyl)thiazol-2-yl)urea Purified by column ($SiO_2$; Heptane; EtOAc, 75:25; $R_f$: 0.25). Product containing fractions purified by HPLC (reversed phase; gradient water/methanol 75 mg (0.17 mmol; 18%). $^1$H NMR (ppm, $CDCl_3$) δ 10.12 (bs, 1H), 7.42-7.32 (m, 2H), 7.15 (dd, 1H), 6.75 (s, 1H), 4.5 (s, 2H), 4.42 (d, 2H), 3.95 (t, 2H), 3.22 (t, 2H), 2.95 (s, 3H).

Example 29

1-(3-Fluoro-benzyl)-3-[4-(2-methoxy-ethoxymethyl)-thiazol-2-yl]-urea $^1$H NMR (300 MHz, $CDCl_3$): δ 11.15 (br s, 1H), 7.65 (br s, 1H), 7.23 (m, 1H), 7.10-7.00 (m, 2H), 6.91 (m, 1H), 6.68 (s, 1H), 4.46 (s, 2H), 4.40 (s, 2H), 3.49 (m, 2H), 3.38 (m, 2H), 3.21 (s, 3H). MS (ES+): M/Z 340 (M+1).

Example 30

1-[4-(2-tert-Butoxy-ethoxymethyl)-thiazol-2-yl]-3-(3,4-dichloro-benzyl)-urea

The compound was purified by column chromatography (using 0-40% B gradient: A: hexanes, B: 10% MeOH/Ethyl acetate). $^1$H NMR (300 MHz, $CD_3OD$) δ 7.47 (s, 1H), 7.45 (d, 1H), 7.24 (d, 1H), 6.87 (s, 1H), 4.47 (s, 2H), 4.40 (s, 2H), 3.59 (m, 2H), 3.54 (m, 2H), 1.18 (s, 9H).

Example 31

1-(3,4-Dichloro-benzyl)-3-[4-(2-hydroxy-ethoxymethyl)-thiazol-2-yl]-urea

The t-butyl ether Example 30 was treated with trifluoroacetic acid at room temperature overnight and the solvent was removed by evaporation and the product was triturated in ether to afford the title compound. $^1$H NMR (300 MHz, $CD_3OD$) δ 7.49 (s, 1H), 7.46 (d, 1H), 7.25 (d, 1H), 7.15 (s, 1H), 4.54 (s, 2H), 4.42 (s, 2H), 3.68 (m, 2H), 3.59 (m, 2H).

Example 32

1-(3,4-Dichloro-benzyl)-3-(4-phenoxymethyl-thiazol-2-yl)-urea $^1$H NMR (400 MHz, DMSO-$d_6$): δ 10.69 (br s, 1H), 7.57 (d, 1H), 7.52 (d, 1H), 7.29-7.23 (m, 3H), 7.11 (br t, 1H), 7.02-6.96 (m, 3H), 6.91 (t, 1H), 4.96, (s, 2H), 4.30 (d, 2H). MS (ES+): M/Z 408 and 410 (M+1).

Example 33

1-(3-Fluoro-benzyl)-3-[4-(2-methanesulfonyl-ethoxymethyl)-thiazol-2-yl]-urea $^1$H NMR (400 MHz, $CD_3OD$): δ 7.34 (m, 1H), 7.14 (d, 1H), 7.06 (m, 1H), 6.98 (m, 1H), 6.92 (s, 1H), 4.49 (s, 2H), 4.43 (s, 2H), 3.91 (t, 2H), 3.34 (t, 2H), 2.99 (s, 3H). MS (ES+): M/Z 388 (M+1).

Example 34

Acetic acid 5-{2-[3-(3,4-dichloro-benzyl)-ureido]-thiazol-4-yl}-pyrrolidin-3-yl ester hydrochloride salt Step 1: 4-Acetoxy-2-{2-[3-(3,4-dichloro-benzyl)-ureido]-thiazol-4-yl}-pyrrolidine-1-carboxylic acid tert-butyl ester was prepared via the isocyanate, see Method A in Example 18.

Step 2: The protecting group was removed by treating the 4-Acetoxy-2-{2-[3-(3,4-dichloro-benzyl)-ureido]-thiazol-4-yl}-pyrrolidine-1-carboxylic acid tert-butyl ester with a 4.0 M solution of HCl in dioxane. The reaction was stirred overnight and volatiles were removed in vacuo. The crude material was taken up in minimal tetrahydrofuran and ether was added to precipitate the product. $^1$H-NMR (400 MHz, DMSO-$d_6$): δ 10.88 (s, 1H), 10.10 (br s, 1H), 9.10 (br s, 1H), 7.58 (d, 1H), 7.53-7.46 (m, 2H), 7.26 (dd, 1H), 7.18 (s, 1H), 5.39 (m, 1H), 4.76 (m, 1H), 4.32 (d, 2H), 3.55 (m, 2H) 2.40 (m, 2H), 2.03 (s, 3H). MS (ES+): M/Z 429 and 431 (M+1).

Example 35

Ethyl 2-(2-(3-(3,4-dichlorobenzyl)ureido)thiazol-4-yl)acetate $^1$H NMR (300 MHz, $CDCl_3$) δ 1.19 (t, 3H), 3.58 (s, 2H), 3.97 (q, 2H), 4.33 (d, 2H), 6.60 (s, 1H), 7.11 (dd, 1H), 7.33-7.37 (m, 2H), 10.40 (s, br, 1H). MS (ES+): M/Z 388 and 390 (M+H).

Example 36

1-(3,4-Dichlorobenzyl)-3-(4-(2-hydroxyethyl)thiazol-2-yl)urea

Lithium boranate (7 mg, 322 µmol) was added to a solution of Ethyl 2-(2-(3-(3,4-dichlorobenzyl)ureido)thiazol-4-yl)acetate (Example 35) (58 mg, 150 µmol) in dry THF (4 ml) at 0° C. The reaction mixture was stirred for 3 hours at this temperature and then allowed to warm to ambient temperature overnight. Then, saturated aqueous ammonium chloride solution (3 ml) was added and the mixture was stirred for 2 hours. The salts were dissolved by addition of a few drops of water, and the mixture was extracted several times with ethyl acetate. The combined organic layers were partitioned with brine and then dried over sodium sulfate, filtered, and volatiles removed in vacuo. The crude material was purified by column chromatography (silica gel, acetone/ethyl acetate, 1:20, 1:15, 1:10), yielding the title compound in 60% (32 mg, 92 mmol). $^1$H NMR (300 MHz, $CD_3OD$) δ 2.80 (t, 2H), 3.81 (t, 2H), 4.40 (s, 2H), 6.60 (s, 1H), 7.24 (dd, 1H), 7.42-7.48 (m, 2H). MS (ES+): M/Z 346 and 348 (M+H).

Example 37

1-(3-fluorobenzyl)-3-(4-(2-hydroxyethyl)thiazol-2-yl)urea

Step 1: Ethyl 2-(2-(3-(3-fluorobenzyl)ureido)thiazol-4-yl)acetate was prepared via method A described in Example 18.

Step 2: Lithium aluminum hydride (10.6 µL, 10.6 mmol, 1M in THF) was added dropwise to a THF (50 mL) solution of ethyl 2-(2-(3-(3-fluorobenzyl)ureido)thiazol-4-yl)acetate (1.32 g, 4.1 mmol) at −78° C. The reaction was allowed to slowly warm to ambient temperature. The mixture was stirred at ambient temperature until completion of the reaction. Sodium sulfate decahydrate (3.2 g, 10 mmol) was added carefully. It was followed by the addition of sodium bisulfate (1.8 g) and the mixture was stirred for 30 hours. An aqueous work-up with EtOAc and a recrystallization from a mixture of $CH_2Cl_2$ and hexane afforded the pure title compound. $^1$H NMR (400 MHz, $CDCl_3$): δ 9.5 (s, 1H, br), 7.75 (s, 1H, br), 7.27 (m, 1H), 7.07 (d, 1H), 7.01 (d, 1H), 7.94 (td, 1H), 6.48 (s, 1H), 4.48 (d, 2H), 3.83 (t, 2H), 2.83 (t, 2H). MS (ES+): M/Z 338 $(M+H)^+$.

Example 38

Ethyl 2-(3-(3,4-dichlorobenzyl)ureido)thiazole-4-carboxylate

25% yield (290 mg, 775 µmol). $^1$H NMR (300 MHz, $d_6$-DMSO) δ 1.19 (t, 3H), 4.14 (q, 2H), 4.39 (d, 2H), 7.22 (dd, 1H), 7.47 (d, 1H), 7.52 (d, 1H), 7.68 (s, 1H), 8.72 (s, br, 1H). MS (ES+): M/Z 374 and 376 (M+H).

Example 39

1-(3,4-Dichlorobenzyl)-3-(4-(hydroxymethyl)thiazol-2-yl)urea

To a suspension of Ethyl 2-(3-(3,4-dichlorobenzyl)ureido)thiazole-4-carboxylate Example 38 (172 mg, 460 µmol) in THF (8 ml) was added a solution of lithium boronate/THF (1 M, 0.7 ml, 700 µmol) at 0° C. Stirring was continued at 0° C. for 2 hours. After this time, TLC indicated complete conversion and to the reaction mixture was added sodium sulfate decahydrate (1.20 g, 3.72 mmol). While warming up to ambient temperature, the mixture was stirred for further 20 minutes. The solids were removed by filtration and the solvent was removed under reduced pressure. The crude material was purified by column chromatography (silica gel, ethyl acetate, methanol/ethyl acetate 1:40, 1:30, 1:20, 1:15), yielding the desired compound in 75% (115 mg, 346 µmol) as a white solid. $^1$H NMR (300 MHz, $d_6$-DMSO) δ 4.32 (d, 2H), 4.37 (d, 2H), 5.10 (t, br, 1H), 6.71 (s, 1H), 7.18 (t, br, 1H), 7.27 (dd, 1H), 7.51 (d, 1H), 7.59 (d, 1H), 10.53 (s, br, 1H). MS (ES+): M/Z 332 and 334 (M+H).

Example 40

Preparation of 4-{[(2-Methoxy-ethyl)-methyl-amino]-methyl}-thiazol-2-ylamine (Intermediate XVI)

4-(chloromethyl)thiazol-2-amine hydrochloride (Intermediate I) (1 meq) was suspended in THF (20 ml) and DIEA (2 eq.) was added followed by addition of N-methyl-methoxy-ethylamine (1 eq.). The reaction was heated at reflux overnight. The reaction was concentrated by evaporation to solid residue.

Example 41

Preparation of (4-{[(2-Methoxy-ethyl)-methyl-amino]-methyl}-thiazol-2-yl)-carbamic acid phenyl ester (Intermediate XVII)

To the 4-{[(2-Methoxy-ethyl)-methyl-amino]-methyl}-thiazol-2-ylamine prepared in Example 40, pyridine (20 ml) was added followed by addition of DMAP (0.05-0.01 meq.) and phenylchlorofomate (1.10 meq.). The reaction was stirred at room temperature overnight. The solvent was removed by evaporation and the residue was purified by column chromatography using 10% saturated ammonia/MeOH in dichloromethane.

Example 42

Preparation of [4-(2-Methoxy-ethoxymethyl)-thiazol-2-yl]-carbamic acid phenyl ester (Intermediate XVIII)

tert-butyl 4-((2-methoxyethoxy)methyl)thiazol-2-ylcarbamate (Intermediate III, 3.4 g, 0.018 mol) was dissolved in pyridine (50 mL) and a catalytic amount of DMAP was added (0.2 g, ~10 mol %). To this mixture a solution of phenyl chloroformate (2.27 mL, 1 eq.) in THF (50 mL) was added drop wise and the resulting reaction mixture was stirred for 3 hours at ambient temperature. Then, $H_2O$ was added and the diluted mixture was extracted with EtOAc. Dried the organic layer over $Na_2SO_4$, filtered and concentrated in vacuo. Purification over $SiO_2$ eluting with 1:1 EtOAc/heptane gave 2.4 gram of the product as a yellow fluffy solid. $^1$H-NMR (300 MHz, DMSO-$d_6$) δ 11.70 (s, br, 1H), 7.42 (d, 1H), 7.37 (m, 1H), 7.08 (m, 3H), 4.59 (s, 2H), 4.38 (d, 2H), 3.30 (s, 2H), 3.23 (t, 2H), 1.75 (q, 2H), 0.97 (t, 3H).

Example 43

Preparation of [4-(2-Methanesulfonyl-ethoxymethyl)-thiazol-2-yl]-carbamic acid phenyl ester (Intermediate XIX)

Prepared from tert-Butyl 4-((2-(methylsulfonyl)ethoxy)methyl)thiazol-2-ylcarbamate (Intermediate XV) in the same manner as described in Example 42.

Example 44

Method B

Preparation of Ureas Via Phenylcarbamates

A phenylcarbamate (1 meq.) was taken up in dioxane and benzyl amine (1.1 meq.) was added. The reaction was heated in the microwave for five minutes at 140° C. The solvent was removed and the crude material was purified by column chromatography using 10% saturated ammonia/MeOH in dichloromethane or ethyl acetate to give product. In some cases, the HCl salt of the product was prepared. The compound was taken up in minimal MeOH and HCl in dioxane was added. The addition of diethyl ether to the dioxane/HCl solution precipitated product as a white solid. The product was isolated as the HCl salt.

The compounds described in Examples 45-71 were prepared using Method B outlined in Example 44 starting with the corresponding intermediate described in Examples 41-43.

Example 45

1-(3-Bromo-benzyl)-3-(4-{[(2-methoxy-ethyl)-methyl-amino]-methyl}-thiazol-2-yl)-urea hydrochloride $^1$H NMR (400 MHz, CD$_3$OD): δ 7.49 (s, 1H), 7.41 (d, 1H), 7.32-7.22 (m, 2H), 7.21 (s, 1H), 4.41 (s, 2H), 4.30 (m, 2H), 3.72 (m, 2H), 3.40 (s, 3H), 2.88 (s, 3H). MS (ES+): M/Z 413 and 415 (M+1).

Example 46

1-(3-Chloro-benzyl)-3-(4-{[(2-methoxy-ethyl)-methyl-amino]-methyl}-thiazol-2-yl)-urea hydrochloride $^1$H NMR (400 MHz, CD$_3$OD): δ 7.33 (s, 1H), 7.31 (d, 1H), 7.28-7.22 (m, 2H), 7.20 (s, 1H), 4.42 (s, 2H), 4.30 (m, 2H), 3.71 (m, 2H), 3.40 (s, 3H), 2.88 (s, 3H). MS (ES+): M/Z 369 (M+1).

Example 47

1-(3-Fluoro-benzyl)-3-(4-{[(2-methoxy-ethyl)-methyl-amino]-methyl}-thiazol-2-yl)-urea hydrochloride $^1$H NMR (400 MHz, CD$_3$OD): δ 7.33 (m, 1H), 7.21 (s, 1H), 7.14 (d, 1H), 7.06 (d, 1H), 6.98 (m, 1H), 4.44 (s, 2H), 4.31 (m, 2H), 3.72 (m, 2H), 3.40 (s, 3H), 2.88 (s, 3H). MS (ES+): M/Z 353 (M+1).

Example 48

1-(3-Chloro-4-fluoro-benzyl)-3-(4-{[(2-methoxy-ethyl)-methyl-amino]-methyl}-thiazol-2-yl)-urea hydrochloride salt $^1$H NMR (400 MHz, CD$_3$OD): δ 7.44 (dd, 1H), 7.29 (m, 1H), 7.22-7.17 (m, 2H), 4.40 (s, 2H), 4.31 (m, 2H), 3.72 (t, 2H), 3.46 (br m, 2H), 3.40 (s, 3H), 2.88 (s, 3H). MS (ES+): M/Z 387 (M+1).

Example 49

1-(3,4-Dimethyl-benzyl)-3-[4-(2-methoxy-ethoxymethyl)-thiazol-2-yl]-urea $^1$H NMR (400 MHz, CD$_3$OD): δ 7.09-7.05 (m, 2H), 7.01 (d, 1H), 6.86 (s, 1H), 4.45 (s, 2H), 4.34 (s, 2H), 3.62 (m, 2H), 3.53 (m, 2H), 3.34 (s, 3H), 2.24 (s, 3H), 2.22 (s, 3H). MS (ES+): M/Z 350 (M+1).

Example 50

1-(3-Bromo-benzyl)-3-[4-(2-methoxy-ethoxymethyl)-thiazol-2-yl]-urea $^1$H NMR (400 MHz, CD$_3$OD): δ 7.49 (s, 1H), 7.40 (d, 1H), 7.32-7.21 (m, 2H), 6.88 (s, 1H), 4.47 (s, 2H), 4.41 (s, 2H), 3.64 (m, 2H), 3.54 (m, 2H), 3.34 (s, 3H). MS (ES+): M/Z 400 and 402 (M+1).

Example 51

1-(4-Chloro-3-trifluoromethyl-benzyl)-3-[4-(2-methoxy-ethoxymethyl)-thiazol-2-yl]-urea $^1$H NMR (400 MHz, CD$_3$OD): δ 7.73 (s, 1H), 7.57 (s, 2H), 6.88 (s, 1H), 4.47 (s, 4H), 3.63 (m, 2H), 3.54 (m, 2H), 3.34 (s, 3H). MS (ES+): M/Z 424 (M+1).

Example 52

1-Benzo[1,3]dioxol-5-ylmethyl-3-[4-(2-methoxy-ethoxymethyl)-thiazol-2-yl]-urea $^1$H NMR (400 MHz, CD$_3$OD): δ 6.90-6.74 (m, 3H), 5.91 (s, 1H), 4.46 (s, 2H), 4.32 (s, 2H), 3.63 (m, 2H), 3.54 (m, 2H), 3.34 (s, 3H). MS (ES+): M/Z 366 (M+1).

Example 53

1-(3-Chloro-4-fluoro-benzyl)-3-[4-(2-methoxy-ethoxymethyl)-thiazol-2-yl]-urea $^1$H NMR (400 MHz, CD$_3$OD): δ 7.44 (d, 1H), 7.28 (m, 1H), 7.19 (m, 1H), 6.88 (s, 1H), 4.46 (s, 2H), 4.39 (s, 2H), 3.63 (m, 2H), 3.54 (m, 2H), 3.34 (s, 3H). MS (ES+): M/Z 374 (M+1).

Example 54

1-(3-Chloro-benzyl)-3-[4-(2-methoxy-ethoxymethyl)-thiazol-2-yl]-urea $^1$H NMR (400 MHz, CD$_3$OD): δ 7.34 (s, 1H), 7.30 (d, 1H), 7.27-7.23 (m, 2H), 6.88 (s, 1H), 4.47 (s, 2H), 4.42 (s, 2H), 3.64 (m, 2H), 3.54 (m, 2H), 3.34 (s, 3H). MS (ES+): M/Z 356 (M+1).

Example 55

1-(3-Iodo-benzyl)-3-[4-(2-methoxy-ethoxymethyl)-thiazol-2-yl]-urea $^1$H NMR (400 MHz, CD$_3$OD): δ 7.70 (s, 1H), 7.61 (d, 1H), 7.33 (d, 1H), 7.10 (t, 1H), 6.88 (s, 1H), 4.47 (s, 2H), 4.38 (s, 2H), 3.63 (m, 2H), 3.54 (m, 2H), 3.34 (s, 3H). MS (ES+): M/Z 448 (M+1).

Example 56

1-(4-bromobenzyl)-3-(4-((2-methoxyethoxy)methyl)thiazol-2-yl)urea $^1$H NMR (400 MHz, CD$_3$OD): δ 7.46 (d, 2H), 7.24 (d, 2H), 6.87 (s, 1H), 4.45 (s, 2H), 4.39 (s, 2H), 3.63 (m, 2H), 3.54 (m, 2H), 3.34 (s, 3H), MS (ES+): M/Z 402 (M+1).

Example 57

1-(1-(4-bromophenyl)ethyl)-3-(4-((2-methoxyethoxy)methyl)thiazol-2-yl)urea $^1$H NMR (400 MHz, CD$_3$OD): δ 7.48 (d, 2H), 7.27 (d, 2H), 6.85 (s, 1H), 4.84 (m, 1H), 4.45 (s, 2H), 3.63 (m, 2H), 3.55 (m, 2H), 3.35 (s, 3H), 1.49 (d, 3H). MS (ES+): M/Z 416 (M+1).

Example 58

1-(4-Chloro-3-fluoro-benzyl)-3-[4-(2-methoxy-ethoxymethyl)-thiazol-2-yl]-urea $^1$H NMR (400 MHz, CD$_3$OD): δ 7.42 (t, 1H), 7.21 (dd, 1H), 7.14 (d, 1H), 6.88 (s, 1H), 4.47 (s, 2H), 4.42 (s, 2H), 3.64 (m, 2H), 3.55 (m, 2H), 3.31 (s, 3H). MS (ES+): M/Z 374 (M+1).

Example 59

1-(3-Bromo-4-chloro-benzyl)-3-[4-(2-methoxy-ethoxymethyl)-thiazol-2-yl]-urea $^1$H NMR (400 MHz, CDCl$_3$): δ 7.62 (d, 1H), 7.38 (d, 1H), 7.25 (m, 1H), 6.75 (s, 1H), 4.47 (s, 2H), 4.42 (d, 2H), 3.51 (m, 2H), 3.38 (m, 2H), 3.23 (s, 3H). MS (ES+): M/Z 434 and 436 (M+1).

Example 60

1-(3,5-Difluoro-benzyl)-3-[4-(2-methoxy-ethoxymethyl)-thiazol-2-yl]-urea $^1$H NMR (400 MHz, CD$_3$OD): δ 6.96-6.90 (m, 2H), 6.89 (s, 1H), 6.82 (m, 1H), 4.47 (s, 2H), 4.43 (s, 2H), 3.65 (m, 2H), 3.56 (m, 2H), 3.31 (s, 3H). MS (ES+): M/Z 358 (M+1).

Example 61

1-[4-(2-Methoxy-ethoxymethyl)-thiazol-2-yl]-3-(3,4,5-trifluoro-benzyl)-urea $^1$H NMR (400 MHz, DMSO): δ 7.27-7.20 (m, 2H), 7.13 (br m, 1H), 6.87 (s, 1H), 4.38 (s, 2H), 4.31 (d, 2H), 3.75 (m, 2H), 3.46 (m, 2H), 3.24 (s, 3H). MS (ES+): M/Z 376 (M+1).

Example 62

1-(4,5-Dibromo-thiophen-2-ylmethyl)-3-[4-(2-methoxy-ethoxymethyl)-thiazol-2-yl]-urea Step 1: Prepare protected amine. The substituted-thiophene aldehyde (10 mmol) was mixed with 2,4-dimethoxybenzylamine (1.0 equivalent) in dichloromethane (20 ml). Acetic acid (1 ml) was added to the mixture followed by addition of sodium triacetoxyborohydride (2.5 equivalents). The reaction was stirred at ambient temperature overnight. The mixture was filtered and extracted with dichloromethane and concentrated in vacuo, then purified by column chromatography using 0-100% gradient of 10% MeOH/EtOAc and hexanes to give (4,5-Dibromo-thiophen-2-ylmethyl)-(2,4-dimethoxy-benzyl)-amine.

Step 2: Follow general procedure Method B described in Example 44 using the (4,5-Dibromo-thiophen-2-ylmethyl)-(2,4-dimethoxy-benzyl)-amine prepared in Step 1.

Step 3: Deprotection: The 1-(4,5-Dibromo-thiophen-2-ylmethyl)-1-(2,4-dimethoxy-benzyl)-3-[4-(2-methoxy-ethoxymethyl)-thiazol-2-yl]-urea was treated with TFA followed by the addition of a drop of anisole and a drop of water. Stirred overnight at ambient temperature. The volatiles were removed in vacuo and the crude material was purified by taking up in MeOH and filtering to remove insolubles. The filtrate was concentrated in vacuo, and the resulting solid titrated with ether to give the title compound. $^1$H NMR (400 MHz, DMSO): δ 10.70 (br s, 1H), 7.17 (br m, 1H), 7.00 (s, 1H), 6.88 (s, 1H), 4.42 (d, 2H), 4.37 (s, 2H), 3.55 (m, 2H), 3.45 (m, 2H), 3.24 (s, 3H). MS (ES+): M/Z 484, 486 and 488 (M+1).

Example 63

1-(2,2-Difluoro-benzo[1,3]-dioxol-5-ylmethyl)-3-[4-(2-methoxy-ethoxymethyl)-thiazol-2-yl]-urea The title compound was prepared in three steps following the procedure outlined in example 62. An additional purification by column chromatography (hexanes/ethyl acetate with 10% MeOH) was performed on the crude solid. $^1$H NMR (400 MHz, CD$_3$OD): δ 7.19 9S, 1H), 7.15-7.13 (m, 2H), 6.89 (s, 1H), 4.47 (s, 2H), 4.43 (s, 2H), 3.64 (m, 2H), 3.54 (m, 2H), 3.31 (s, 3H). MS (ES+): M/Z 402 (M+1).

Example 64

1-(3-Chloro-5-fluoro-benzyl)-3-[4-(2-methoxy-ethoxymethyl)-thiazol-2-yl]-urea $^1$H NMR (400 MHz, CD$_3$OD): δ 7.99 (br m, 1H), 7.09 (m, 1H), 7.04 (m, 1H), 6.89 (s, 1H), 4.48 (s, 2H), 4.43 (s, 2H), 3.64 (m, 2H), 3.55 (m, 2H), 3.31 (s, 3H).

Example 65

1-[4-(2-Methoxy-ethoxymethyl)-thiazol-2-yl]-3-thiophen-3-ylmethyl-urea $^1$H NMR (400 MHz, DMSO): δ 10.40 (br s, 1H), 7.47 (m, 1H), 7.29 (m, 1H), 7.03 (dd, 1H), 6.92 (br m, 1H), 6.83 (s, 1H), 4.34 (s, 2H), 4.29 (d, 2H), 3.52 (m, 2H), 3.42 (m, 2H), 3.21 (s, 3H). MS (ES+): M/Z 328 (M+1).

Example 66

1-[4-(2-Methoxy-ethoxymethyl)-thiazol-2-yl]-3-thiophen-2-ylmethyl-urea $^1$H NMR (400 MHz, DMSO): δ 10.45 (br s, 1H), 7.37 (dd, 1H), 7.03 (br m, 1H), 6.97 (m, 1H), 6.94 (m, 1H), 6.84 (s, 1H), 4.47 (d, 2H), 4.34 (s, 2H), 3.52 (m, 2H), 3.42 (m, 2H), 3.21 (s, 3H). MS (ES+): M/Z 328 (M+1).

Example 67

1-(5-Bromo-thiophen-2-ylmethyl)-3-[4-(2-methoxy-ethoxymethyl)-thiazol-2-yl]-urea The title compound was prepared in three steps following the procedure outlined in Example 62. $^1$H NMR (400 MHz, CD$_3$OD): δ 6.94 (d, 1H), 6.88 (s, 1H), 6.81 (d, 1H), 4.51 (s, 2H), 4.47 (s, 2H), 3.63 (m, 2H), 3.55 (m, 2H), 3.34 (s, 3H). MS (ES+): M/Z 406 and 408 (M+1).

Example 68

1-(5-Chloro-thiophen-2-ylmethyl)-3-[4-(2-methoxy-ethoxymethyl)-thiazol-2-yl]-urea The title compound was prepared in three steps following the procedure outlined in Example 62. Additional purification by column chromatography (DCM/NH$_3$ saturated MeOH) was performed on the crude solid. $^1$H NMR (400 MHz, DMSO): δ 10.58 (br s, 1H), 7.11 (br m 1H), 6.95 (d, 1H), 6.88-6.85 (m, 2H), 4.42 (d, 2H), 4.37 (s, 2H), 3.56 (m, 2H), 3.45 (m, 2H), 3.24 (s, 3H). MS (ES+): M/Z 362 (M+1).

Example 69

1-(4-Fluoro-benzyl)-3-[4-(2-methoxy-ethoxymethyl)-thiazol-2-yl]-urea $^1$H NMR (400 MHz, DMSO): δ 10.50 (br s, 1H), 7.33 (m, 2H), 7.16 (m, 2H), 7.03 (br m, 1H), 6.86 (s, 1H), 4.37 (s, 2H), 4.31 (d, 2H), 3.56 (m, 2H), 3.45 (m, 2H), 3.24 (s, 3H). MS (ES+): M/Z 340 (M+1).

Example 70

1-(3-Chloro-benzyl)-3-[4-(2-methanesulfonyl-ethoxymethyl)-thiazol-2-yl]-urea $^1$H NMR (400 MHz, CD$_3$OD): δ 7.36-7.23 (m, 4H), 6.92 (s, 1H), 4.49 (s, 2H), 4.42 (s, 2H), 3.91 (t, 2H), 3.34 (t, 2H), 3.00 (s, 3H). MS (ES+): M/Z 404 (M+1).

Example 71

1-(3-Bromo-benzyl)-3-[4-(2-methanesulfonyl-ethoxymethyl)-thiazol-2-yl]-urea $^1$H NMR (400 MHz, DMSO): δ 10.60 (br s, 1H), 7.50-7.42 (m, 2H), 7.33-7.28 (m, 2H), 7.09 (br m, 1H), 6.93 (s, 1H), 4.42 (s, 2H), 4.34 (d, 2H), 3.82 (t, 2H), 3.38 (t, 2H), 2.99 (s, 3H). MS (ES+): M/Z 448 and 450 (M+1).

Example 72

Preparation of 1-(3,4-dichlorobenzyl)-3-(4-(chloromethyl)thiazol-2-yl)urea (Intermediate XX)

To a suspension of 4-(chloromethyl)thiazol-2-amine hydrochloride (7.55 g, 41 mmol) in dichloromethane (150 mL) at 0° C. was added 3,4-dichlorobenzyl isocyanate (8.27 g, 41 mmol). A solution of DIPEA in dichloromethane (30 mL) was added over a period of 30 min and the mixture was stirred overnight at room temperature. Evaporation of the volatiles in vacuo followed by purification by column chromatography (EtOAc/heptane 1/1) afforded 1-(3,4-dichlorobenzyl)-3-(4-(chloromethyl)thiazol-2-yl)urea as an off-white solid (10.5 g, 30 mmol) in 73% yield. $^1$H-NMR (ppm, DMSO-d$_6$): 10.80 (bs, 1H), 7.60 (d, 1H), 7.55 (s, 1H), 7.11 (t, 1H), 7.05 (s, 1H), 4.63 (s, 2H), 4.30 (d, 2H).

Example 73

Preparation of 1-(3-fluorobenzyl)-3-(4-(chloromethyl)thiazol-2-yl)urea (Intermediate XXI)

Prepared in a similar manner as 1-(3,4-dichlorobenzyl)-3-(4-(chloromethyl)thiazol-2-yl)urea (see Example 72). $^1$H-NMR (ppm, DMSO-d$_6$): 10.70 (bs, 1H), 7.36 (dd, 1H), 7.07 (m, 4H), 4.63 (s, 2H), 4.34 (d, 2H).

Example 74

Preparation of 1-(3,4-dichlorobenzyl)-3-(4-(iodomethyl)thiazol-2-yl)urea (Intermediate XXII)

To a solution of 1-(3,4-dichlorobenzyl)-3-(4-(chloromethyl)thiazol-2-yl)urea (1 eq) in acetone was added NaI (10 eq) at once. The mixture was stirred at room temperature for 2 h. The volatiles were removed in vacuo and the mixture was taken up in water and EtOAc. The layers were separated and the organic phase was partitioned with water and then brine, dried over Na$_2$SO$_4$, filtered, and concentrated in vacuo to afford 1-(3,4-dichlorobenzyl)-3-(4-(iodomethyl)thiazol-2-yl)urea as a tan-colored solid in near quantitative yield.

Example 75

Preparation of 1-(3-fluorobenzyl)-3-(4-(iodomethyl)thiazol-2-yl)urea (Intermediate XXIII)

Prepared in a similar manner as 1-(3,4-dichlorobenzyl)-3-(4-(iodomethyl)thiazol-2-yl)urea (Example 74). $^1$H-NMR (ppm, CDCl$_3$): 7.27 (m, 1H), 7.10 (m, 2H), 6.95 (t, 1H), 6.75 (s, 1H), 4.50 (d, 2H), 4.35 (s, 2H).

Example 76

Method C

Preparation of Ureas Via Alkylation of Chlorides or Iodides

To a suspension of NaH (3 eq.) in THF at 0° C. was added the alkanol (or amine) (3 eq.) dropwise. 15-Crown-5 (<0.5 eq.) was added and the mixture was stirred for 30 min at 0° C. Subsequently, the (chloromethyl)thiazol-2-yl)urea, Intermediate XX or Intermediate XXI (1 eq) was added at once and the mixture was brought to ambient temperature and was stirred for 2-16 h. The conversion was checked by TLC. The reaction was quenched with water and extracted with EtOAc. The combined extracts were partitioned with brine, dried over Na$_2$SO$_4$, filtered and concentrated in vacuo. The products were purified by column chromatography (DCM/1-5% MeOH).

Alternatively, a solution of the 4-(iodomethyl)thiazol-2-yl) urea, intermediate XXII or intermediate XXIII (1 eq), the alkanol (1 eq.) and DIPEA (1 eq.) in DMA was heated for 5-20 min at 100-130° C. under microwave irradiation. The volatiles were removed in vacuo and the product was purified by reverse phase chromatography (acetonitrile/water) or column chromatography (DCM/NH$_3$ saturated MeOH or EtOAc/hexanes).

Alternatively a solution of (chloromethyl)thiazol-2-yl) urea, intermediate XX or intermediate XXI (1 eq), the amine (1 eq.) and DIPEA (1 eq.) in THF was heated for 20-30 min at 140-150° C. under microwave irradiation. The volatiles were removed in vacuo and the product was purified by column chromatography (DCM/1-5% MeOH or EtOAc/heptane, ½) or HPLC Reverse Phase column (water/acetonitrile).

The compounds of Examples 77-131 were prepared using Method C outlined in Example 76 starting with one of the corresponding intermediates described in Examples 72-75.

Example 77 tert-butyl 2-((2-(3-(3,4-dichlorobenzyl)ureido)thiazol-4-yl)methoxy)-ethylcarbamate $^1$H-NMR (300 MHz, CDCl$_3$): δ 7.50 (bs, 1H) 7.42 (d, 1H), 7.37 (s, 1H), 7.17 (d, 1H), 6.73 (s, 1H), 4.60 (bs, 1H), 4.45 (s, 2H), 4.42 (s, 2H), 3.43 (m, 2H), 3.20 (m, 2H), 1.40 (s, 9H).

Example 78

1-(3,4-dichlorobenzyl)-3-(4-((2-aminoethoxy)methyl)thiazol-2-yl)urea hydrochloride A solution of tert-butyl 2-((2-(3-(3,4-dichlorobenzyl)ureido)thiazol-4-yl)methoxy)-ethylcarbamate (Example 77) (350 mg) in 1,4-dioxane (3 mL) was treated with 4N HCl in 1,4-dioxane (4 mL). The mixture was stirred overnight, 5 mL of diethyl ether was added, and the precipitated material was isolated by filtration. $^1$H-NMR (300 MHz, DMSO-$d_6$): δ 10.85 (bs, 1H), 7.90 (bs, 2H), 7.60 (d, 1H), 7.50 (s, 1H), 7.27 (d, 1H), 6.97 (s, 1H), 4.43 (s, 2H), 4.30 (d, 2H), 3.60 (m, 2H), 2.98 (m, 2H).

Example 79

1-(3,4-dichloro-benzyl)-3-[4-(2-morpholin-4-yl-ethoxymethyl)-thiazol-2-yl]-urea $^1$H NMR (400 MHz, CD$_3$OD): δ 7.45 (s, 1H), 7.41 (d, 1H), 7.21 (d, 1H), 7.06 (s, 1H), 4.66 (s, 2H), 4.36 (s, 2H), 4.12-3.94 (m, 6H), 3.65-3.54 (m, 6H). MS (ES+): M/Z 445, 447 (M+1).

Example 80

N-(2-{2-[3-(3,4-dichloro-benzyl)-ureido]-thiazol-4-ylmethoxy}-ethyl)-acetamide $^1$H NMR (400 MHz, CD$_3$OD): δ 7.47 (s, 1H), 7.45 (d, 1H), 7.25 (d, 1H), 6.88 (s, 1H), 4.44 (s, 2H), 4.40 (s, 2H), 3.53 (m, 2H), 3.35 (m, 2H), 1.92 (s, 3H). MS (ES+): M/Z 417 (M+1).

Example 81

1-(benzo[d][1,3]dioxol-5-ylmethyl)-3-(4-((2-(methylthio)ethoxy)methyl)thiazol-2-yl)urea Step 1: Synthesis of 1-(Benzo[d][1,3]dioxol-5-ylmethyl)-3-(4-(chloromethyl)thiazol-2-yl)urea intermediate: Phosgene (54.0 mmol, 27.9 mL of a 1.93 M solution in toluene) was placed in a 3-neck-flask and cooled to 0° C. THF (10 mL) was added, followed by a mixture of piperonylamine (27.0 mmol, 4.0 g) and DIPEA (56.7 mmol, 7.3 g) in THF (20 mL) at 0° C. After complete addition the mixture was stirred for another 40 min at 0° C. The reaction mixture was then concentrated. To the crude material THF (40 mL) and DIPEA (4.4 mL) were added. This mixture was then added to a slurry of 2-amino-4-(chloromethyl)thiazole hydrochloride (24.3 mmol, 4.5 g) in THF (50 mL). After stirring for 72 h at room temperature the reaction mixture was filtered through celite. The celite was washed with ethylacetate. The combined filtrate was concentrated and the material was directly applied to column chromatography (MeOH/DCM) providing 2.6 g (32%) of the desired intermediate. 1H-NMR (CD$_3$OD, 300 MHz) δ 6.96 (s, 1H), 6.79 (m, 3H), 5.91 (s, 2H), 4.55 (s, 2H), 4.32 (s, 2H).

Step 2: The 1-(Benzo[d][1,3]dioxol-5-ylmethyl)-3-(4-(chloromethyl)thiazol-2-yl)urea prepared in Step 1 was then used to prepare the title compound following Method C (Example 76). $^1$H-NMR (CD$_3$OD, 300 MHz): δ 6.87 (s, 1H), 6.79 (m, 3H), 5.91 (s, 2H), 4.45 (s, 2H), 4.32 (s, 2H), 3.67 (t, 2H), 2.66 (t, 2H), 2.1 (s, 3H).

Example 82

1-(benzo[d][1,3]dioxol-5-ylmethyl)-3-(4-((2-(methylsulfoxyl)ethoxy)methyl)thiazol-2-yl)urea 1-(benzo[d][1,3]dioxol-5-ylmethyl)-3-(4-((2-(methylthio)ethoxy)methyl) thiazol-2-yl)urea (Example 81) (0.3 mmol, 0.116 g) was dissolved in CH$_2$Cl$_2$ (5 mL). m-Chloroperbenzoic acid (1 eq, 0.3 mmol, 0.052 g) was added and the mixture was stirred at room temperature for 2 h. Then more CH$_2$Cl$_2$ (50 mL) was added and the mixture was partitioned with aq. NaHCO$_3$ (2×20 mL), then water (20 mL), dried (Na$_2$SO$_4$), filtered, and concentrated to give an oil. Column chromatography (water/acetonitrile) (silica gel, CH$_2$Cl$_2$/MeOH gradient) and preparative HPLC yielded 0.013 g (10%) of a white solid. $^1$H-NMR (CD$_3$OD, 300 MHz): δ 6.88 (s, 1H), 6.78 (m, 3H), 5.91 (s, 2H), 4.47 (s, 2H), 4.32 (s, 2H), 3.84 (m, 2H), 3.13 (m, 1H), 2.94 (m, 1H), 2.66 (s, 3H). m/e: 398 (M+H).

Example 83

1-(benzo[d][1,3]dioxol-5-ylmethyl)-3-(4-((2-(methylsulfone)ethoxy)methyl)thiazol-2-yl)urea 1-(benzo[d][1,3]dioxol-5-ylmethyl)-3-(4-((2-(methylthio)ethoxy)methyl) thiazol-2-yl)urea (Example 81) (1.5 mmol, 0.6 g) was dissolved in CHCl$_3$ (5 mL). 3-chloro-perbenzoic acid (2.2 eq, 3.46 mmol, 0.59 g) was added and the mixture was stirred at room temperature over night. Then CH$_2$Cl$_2$ (200 mL) was added and the mixture was partitioned with aq. NaHCO$_3$ (2×40 mL), then water (60 mL), dried (Na$_2$SO$_4$), filtered, and concentrated to give an oil. Column chromatography (silica gel, CH$_2$Cl$_2$/MeOH gradient) and preparative HPLC (water/acetonitrile) yielded 0.035 g (8% over two steps) of a white solid. $^1$H NMR (300 MHz, CD$_3$OD): δ 6.91 (s, 1H), 6.82-6.78 (m, 3H), 5.92 (s, 2H), 4.48 (s, 2H), 4.32 (s, 2H), 3.91 (t, 2H), 3.36-3.33 (m, 2H), 3.00 (s, 3H).

Example 84

1-(3,4-dichlorobenzyl)-3-(4-((2-(2-methoxyethoxy)ethoxy)methyl)thiazol-2-yl)urea $^1$H-NMR (300 MHz, CDCl$_3$): δ 7.68 (bs, 1H), 7.44 (d, 1H), 7.37 (d, 1H), 7.26 (dd, 1H), 6.75 (s, 1H), 4.45 (s, 2H), 4.41 (d, 2H), 3.4 (m, 8H), 3.31 (s, 3H).

Example 85

1-(3,4-dichlorobenzyl)-3-(4-((2-(4-methylpiperazin-1-yl)ethoxy)methyl)thiazol-2-yl)urea $^1$H-NMR (300 MHz, CDCl$_3$): δ 7.79 (bs, 1H), 7.43 (d, 1H), 7.36 (d, 1H), 7.17 (dd, 1H), 6.72 (s, 1H), 4.41 (d, 2H), 4.40 (s, 2H), 3.42 (t, 2H), 2.37 (t, 2H), 2.33 (bs, 4H), 2.19 (s, 3H).

Example 86

1-(3,4-Dichloro-benzyl)-3-[4-(2-imidazol-1-yl-ethoxymethyl)-thiazol-2-yl]-urea $^1$H NMR (300 MHz, CD$_3$OD): δ 7.65 (s, 1H), 7.48-7.45 (m, 2H), 7.25 (m, 1H), 7.12 (s, 1H), 6.92 (s, 1H), 6.76 (s, 1H), 4.85 (s, 2H), 4.42 (s, 2H), 4.18 (t, 2H), 3.75 (t, 2H).

Example 87

1-(3,4-dichlorobenzyl)-3-(4-((2-(2-(2-methoxyethoxy)ethoxy)ethoxy)methyl)thiazol-2-yl)urea $^1$H-NMR (300 MHz, CDCl$_3$): δ 7.68 (bs, 1H), 7.44 (d, 1H), 7.37 (d, 1H), 7.26 (dd, 1H), 6.75 (s, 1H), 4.45 (s, 2H), 4.41 (d, 2H), 3.5 (m, 12H), 3.31 (s, 3H).

Example 88

1-(3,4-Dichloro-benzyl)-3-{4-[2-(1-methyl-1H-imidazol-2-ylsulfanyl)-ethoxymethyl]-thiazol-2-yl}-urea $^1$H NMR (400 MHz, CD$_3$OD): δ 7.46 (d, 1H), 7.47 (s, 1H), 7.24 (dd, 1H), 7.11 (d, 1H), 6.96 (d, 1H), 6.79 (s, 1H), 4.39 (s, 2H), 4.38 (s, 2H), 3.65 (s, 3H), 3.63 (t, 2H), 3.10 (t, 2H). MS (ES+): M/Z 472 and 474 (M+1).

Example 89

1-(3,4-Dichloro-benzyl)-3-{4-[2-(4-methyl-thiazol-5-yl)-ethoxymethyl]-thiazol-2-yl}-urea $^1$H NMR (400 MHz, CD$_3$OD): δ 7.48 (d, 1H), 7.46 (s, 1H), 7.24 (dd, 1H), 7.18 (s, 1H), 5.62 (s, 2H), 4.38 (s, 2H), 3.80 (t, 2H), 3.09 (t, 2H), 2.55 (s, 3H). MS (ES+): M/Z 457 and 459 (M+1).

Example 90

1-(3,4-dichlorobenzyl)-3-(4-(allyloxymethyl)thiazol-2-yl)urea $^1$H-NMR (300 MHz, CDCl$_3$): δ 11.5 (bs, 1H), 7.57 (bs, 1H), 7.38 (d, 1H), 7.37 (s, 1H), 7.14 (dd, 1H), 6.75 (s, 1H), 5.71 (m, 1H), 5.19 (m, 2H), 4.43 (s, 2H), 4.38 (d, 2H), 3.83 (d, 2H).

Example 91

1-(3,4-dichlorobenzyl)-3-(4-((2,3-dihydroxypropoxy)methyl)thiazol-2-yl)urea

To a solution of 1-(3,4-dichlorobenzyl)-3-(4-(allyloxymethyl)thiazol-2-yl)urea (Example 90, 100 mg, 0.27 mmol) in a mixture of acetone/water 10/1 (2 ml) was added TMANO (trimethylamine N-oxide, 45 mg, 0.40 mmol) and a OsO$_4$ solution (4% in water, 0.34 mL, 5.4 µmol). The mixture was stirred at room temperature for 3 h and a saturated NaHCO$_3$ solution was added. The solution was extracted with EtOAc (2×25 mL) and the combined extracts were dried over Na$_2$SO$_4$, filtered, and concentrated in vacuo to afford 100 mg of an off-white solid. Purification by column chromatography (SiO$_2$, DCM/4% 7N NH$_3$ in MeOH). $^1$H-NMR (300 MHz, CDCl$_3$): δ 7.34 (s, 1H), 7.33 (d, 1H), 7.08 (d, 1H), 7.05 (bs, 1H), 6.62 (s, 1H), 4.38 (s, 2H). 4.33 (d, 2H), 3.86 (t, 1H), 3.62-3.50 (m, 4H).

Example 92

1-(3,4-Dichloro-benzyl)-3-[4-(3-pyridin-2-yl-propoxymethyl)-thiazol-2-yl]-urea $^1$H NMR (400 MHz, CD$_3$OD): δ 8.91 (d, 1H), 8.45 (m, 1H), 8.02 (d, 1H), 7.90 (m, 1H), 7.46-7.41 (m, 2H), 7.22 (dd, 1H), 7.00 (s, 1H), 5.73 (s, 2H), 4.36 (s, 2H), 3.67 (t, 2H), 1.97 (m, 2H).

Example 93

1-(3,4-Dichloro-benzyl)-3-[4-(2-pyridin-3-yl-ethoxymethyl)-thiazol-2-yl]-urea $^1$H NMR (400 MHz, CD$_3$OD): δ 8.93 (s, 1H), 8.85 (d, 1H), 8.46 (d, 1H), 7.87 (m, 1H), 7.46-7.40 (m, 2H), 7.21 (dd, 1H), 7.04 (s, 1H), 5.63 (s, 2H), 4.36 (s, 2H), 3.84 (t, 2H), 3.02 (t, 2H). MS (ES+): M/Z 437 and 439 (M+1).

Example 94

1-(3,4-Dichloro-benzyl)-3-[4-(octahydro-quinolizin-1-ylmethoxymethyl)-thiazol-2-yl]-urea $^1$H NMR (400 MHz, CD$_3$OD): δ 7.49 (d, 1H), 7.45 (d, 1H), 7.25 (dd, 1H), 6.99 (s, 1H), 4.58 (m, 2H), 4.38 (s, 2H), 3.92-3.35 (m, 5H), 3.17 (m, 1H), 2.83 (m, 1H), 2.38 (m, 1H), 2.05-1.63 (m, 8H), 1.5-1.38 (m, 2H). MS (ES+): M/Z 483 and 485 (M+1).

Example 95

1-(3,4-dichlorobenzyl)-3-(4-((2-(pyrrolidin-1-yl)ethoxy)methyl)thiazol-2-yl)urea oxalic acid salt $^1$H-NMR (300 MHz, CD$_3$OD): δ 7.48 (dd, 2H), 7.26 (dd, 1H), 6.96 (s, 1H), 4.52 (s, 2H), 4.40 (s, 2H), 3.77 (t, 2H), 3.54 (bs, 2H), 3.39 (t, 2H), 3.07 (bs, 2H), 2.01 (bd, 4H).

Example 96

1-(3,4-Dichloro-benzyl)-3-[4-(1-methyl-piperidin-4-yloxymethyl)-thiazol-2-yl]-urea $^1$H-NMR (300 MHz, CD$_3$OD): δ 7.49-7.41 (m, 2H), 7.28-7.14 (m, 2H), 4.47-4.38 (m, 4H), 3.67-3.02 (m, 8H), 1.98-1.70 (m, 4H).

Example 97

1-(3,4-dichlorobenzyl)-3-(4-((2-(2-oxooxazolidin-3-yl)ethoxy)methyl)thiazol-2-yl)urea $^1$H-NMR (300 MHz, CD$_3$OD): δ 7.49 (s, 1H), 7.48 (d, 1H), 7.25 (dd, 1H), 6.88 (s, 1H), 4.46 (s, 2H), 4.40 (s, 2H), 4.30 (d, 2H), 3.66 (m, 4H), 3.43 (t, 2H).

Example 98

1-(3,4-dichlorobenzyl)-3-(4-((2-(methylsulfonamido)ethoxy)methyl)thiazol-2-yl)urea $^1$H-NMR (300 MHz, CDCl$_3$): δ 7.29 (m, 1H), 7.00 (m, 2H), 6.65 (s, 1H), 4.47 (s, 2H), 4.46 (s, 2H), 3.64 (t, 2H), 3.24 (t, 2H), 2.89 (s, 3H).

Example 99 methyl 3-((2-(3-(3-fluorobenzyl)ureido)thiazol-4-yl)methoxy)pyrazine-2-carboxylate 1-(3-fluorobenzyl)-3-(4-(iodomethyl)thiazol-2-yl)urea (Intermediate XXIII, 1.0 mmol) and methyl 3-hydroxypyrazine-2-carboxylate (1.0 mmol) were dissolved in N-methylpyrrolidinone (3 ml) and K$_2$CO$_3$ (1.1 eq) was added. The mixture was stirred overnight. 20 ml water was added and the product was extracted three times with dichloromethane. The organic was dried over $Na_2SO_4$, filtered, and concentrated. The crude was purified by column chromatography using 0-70% gradient of saturated ammonia/MeOH and dichloromethane. $^1$H NMR (400 MHz, DMSO-$d_6$): δ 10.73 (s, 1H), 7.89 (d, 1H), 7.40 (d, 1H), 7.35 (m, 1H), 6.95-7.10 (m, 3H), 6.94 (m, 2H), 5.04 (s, 2H), 4.31 (d, 2H), 3.79 (s, 3H). MS (ES+): M/Z 418 (M+1).

Example 100

1-(3-fluorobenzyl)-3-(4-((3-methylpyrazin-2-yloxy) methyl)thiazol-2-yl)urea 1-(3-fluorobenzyl)-3-(4-(iodomethyl)thiazol-2-yl)urea (1.0 mmol) and excess of 3-methylpyrazin-2-ol sodium salt were dissolved in N,N-dimethylformamide (3 ml). The mixture was stirred overnight. Water (20 ml) was added and the product was extracted three times with dichloromethane. The organic was dried over $Na_2SO_4$, filtered, and concentrated. The crude was purified by column chromatography using 0-70% gradient of saturated ammonia/MeOH and dichloromethane. $^1$H NMR (400 MHz, DMSO-$d_6$): δ 10.73 (s, 1H), 7.48 (d, 1H), 7.36 (m, 1H), 7.15 (d, 1H), 7.06-7.12 (m, 3H), 6.96)m, 1H), 6.89 (s, 1H), 4.99 (s, 2H), 4.33 (d, 2H), 2.28 (s, 3H). MS (ES+): M/Z 374 (M+1).

Example 101

1-(3,4-Dichloro-benzyl)-3-[4-(4-formyl-piperazin-1-ylmethyl)-thiazol-2-yl]-urea $^1$H NMR (400 MHz, CD$_3$OD): δ 7.99 (s, 1H), 7.48 (s, 1H), 7.46 (d, 1H), 6.82 (s, 1H), 4.41 (s, 2H), 3.54 (s, 2H), 3.51 (m, 2H), 3.43 (m, 2H), 2.51 (m, 2H), 2.47 (m, 2H). MS (ES+): M/Z 428 (M+1).

Example 102

[2-({2-[3-(3,4-Dichloro-benzyl)-ureido]-thiazol-4-ylmethyl}-methyl-amino)-ethyl]-carbamic acid tert-butyl ester $^1$H NMR (400 MHz, CD$_3$OD): δ 7.50-7.44 (m, 2H), 7.26 (d, 1H), 6.79 (s, 1H), 4.41 (s, 2H), 3.52 (s, 2H), 3.17 (m, 2H), 2.50 (m, 2H), 2.28 (s, 3H), 1.40 (s, 9H). MS (ES+): M/Z 488, 490 (M+1).

Example 103

1-(4-{[(2-Amino-ethyl)-methyl-amino]-methyl}-thiazol-2-yl)-3-(3,4-dichloro-benzyl)-urea hydrochloride

[2-({2-[3-(3,4-Dichloro-benzyl)-ureido]-thiazol-4-ylmethyl}-methyl-amino)-ethyl]-carbamic acid tert-butyl ester (Example 102) was treated with HCl, 4.0M in dioxane in a similar way as Example 78 to give the title compound. $^1$H NMR (400 MHz, CD$_3$OD): δ 7.50-7.44 (m, 2H), 7.28-7.24 (m, 2H), 4.41 (s, 4H), 3.46 (br s, 4H), 2.95 (s, 3H). MS (ES+): M/Z 388, 390 (M+1).

Example 104

1-(3,4-dichlorobenzyl)-3-(4-((4-methylpiperazin-1-yl)methyl)thiazol-2-yl)urea hydrochloride The free amine was treated after purification by column chromatography with HCl in dioxane to afford the hydrochloride. 30% yield. $^1$H-NMR (300 MHz, DMSO-$d_6$): δ 10.90 (bs, 1H), 7.90 (bs, 1H), 7.60 (d, 1H), 7.53 (s, 1H), 7.26 (d, 1H), 7.24 (s, 1H), 4.37 (d, 2H), 4.28 (bs, 2H), 3.60 (m, 4H), 3.35 (m, 4H), 2.80 (s, 3H). M/z (pos. ESI)=413 [M+H].

Example 105

1-(3,4-dichlorobenzyl)-3-(4-((4-ethylpiperazin-1-yl) methyl)thiazol-2-yl)urea di-hydrochloride $^1$H-NMR (300 MHz, CD$_3$OD): δ 7.48 (m, 2H), 7.27 (m, 2H), 4.41 (s, 4H), 3.20-3.90 (b, 10H), 1.38 (t, 3H). M/z (pos. ESI)=427 [M+H].

Example 106

1-(3,4-dichlorobenzyl)-3-(4-((4-phenylpiperazin-1-yl)methyl)thiazol-2-yl)urea di-hydrochloride $^1$H-NMR (300 MHz, CD$_3$OD): δ 7.49 (d, 2H), 7.25 (m, 42H), 7.02 (d, 2H), 6.94 (t, 1H), 4.41 (s, 2H), 4.37 (s, 2H), 3.0-3.80 (br, 8H). M/z (pos. ESI)=475 (M+H).

Example 107

1-(3,4-Dichloro-benzyl)-3-[4-(4-pyrimidin-2-yl-piperazin-1-ylmethyl)-thiazol-2-yl]-urea $^1$H-NMR (300 MHz, CD$_3$OD): δ 8.39 (d, 2H), 7.47 (d, 2H), 7.26 (d, 1H), 7.20 (s, 1H), 6.72 (s, 1H), 4.40 (s, 2H), 4.33 (s, 2H), 3.0-3.80 (br, 8H). M/z (pos. ESI)=477 (M+H).

Example 108

1-(4-{[Bis-(2-methoxy-ethyl)-amino]-methyl}-thiazol-2-yl)-3-(3,4-dichloro-benzyl)-urea hydrochloride $^1$H-NMR (300 MHz, CD$_3$OD): δ 7.48 (m, 2H), 7.22 (m, 2H), 4.40 (s, 4H), 3.74 (m, 2H), 3.45 (br, 4H), 3.40 (s, 6H). M/z (pos. ESI)=446 (M+H).

Example 109

({2-[3-(3,4-Dichloro-benzyl)-ureido]-thiazol-4-ylmethyl}-methyl-amino)-acetic acid tert-butyl ester $^1$H-NMR (300 MHz, CD$_3$OD): δ 7.48 (m, 2H), 7.25 (d, 2H), 6.79 (s, 1H), 4.40 (s, 4H), 3.65 (s, 2H), 3.18 (s, 2H), 2.37 (s, 3H), 1.46 (s, 9H). M/z (pos. ESI)=458 (M+H).

Example 110

({2-[3-(3,4-Dichloro-benzyl)-ureido]-thiazol-4-ylmethyl}-methyl-amino)-acetic acid hydrochloride ({2-[3-(3,4-Dichloro-benzyl)-ureido]-thiazol-4-ylmethyl}-methyl-amino)-acetic acid tert-butyl ester (Example 109) was treated with trifluoroacetic acid overnight. The TFA was removed by evaporation the residue was triturated with 2N HCl in diethyl ether to afford the title compound.

¹H-NMR (300 MHz, CD₃OD): δ 7.48 (d, 2H), 7.25 (d, 2H), 7.18 (s, 1H), 4.40 (s, 2H), 4.33 (s, 2H), 3.89 (s, 2H), 2.91 (s, 3H). M/z (pos. ESI)=402 (M+H).

Example 111

1-(3,4-Dichloro-benzyl)-3-[4-(hexahydro-pyrrolo[1,2-a]imidazol-1-ylmethyl)-thiazol-2-yl]-urea dihydrochloride ¹H-NMR (ppm, CD₃OD): δ 7.46 (d, 2H), 7.27 (d, 2H), 6.82 (s, 1H), 4.42 (s, 2H), 3.58 (m, 2H), 2.98 (m, 4H), 2.32 (d, 2H), 2.16 (m, 2H), 1.98 (t, 1H), 1.79 (m, 4H). M/z (pos. ESI)=425 (M+H).

Example 112

1-(3,4-Dichloro-benzyl)-3-{4-[(2-methoxy-ethylamino)-methyl]-thiazol-2-yl}-urea hydrochloride ¹H NMR (400 MHz, CD₃OD): δ 7.48 (s, 1H), 7.47 (d, 1H), 7.26 (d, 1H), 7.11 (s, 1H), 4.41 (s, 2H), 4.18 (s, 2H), 3.64 (t, 2H), 3.39 (s, 3H), 3.22 (t, 2H). MS (ES+): M/Z 389, 391 (M+1).

Example 113

1-(3,4-Dichloro-benzyl)-3-(4-{[(2-methoxy-ethyl)-methyl-amino]-methyl}-thiazol-2-yl)-urea ¹H NMR (400 MHz, CD₃OD): δ 7.48 (s, 1H), 7.47 (d, 2H), 7.26 (d, 2H), 6.80 (s, 1H), 4.41 (s, 2H), 3.57 (s, 2H), 3.51 (t, 2H), 3.29 (s, 3H), 2.62 (t, 2H), 2.30 (s, 3H). MS (ES+): M/Z 403, 405 (M+1).

Example 114

1-(3,4-Dichloro-benzyl)-3-(4-morpholin-4-ylmethyl-thiazol-2-yl)-urea hydrochloride ¹H NMR (400 MHz, CD₃OD): δ 7.48 (s, 1H), 7.47 (d, 1H), 7.25 (d, 1H), 7.21 (s, 1H), 4.40 (s, 2H), 4.30 (s, 2H), 4.04 (br m, 2H), 3.74 (br m, 2H), 3.42 (br m, 2H), 3.21 (br m, 2H). MS (ES+): M/Z 401, 403 (M+1).

Example 115

1-(3,4-Dichloro-benzyl)-3-(4-{[(2-dimethylamino-ethyl)-methyl-amino]-methyl}-thiazol-2-yl)-urea dihydrochloride ¹H NMR (400 MHz, CD₃OD): δ 7.48 (s, 1H), 7.45 (d, 1H), 7.28 (s, 1H), 7.25 (d, 1H), 4.41 (s, 4H), 3.68 (br m, 4H), 2.98 (s, 6H), 2.93 (s, 3H). MS (ES+): M/Z 416, 418 (M+1).

Example 116

1-(3,4-Dichloro-benzyl)-3-(4-{[ethyl-(2-methoxy-ethyl)-amino]-methyl}-thiazol-2-yl)-urea ¹H NMR (400 MHz, CD₃OD): δ 7.50-7.46 (m, 2H), 7.26 (d, 1H), 7.22 (s, 1H), 4.41 (s, 2H), 4.34 (s, 2H), 3.72 (m, 2H), 3.40 (s, 3H), 3.35 (m, 2H), 3.26 (m, 2H), 1.37 (t, 3H). MS (ES+): M/Z 417, 419 (M+1).

Example 117

1-(3,4-dichlorobenzyl)-3-(4-((dimethylamino)methyl)thiazol-2-yl)urea

¹H-NMR (CDCl₃, 300 MHz): δ 8.9 (bt, 1H), 7.37 (d, 1H), 7.36 (d, 1H), 7.11 (dd, 1H), 6.63 (s, 1H), 4.40 (d, 2H), 3.34 (s, 2H), 2.05 (s, 6H).

Example 118

1-(benzo[d][1,3]dioxol-5-ylmethyl)-3-(4-(((2-methoxyethyl)(methyl)amino)methyl)thiazol-2-yl)urea The 1-(Benzo[d][1,3]dioxol-5-ylmethyl)-3-(4-(chloromethyl)thiazol-2-yl)urea intermediate prepared in Step 1 of Example 81 was then used to prepare the title compound following Method C (Example 76). ¹H-NMR (CD₃OD, 300 MHz): δ 6.81 (s, 1H), 6.78 (m, 3H), 5.91 (s, 2H), 4.46 (s, 2H), 4.32 (s, 2H), 3.63 (m, 2H), 3.50 (m, 2H), 3.34 (s, 3H). MS (ES+): M/Z 366 (M+H).

Example 119

1-(benzo[d][1,3]dioxol-5-ylmethyl)-3-(4-(((2-(dimethylamino)ethyl)(methyl)amino)methyl)thiazol-2-yl)urea The 1-(Benzo[d][1,3]dioxol-5-ylmethyl)-3-(4-(chloromethyl)thiazol-2-yl)urea intermediate prepared in Step 1 of Example 81 was then used to prepare the title compound following Method C (Example 76). ¹H-NMR (CD₃OD, 300 MHz): δ 6.82 (s, 1H), 6.77 (m, 3H), 5.91 (s, 2H), 4.32 (s, 2H), 3.52 (s, 2H), 2.52 (m, 2H), 2.50 (m, 2H), 2.27 (s, 3H), 2.21 (s, 6H). MS (ES+): M/Z 392 (M+H).

Example 120

1-(3,4-Dichloro-benzyl)-3-(4-{[(2-diethylamino-ethyl)-methyl-amino]-methyl}-thiazol-2-yl)-urea dihydrochloride salt ¹H NMR (400 MHz, CD₃OD): δ 7.47 (s, 1H), 7.44 (d, 1H), 7.30-7.22 (m, 2H), 4.39 (s, 4H), 3.71-3.52 (m, 4H), 3.93 (br s, 3H), 1.35 (br s, 6H). MS (ES+): M/Z 444 and 446 (M+1).

Example 121

1-(3,4-Dichloro-benzyl)-3-(4-{[(3-dimethylamino-propyl)-methyl-amino]-methyl}-thiazol-2-yl)-urea dihydrochloride salt ¹H NMR (400 MHz, CD₃OD): δ 7.50-7.46 (m, 2H), 7.29-7.25 (m, 2H), 4.42 (s, 2H), 4.35 (s, 2H), 3.26-3.08 (m, 4H), 2.93 (s, 6H), 2.91 (s, 3H), 2.28 (m, 2H). MS (ES+): M/Z 430 and 432 (M+1).

Example 122

1-(3,4-Dichloro-benzyl)-3-(4-{[(1,1-dioxo-tetrahydro-1-lambda6-thiophen-3-yl)-methyl-amino]-methyl}-thiazol-2-yl)-urea ¹H NMR (400 MHz, CD₃OD): δ 7.49-7.46 (m, 2H), 7.26 (dd, 1H), 6.83 (s, 1H), 4.41 (s, 2H), 3.63 (m, 2H), 3.49 (m, 1H), 3.35 (m, 1H), 3.23 (m, 1H), 3.09-3.00 (m, 2H), 2.45 (m, 1H), 2.30 (s, 3H), 2.13 (m, 1H). MS (ES+): M/Z 463 and 465 (M+1).

Example 123

1-(3,4-Dichloro-benzyl)-3-(4-{[(4-hydroxy-1,1-di-oxo-tetrahydro-1-lambda6-thiophen-3-yl)-methyl-amino]-methyl}-thiazol-2-yl)-urea $^1$H NMR (400 MHz, CD$_3$OD): δ 7.50-7.46 (m, 2H), 7.26 (dd, 1H), 6.84 (s, 1H), 4.75 (br m, 1H), 4.41 (s, 2H), 3.70 (m, 2H), 3.53 (m, 1H), 3.37-3.21 (m, 4H), 2.32 (s, 3H). MS (ES+): M/Z 479 and 481 (M+1).

Example 124

1-(3,4-Dichloro-benzyl)-3-{4-[(4-hydroxy-1,1-di-oxo-tetrahydro-1-lambda6-thiophen-3-ylamino)-methyl]-thiazol-2-yl}-urea $^1$H NMR (400 MHz, CDCl$_3$): δ 7.41 (m, 2H), 7.15 (d, 1H), 6.61 (s, 1H), 4.45 (m, 1H), 4.37 (m, 1H), 3.72-3.89 (m, 2H), 3.74 (m, 1H), 3.36 (m, 2H), 3.25 (m. 2H). MS (ES+): M/Z 465 and 467 (M+1).

Example 125

1-(4-{[(1,1-Dioxo-tetrahydro-1lambda6-thiophen-3-yl)-methyl-amino]-methyl}-thiazol-2-yl)-3-(3-fluoro-benzyl)-urea

MS (ES+): M/Z 413.2 (M+1).

Example 126

1-(3,4-Dichloro-benzyl)-3-(4-{[(2,3-dihydroxy-pro-pyl)-methyl-amino]-methyl}-thiazol-2-yl)-urea $^1$H NMR (400 MHz, CD$_3$OD): δ 7.49-7.45 (m, 2H), 7.25 (dd, 1H), 6.80 (s, 1H), 4.40 (s, 2H), 3.78 (m, 1H), 3.57 (m, 2H), 3.47 (m, 2H), 2.51 (m, 2H), 2.30 (s, 3H). MS (ES+): M/Z 419 and 421 (M+1).

Example 127

1-(3,4-dichlorobenzyl)-3-(4-((4-hydroxyisoxazoli-din-2-yl)methyl)thiazol-2-yl)urea $^1$H-NMR (CD$_3$OD, 300 MHz): δ 7.41-7.34 (m, 2H), 7.16 (dd, 1H), 6.71 (s, 1H), 4.62 (m, 2H) 4.32 (s, 2H), 4.15-3.50 (br m, 2H), 3.86 (d, 2H), 3.03-2.65 (br m, 2H). MS (ES+): M/Z 403 and 405 (M+1).

Example 128

1-(3,4-Dichloro-benzyl)-3-[4-(1,1-dioxo-1-lambda6-thiomorpholin-4-ylmethyl)-thiazol-2-yl]-urea hydrochloride salt $^1$H NMR (400 MHz, CD$_3$OD): δ 7.49-7.46 (m, 2H), 7.26 (dd, 1H), 7.19 (s, 1H), 4.41 (s, 2H), 4.34 (s, 2H), 3.74 (br m, 4H), 3.47 (br m, 4H), 3.34 (s, 3H). MS (ES+): M/Z 449 and 451 (M+1).

Example 129

2-({2-[3-(3,4-Dichloro-benzyl)-ureido]-thiazol-4-ylmethyl}-methyl-amino)-N-(1,1-dioxo-tetrahydro-1lambda6-thiophen-3-yl)-acetamide $^1$H NMR (400 MHz, CD$_3$OD): δ 7.50-7.46 (m, 2H), 7.26 (dd, 1H), 6.83 (s, 1H), 4.64 (m, 1H), 4.41 (s, 2H), 3.54 (s, 2H), 3.43 (m, 1H), 3.19-3.06 (m, 4H), 2.49 (m, 1H), 2.30 (s, 3H), 2.24 (m, 1H). MS (ES+): M/Z 520 and 522 (M+1).

Example 130

1-(3-Fluoro-benzyl)-3-{4-[(methyl-o-tolyl-amino)-methyl]-thiazol-2-yl}-urea $^1$H NMR (400 MHz, DMSO-d$_6$): δ 10.58 (s, 1H), 7.36 (m, 2H), 7.15-7.00 (m, 7H), 6.90 (m, 1H), 6.75 (s, 1H), 4.33 (d, 2H), 3.91 (s, 2H), 2.61 (s, 3H), 2.30 (s, 3H). MS (ES+): M/Z 385 (M+1).

Example 131

1-(3-Fluoro-benzyl)-3-{4-[(methyl-pyridin-2-yl-amino)-methyl]-thiazol-2-yl}-urea $^1$H NMR (400 MHz, CD$_3$OD): δ 8.07 (d, 1H), 7.54 (t, 1H), 7.39 (m, 1H), 7.16 (d, 1H), 7.10-7.00 (m, 2H), 6.75 (d, 1H), 6.67 (s, 1H), 6.64 (t, 1H), 4.73 (s, 2H), 4.45 (s, 2H), 3.14 (s, 3H). MS (ES+): M/Z 372 (M+1).

Example 132

1-(3,4-Dichloro-benzyl)-3-(4-methylaminomethyl-thiazol-2-yl)-urea

A solution of 1-(3,4-dichlorobenzyl)-3-(4-(chloromethyl)thiazol-2-yl)urea (Intermediate XX in Example 72) and excess amine (2.0M solution in THF) was heated for 15 min at 60° C. under microwave irradiation. The volatiles were removed in vacuo and the product was purified by column chromatography (DCM/0-15% NH$_3$ saturated MeOH). $^1$H NMR (400 MHz, CD$_3$OD): δ 7.50-7.45 (m, 2H), 7.26 (dd, 1H), 6.77 (s, 1H), 4.41 (s, 2H), 3.66 (s, 2H), 2.37 (s, 3H). MS (ES+): M/Z 345 and 347 (M+1).

Example 133

1-(3,4-Dichlorobenzyl)-3-(4-((((3,5-dimethylisox-azol-4-yl)methyl)(methyl)amino)methyl)thiazol-2-yl)urea Sodium triacetoxyborohydride (86 mg, 0.4 mmol, 2.0 eq) was added to a dichloromethane (2 mL) solution of 1-(3,4-Dichloro-benzyl)-3-(4-methylaminomethyl-thiazol-2-yl)-urea (Example 132, 70 mg, 0.2 mmol) and 3,5-dimethylisox-azole-4-carbaldehyde (33 mg, 0.25 mmol, 1.25 eq). After 16 hours of stirring, methanol (1 mL) and aqueous HCl (0.5 mL, 1N) were added. The mixture was neutralized with dilute NaHCO$_3$ solution. An aqueous work-up with dichloromethane and a chromatography (silica 0-3% MeOH in CH$_2$Cl$_2$) afforded the title compound. $^1$H NMR (400 MHz, CDCl$_3$): δ 7.36 (m, 2H), 7.10 (dd, 1H), 6.64 (s, 1H), 4.32 (d, 2H), 3.46 (s, 3H), 3.21 (s, 3H), 2.28 (s, 3H), 2.16 (s, 3H), 2.07 (s, 3H). MS (ES+): M/Z 454 (M+1).

Example 134

1-(3,4-Dichloro-benzyl)-3-(4-{[(2,4-dimethoxy-benzyl)-methyl-amino]-methyl}-thiazol-2-yl)-urea 1-(3,4-Dichloro-benzyl)-3-(4-methylaminomethyl-thiazol-2-yl)-urea (Example 132) was taken up in DCM with 1.5 equivalents of 2,4-Dimethoxy-benzaldehyde and several drops of acetic acid. Reaction was stirred for several hours at ambient temperature. Sodium cyanoborohydride (1.5 equivalents) was added at once and the reaction was stirred overnight at ambient temperature. An aqueous work-up with dichloromethane and chromatography (silica, DCM, 0-10% MeOH saturated with $NH_3$) afforded the title compound. $^1H$ NMR (400 MHz, DMSO-$d_6$): δ 10.65 (br s, 1H), 7.60 (d, 1H), 7.54 (d, 1H), 7.29 (dd, 1H), 7.27 (br d, 1H), 7.12 (br s, 1H), 6.58 (br s, 1H), 6.56-6.46 (m, 2H), 4.33 (d, 2H), 3.75 (s, 6H), 3.46 (br s, 4H), 2.12 (br s, 3H). MS (ES+): M/Z 495 and 497 (M+1).

Example 135

1-(3-fluorobenzyl)-3-(4-((((3-(hydroxymethyl)-5-methylisoxazol-4-yl)methyl)(methyl)amino)methyl)thiazol-2-yl)urea hydrochloride salt Step 1: 1-(3-fluorobenzyl)-3-(4-((methylamino)methyl)thiazol-2-yl)urea was prepared from 1-(4-Chloromethyl-thiazol-2-yl)-3-(3-fluoro-benzyl)-urea (Intermediate XXI) following the same procedure as described in Example 132.

Step 2: 3-(methoxycarbonyl)-5-methylisoxazole-4-carboxylic acid (1 mmol) was dissolved in N,N-dimethylformamide (5 ml), then diisopropylethylamine (1.2 eq.) and TBTU (1.2 eq) was added and stirred at room temperature for 5 minutes. 1-(3-fluorobenzyl)-3-(4-((methylamino)methyl)thiazol-2-yl)urea (1.0 mmol) was added and stirred overnight. Water (20 ml) was added to the reaction. The precipitate was filtered, washed with water and dried. The crude was purified by column using 0-100% gradient of 10% MeOH/EtOAc and hexanes to afford methyl 4-(((2-(3-(3-fluorobenzyl)ureido)thiazol-4-yl)methyl)(methyl)carbamoyl)-5-methylisoxazole-3-carboxylate.

Step 3: Methyl 4-(((2-(3-(3-fluorobenzyl)ureido)thiazol-4-yl)methyl)(methyl)carbamoyl)-5-methylisoxazole-3-carboxylate (105 mg) was suspended in diethyl ether (5 ml) and 1 M LiAlH$_4$ in THF (2.5 eq.) was added. The reaction was stirred at room temperature overnight. The reaction was quenched with water (0.1 ml) and 1 M NaOH (0.1 ml). The mixture was dried with Na$_2$SO$_4$ and filtered and washed with ethyl acetate. The combined filtrate was concentrated and purified by column using 0-100% gradient of 7 N ammonia/ MeOH and dichloromethane. The compound was converted to the HCl salt. $^1H$ NMR (400 MHz, CD$_3$OD): δ 7.32 (m, 1H), 7.20 (s, 1H), 7.14 (d, 1H), 7.06 (d, 1H), 6.98 (m, 1H), 4.74 (s, 2H), 4.44 (s, 2H), 4.36 (br, 2H), 2.81 (s, 3H), 2.50 (s, 3H), MS (ES+): M/Z 420 (M+1).

Example 136

1-(3,4-Dichloro-benzyl)-3-{4-[(2,3,4-trimethoxy-benzylamino)-methyl]-thiazol-2-yl}-urea Step 1: Preparation of [1-(3,4-dichlorobenzyl)-3-(4-formylthiazol-2-yl)urea] To a solution of 1-(3,4-Dichlorobenzyl)-3-(4-(hydroxymethyl)thiazol-2-yl)urea (Example 39, 9.1 mmol) in DMSO (80 mL) was added DIPEA (9.4 g, 72.8 mmol) and pyridine.SO$_3$ (5.79 g, 36.4 mmol) at ambient temperature and the mixture was stirred overnight. Water (300 mL) was added resulting in the precipitation of a tan colored solid. The solid was isolated by filtration, washed with water and Et$_2$O, and then azeotroped with toluene to afford 1-(3,4-dichlorobenzyl)-3-(4-formylthiazol-2-yl)urea (1.94 g, 5.88 mmol) as a tan colored solid in 64% yield. $^1$H-NMR (DMSO-d$_6$, 300 MHz): δ 11.04 (bs, 1H), 9.70 (s, 1H), 8.14 (s, 1H), 7.60 (d, 1H), 7.54 (s, 1H), 7.28 (d, 1H), 7.22 (bt, 1H), 4.32 (d, 2H).

Step 2: The aldehyde[1-(3,4-dichlorobenzyl)-3-(4-formylthiazol-2-yl)urea] (0.12 mmol) and the amine[(2,3,4-trimethoxyphenyl)methanamine] (3 eq) were suspended in MeOH/MeCN (8.5/1.5 mL) and stirred for 1 hour at 40° C. Subsequently the reaction mixture was cooled in an ice-bath and the NaCNBH$_3$ (1.5 eq) was added. The reaction mixture was stirred 1 hour at 2° C. and was then allowed to warm to room temperature. The crude reaction mixture was evaporated onto silica and purified by column chromatography (SiO$_2$: 4% 7 N NH$_3$ in MeOH/CH$_2$Cl$_2$). This afforded a yellow oil (59 mg). Purification by Prep-HPLC afforded a colorless oil (22 mg, 35% yield). $^1$H NMR (300 MHz, CD$_3$OD): δ 7.52-7.45 (m, 2H), 7.27 (dd, 1H), 6.97 (d, 1H), 6.79-6.69 (m, 2H), 4.43 (s, 2H), 3.86 (s, 3H), 3.84 (s, 3H), 3.82 (s, 3H), 3.70 (s, 2H), 3.69 (s, 2H). MS (ES+): M/Z 511 and 513 (M+1).

Example 137

1-(3,4-Dichloro-benzyl)-3-{4-[(2,4-dimethoxy-benzylamino)-methyl]-thiazol-2-yl}-urea 1-(3,4-dichlorobenzyl)-3-(4-(iodomethyl)thiazol-2-yl) urea (Intermediate XXII) was taken up in THF and an excess of the 2,4-dimethoxy-benzylamine (20 equiv.) was added. The reaction was allowed to stir overnight at room temperature. The volatiles were removed in vacuo. Resulting oil triturated with water to give a gooey solid. Water was decanted off and resulting residue was purified by column chromatography (DCM, 0-8% MeOH saturated with NH$_3$). $^1$H NMR (400 MHz, CDCl$_3$): δ 7.32 (d, 1H), 7.19 (br s, 1H), 7.01 (br d, 1H), 6.96 (d, 1H), 6.60 (s, 1H), 6.40-6.33 (m, 2H), 4.11 (br s, 2H), 3.78 (s, 3H), 3.71 (s, 3H), 3.69 (br s, 2H), 3.55 (br s, 3H).

Example 138

1-(3,4-Dichloro-benzyl)-3-{4-[(2-hydroxy-ethylamino)-methyl]-thiazol-2-yl}-urea 1-(3,4-dichlorobenzyl)-3-(4-(iodomethyl)thiazol-2-yl) urea (Intermediate XXII) was taken up in THF and an excess of the 2-Amino-ethanol (20 equiv.) was added. The reaction was allowed to stir overnight at room temperature. Reaction poured into water and extracted with ethyl acetate, partitioned with brine, dried over NaSO$_4$, filtered, and volatiles were removed in vacuo. The resulting solid was triturated with ethyl acetate, followed by diethyl ether to give the title compound. $^1$H NMR (400 MHz, CD$_3$OD): δ 7.50-7.45 (m, 2H), 7.26 (dd, 1H), 6.78 (s, 1H), 4.41 (s, 2H), 3.73 (s, 2H), 3.65 (t, 2H), 2.71 (t, 2H). MS (ES+): M/Z 375 and 377 (M+1).

Example 139

2-(3-(3,4-Dichlorobenzyl)ureido)-N-(2-methoxy-ethyl)-N-methylthiazole-4-carboxamide Step 1: Sodium hydroxide (24 mL, 24 mmol, 1N in water) was added to an ethanol (50 mL) solution of ethyl 2-(3-(3,4- dichlorobenzyl)ureido)thiazole-4-carboxylate (Example 38) (1.8 g, 4.8 mmol). The mixture was stirred overnight. The ethanol was removed by evaporation and the aqueous solution was filtered then the filter was washed with water (20 ml). The pH of the filtrate was adjusted to less than three with concentrated HCl. The precipitate was filtered, washed with water and dried to afford 2-(3-(3,4-dichlorobenzyl)ureido)thiazole-4-carboxylic acid.

Step 2: 2-methoxy-N-methylethanamine (56 µL, 0.625 mmol, 2.5 eq) was added to a DMF (2 mL) solution of 2-(3-(3,4-dichlorobenzyl)ureido)thiazole-4-carboxylic acid (87 mg, 0.25 mmol), TBTU (93 mg, 0.29 mmol, 1.15 eq) and triethylamine (100 µL). After an hour stirring, an aqueous work-up with EtOAc afforded the title compound. $^1$H NMR (400 MHz, CDCl$_3$): δ 11.27 (s, 1H), 8.70 (s, 1H), 7.49 (d, 1H), 7.35 (dd, 1H), 7.20 (dd, 1H), 4.40 (d, 2H), 2.80-3.70 (m, 7H, rotamers). MS (ES+): M/Z 417 (M+1).

Example 140

1-(3-Fluorobenzyl)-3-(4-((methyl(3-methylpyrazin-2-yl)amino)methyl)thiazol-2-yl)urea Step 1: 2-chloro-3-methylpyrazine (124 mg, 1.0 mmol) and methylamine (5 mL, 2M solution in THF) was irradiated in a microwave oven at 190° C. for 10 hours. The solution is evaporated and the residue was dissolved in CH$_2$Cl$_2$ (10 mL). It was partitioned with NaOH (1 mL, 5N), dried with NaSO$_4$, filtered and volatiles removed in vacuo to afford N,3-dimethylpyrazin-2-amine. $^1$H NMR (400 MHz, CDCl$_3$): δ 7.92 (d, 1H), 7.70 (d, 1H), 4.40 (s, br, 1H), 3.03 (d, 3H), 2.36 (s, 3H). MS (ES+): M/Z 124 (M+1).

Step 2: A CH$_2$Cl$_2$ (5 mL) suspension of 1-(4-(chloromethyl)thiazol-2-yl)-3-(3-fluorobenzyl)urea (Intermediate XXI) (90 mg, 0.30 mmol), N,3-dimethylpyrazin-2-amine (69 mg, 0.56 mmol) and finely powdered K$_2$CO$_3$ (83 mg, 0.60 mmol) was evaporated to dryness. This mix was heated at 80° C. for 60 hours. Upon cooling, the organics were taken up in CH$_2$Cl$_2$ (3×5 mL) and the insolubles were removed by filtration. The volatiles were then removed in vacuo. The crude product was purified with chromatography (silica 1-4% MeOH in CH$_2$Cl$_2$) to afford the title compound. $^1$H NMR (400 MHz, CDCl$_3$): δ 8.00 (s, 2H), 7.23 (m, 1H), 6.95 (m, 3H), 6.60 (s, 1H), 4.45 (d, 2H), 4.37 (s, 2H), 2.87 (s, 3H), 2.52 (s, 3H). MS (ES+): M/Z 387 (M+1).

Example 141

Method D

"N-capping" of 1-(3,4-dichlorobenzyl)-3-(4-((2-aminoethoxy)methyl)thiazol-2-yl)urea hydrochloride To a suspension of 1-(3,4-dichlorobenzyl)-3-(4-((2-aminoethoxy)methyl)thiazol-2-yl)urea hydrochloride (Example 78) in dichloromethane was added DIPEA (2.2 equivalents). The solution was cooled to 0° C. and the "capping" agent (1 equivalent) was added. The mixture was stirred overnight at room temperature. Evaporation of the volatiles afforded crude material which was purified by column chromatography (SiO$_2$, DCM/MeOH).

The compounds of Examples 142-145 were prepared using Method D outlined in Example 141.

Example 142

1-(3,4-dichlorobenzyl)-3-(4-((2-(methylsulfonamido)ethoxy)methyl)thiazol-2-yl)urea $^1$H-NMR (300 MHz, CDCl$_3$): δ 9.80 (bs, 1H), 7.39 (s, 1H), 7.38 (d, 1H), 7.14 (d, 1H), 7.10 (bs, 1H), 6.65 (s, 1H), 6.50 (bs, 1H), 4.49 (s, 2H), 4.42 (d, 2H), 3.67 (t, 2H), 3.24 (t, 2H), 2.91 (s, 3H).

Example 143

Diethyl 2-((2-(3-(3,4-dichlorobenzyl)ureido)thiazol-4-yl)methoxy)ethylphosphor-amidate $^1$H-NMR (300 MHz, CDCl$_3$): δ 11.07 (bs, 1H), 7.39 (s, 1H), 7.37 (d, 1H), 7.14 (d, 1H), 6.63 (s, 1H), 6.22 (bs, 1H), 5.91 (bm, 1H), 4.47 (s, 2H), 4.42 (d, 2H), 4.03 (m, 4H), 3.60 (t, 2H), 3.06 (m, 2H), 1.29 (t, 6H).

Example 144

(2-{2-[3-(3,4-Dichloro-benzyl)-ureido]-thiazol-4-ylmethoxy}-ethyl)-carbamic acid methyl ester $^1$H NMR (400 MHz, DMSO-d$_6$): δ 10.62 (br s, 1H), 7.58 (d, 1H), 7.52 (d, 1H), 7.27 (dd, 1H), 7.12 (br s, 1H), 6.86 (s, 1H), 4.34 (s, 2H), 4.30 (d, 2H), 3.49 (s, 3H), 3.41 (t, 2H), 3.12 (q, 2H). MS (ES+): M/Z 433 and 435 (M+1).

Example 145

1-(3,4-Dichloro-benzyl)-3-{4-[2-(3-ethyl-ureido)-ethoxymethyl]-thiazol-2-yl}-urea $^1$H NMR (400 MHz, DMSO-d$_6$): δ 10.62 (br s, 1H), 7.58 (d, 1H), 7.52 (d, 1H), 7.27 (dd, 1H), 7.12 (br m, 1H), 6.86 (s, 1H), 5.85 (m, 1H), 5.81 (m, 1H), 4.35 (s, 2H), 4.30 (d, 2H), 3.39 (t, 2H), 3.13 (q, 2H), 2.96 (m, 2H), 0.94 (t, 3H). MS (ES+): M/Z 446 and 448 (M+1).

Example 146

Method E

General Procedure for the Synthesis of Thioethers

A mixture of 1-(3,4-dichlorobenzyl)-3-(4-(chloromethyl)thiazol-2-yl)urea (Intermediate XX, 1 eq.), the corresponding thiophenol or benzyl thiole (2 eq.), cesium carbonate (2.2 eq.) and sodium iodide (2.2 eq.) was refluxed in THF for 2-16 hours. The reaction mixture was filtered through Celite and purified by column chromatography (silica gel, ethyl acetate/heptane or methanol/dichloromethane).

The compounds of Examples 147-156 were prepared using Method E outlined in Example 146.

Example 147

1-(3,4-Dichlorobenzyl)-3-(4-((4-methoxyphenylthio)methyl)thiazol-2-yl)urea $^1$H NMR (300 MHz, CDCl$_3$) δ 3.76 (s, 1H), 3.91 (s, 2H), 4.39 (d, 2H), 6.29 (s, 1H), 6.75-6.78 (m, 2H), 7.09-7.14 (m, 1H), 7.16-7.19 (m, 2H), 7.31-7.34 (m, 2H). M/z (pos. ESI)= 454 and 456 [M+H].

Example 148

1-(3,4-Dichlorobenzyl)-3-(4-((4-fluorophenylthio) methyl)thiazol-2-yl)urea $^1$H NMR (300 MHz, CDCl$_3$)=3.98 (s, 2H), 4.42 (d, 2H), 6.38 (s, 1H), 6.90-6.96 (m, 2H), 7.10-7.14 (m, 1H), 7.21-7.26 (m, 2H), 7.34-7.37 (m, 2H). M/z (pos. ESI)=442 and 444 [M+H].

Example 149

1-(3,4-dichlorobenzyl)-3-(4-((4-acetamidophenylthio)methyl)thiazol-2-yl)urea $^1$H NMR (300 MHz, CD$_3$OD): δ 7.47 (m, 4H), 7.23 (m, 3H), 6.57 (s, 1H), 4.39 (s, 2H), 4.02 (s, 2H), 2.09 (s, 3H).

Example 150

1-(3,4-Dichlorobenzyl)-3-(4-((3,4-dimethoxyphenylthio)methyl)-thiazol-2-yl)urea $^1$H NMR (300 MHz, CDCl$_3$) δ 3.77 (s, 3H), 3.84 (s, 3H), 3.94 (s, 2H), 4.40 (d, 2H), 6.33 (s, 1H), 6.77-6.85 (m, 3H), 7.09-7.10 (m, 1H), 7.32-7.35 (m, 2H). M/z (pos. ESI)=484 [M+H], 486 [M+H].

Example 151

1-(3,4-Dichlorobenzyl)-3-(4-((2-(pyrazin-2-yl)ethylthio)methyl)thiazol-2-yl)urea $^1$H NMR (300 MHz, CD$_3$OD): δ 8.50 (d, 1H), 8.49 (s, 1H), 8.40 (d, 1H), 7.47 (s, 1H), 7.44 (s, 1H), 7.24 (dd, 1H), 6.76 (s, 1H), 4.40 (s, 2H), 3.68 (s, 2H), 3.04 (t, 2H), 2.89 (t, 2H).

Example 152

1-(3,4-dichlorobenzyl)-3-(4-((4-methyl-4H-1,2,4-triazol-3-ylthio)methyl)thiazol-2-yl)urea $^1$H NMR (300 MHz, CDCl$_3$) δ 8.1 (s, 1H), 7.35 (m, 2H), 7.1 (d, 1H), 6.6 (s, 1H), 4.4 (s, 2H), 4.2 (s, 2H), 3.4 (s, 3H).

Example 153

1-(4-((1,3,4-thiadiazol-2-ylthio)methyl)thiazol-2-yl)-3-(3,4-dichlorobenzyl)urea $^1$H NMR (300 MHz, CD$_3$OD/CDCl$_3$); δ 9.0 (s, 1H), 7.35 (m, 2H), 7.1 (d, 1H), 6.7 (s, 1H), 4.4 (s, 2H), 4.3 (s, 2H).

Example 154

1-(3,4-dichlorobenzyl)-3-(4-((thiazol-2-ylthio)methyl)thiazol-2-yl)urea $^1$H NMR (300 MHz, CDCl$_3$); δ 10.6 (bs, 1H), 7.62 (d, 1H), 7.33 (m, 2H), 7.20 (d, 1H), 7.07 (d, 1H), 6.62 (s, 1H), 4.38 (d, 2H), 3.36 (s, 1H), 2.40 (bs, 1H).

Example 155

1-(3,4-dichlorobenzyl)-3-(4-((1-methyl-1H-tetrazol-5-ylthio)methyl)thiazol-2-yl)urea $^1$H NMR (300 MHz, DMSO-d$_6$); δ 7.57 (d, 1H), 7.51 (s, 1H), 7.26 (d, 1H), 7.20 (bt, 1H), 6.87 (s, 1H), 4.41 (s, 2H), 4.29 (d, 2H), 3.86 (s, 3H).

Example 156

1-(3,4-dichlorobenzyl)-3-(4-((4,5-dimethyl-4H-1,2,4-triazol-3-ylthio)methyl)thiazol-2-yl)urea $^1$H NMR (300 MHz, CD$_3$OD); δ 7.48 (m, 2H), 7.25 (d, 1H), 6.65 (s, 1H), 4.88 (s, 2H), 4.17 (s, 2H), 3.41 (s, 3H), 2.39 (s, 3H).

Example 157

5-Amino-3-(chloromethyl)-1,2,4-thiadiazole (Intermediate XXIV)

Ammonia was bubbled through a solution of 5-chloro-3-(chloromethyl)-1,2,4-thiadiazole (5.0 g, 29.6 mmol) in 2-propanol (80 ml) at 0-5° C. for several hours and then stirred overnight at ambient temperature. The reaction was monitored by GCMS, ammonia was recharged if necessary. When conversion was complete, the solids were removed by filtration and the filtrate was diluted with THF. The precipitate was removed again. The solvents were then removed under reduced pressure and a yellow oil remained. Addition of THF gave an almost white solid and a yellow solution. The solid was removed by filtration. The solution was evaporated to dryness giving a pale yellow solid in 45% yield (2.0 g, 13.3 mmol). This material was used in the next step without further purification. $^1$H NMR (300 MHz, d$_6$-DMSO)=δ 4.51 (s, 2H). M/z (pos. EI)=151, 149 [M+H].

Example 158

1-(3-Fluorobenzyl)-3-(3-(chloromethyl)-1,2,4-thiadiazol-5-yl)urea (Intermediate XXV)

A solution of 5-Amino-3-(chloromethyl)-1,2,4-thiadiazole (Intermediate XXIV) (1 equivalent) and the 3-fluorobenzyl isocyanate (1.2 equivalents) and DMAP (150 μmol) in NMP (12 ml) was heated in a microwave oven for 30 minutes at 150° C. After cooling to ambient temperature, the brown solution is poured into water (60 ml) and the mixture was extracted with ethyl acetate (5×20 ml). The combined organic layers were partitioned with water (2×20 ml), then brine, and dried over sodium sulphate, filtered and volatiles removed in vacuo. The crude material was first purified by normal phase column chromatography (silica gel, 12-75% ethyl acetate in heptane), followed by reversed phase column chromatography (C18, 10-100% methanol in water) to give a white solid. $^1$H NMR (300 MHz, d$_6$-DMSO) δ 4.36 (d, 2H), 4.69 (s, 2H), 7.03-7.13 (m, 3H), 7.33-7.38 (m, 1H), 7.45 (t, br, 1H).

Example 159

1-(3,4-Dichorobenzyl)-3-(3-(chloromethyl)-1,2,4-thiadiazol-5-yl)urea (Intermediate XXVI)

The title compound was prepared in a similar manner as Example 158. $^1$H NMR (300 MHz, d$_6$-DMSO) δ 4.34 (d, 2H), 4.69 (s, 2H), 7.27-7.30 (m, 1H), 7.51-7.60 (m, 3H).

Example 160

1-(3-Fluoro-benzyl)-3-(3-methylaminomethyl-[1,2,4]thiadiazol-5-yl)-urea (Intermediate XXVII)

A solution of 1-(3-Fluorobenzyl)-3-(3-(chloromethyl)-1,2,4-thiadiazol-5-yl)urea (Intermediate XXV) and excess methyl amine (2.0M solution in THF) was heated for 15 min at 60° C. under microwave irradiation. Filtered off insolubles and removed solvent in vacuo to give title compound.

Example 161

(3-Chloromethyl-[1,2,4]thiadiazol-5-yl)-(2,4-dimethoxy-benzyl)-amine (Intermediate XXVIII)

5-Chloro-3-chloromethyl-[1,2,4]thiadiazole (10 mmol) is added to a solution of 2,4-dimethoxybenzylamine (10 mmol) in THF at room temperature followed by addition of DIEA (10 mmol). The mixture is stirred overnight. The white precipitate is filtered and washed with THF. The filtrate is concentrated to oil and dried under high vacuum.

Example 162

(2,4-Dimethoxy-benzyl)-(3-{[(2-methoxy-ethyl)-methyl-amino]-methyl}-[1,2,4]thiadiazol-5-yl)-amine (Intermediate XXIX)

10 mmol of N-methyl-2-methoxyethylamine is added to the solution of (3-Chloromethyl-[1,2,4]thiadiazol-5-yl)-(2,4-dimethoxy-benzyl)-amine (Intermediate XXVIII) in 50 ml THF and 10 mmol of $Cs_2CO_3$ is added. The reaction is heated at reflux overnight. The reaction is cooled to room temperature and filtered, washed with THF. The filtrate is concentrated and purified by RP-HPLC.

Example 163

Method F

General Method for Synthesis of Thiadiazoles in Example 164 and 165

Step 1: (2,4-Dimethoxy-benzyl)-(3-{[(2-methoxy-ethyl)-methyl-amino]-methyl}-[1,2,4]thiadiazol-5-yl)-amine (Intermediate XXIX) was taken up in THF and the isocyanate (1.3 equiv) was added. The reaction mix was heated in the microwave for 30 min. at 140° C. Reaction was about 60% complete. Added additional isocyanate (0.4 equiv) and resubjected to same microwave conditions. Removed solvent in vacuo and purified by column chromatography (0-60% ethyl acetate (with 10% MeOH) in hexanes) to give 1-(2,4-Dimethoxy-benzyl)-3-(substituted-phenyl)-1-(3-{[(2-methoxy-ethyl)-methyl-amino]-methyl}-[1,2,4]thiadiazol-5-yl)-urea.

Step 2: Deprotection: The 1-(2,4-Dimethoxy-benzyl)-3-(substituted-phenyl)-1-(3-{[(2-methoxy-ethyl)-methyl-amino]-methyl}-[1,2,4]thiadiazol-5-yl)-urea from Step 1 was treated with TFA and allowed to stir at room temperature for 4 hours. Volatiles were removed in vacuo. The crude was then purified by column chromatography using a gradient of 0-12% MeOH (saturated with $NH_3$) in dichloromethane to give the title compound.

Examples 164 and 165 were prepared by Method E described in Example 163.

Example 164

1-(3,4-Dichloro-benzyl)-3-(3-{[(2-methoxy-ethyl)-methyl-amino]-methyl}-thiadiazol-5-yl)-urea $^1$H-NMR (300 MHz, $CDCl_3$): δ 8.80 (bs 1H), 7.40 (s, 1H), 7.39 (d, 1H), 7.15 (d, 1H), 4.47 (d, 2H), 3.70 (s, 2H), 3.36 (t, 2H), 3.17 (s, 3H), 2.56 (t, 2H), 2.23 (s, 3H).

Example 165

1-(3-Fluoro-benzyl)-3-(3-{[(2-methoxy-ethyl)-methyl-amino]-methyl}-[1,2,4]thiadiazol-5-yl)-urea $^1$H-NMR (300 MHz, $CDCl_3$): δ 8.81 (bs, 1H), 7.28 (m, 1H), 7.07 (d, 1H), 7.01 (d, 1H), 6.94 (m, 1H), 4.54 (d, 2H), 3.68 (s, 2H), 3.33 (t, 2H), 3.16 (s, 3H), 2.52 (t, 2H), 2.17 (s, 3H).

Example 166

1-(3-fluorobenzyl)-3-(3-((2-methoxyethoxy)methyl)-1,2,4-thiadiazol-5-yl)urea

Sodium hydride (4 eq, 2.66 mmol, 0.13 g of a 50 wt-% suspension in oil) was suspended in THF (2 mL) and cooled to 0° C. 2-methoxy ethanol (3 eq, 1.99 mmol, 0.15 g) and 15-crown-5-ether (1 drop) were added. 1-(3-Fluorobenzyl)-3-(3-(chloromethyl)-1,2,4-thiadiazol-5-yl)urea (Intermediate XXV) was added and the mixture was stirred over night with temperature allowed to rise to room temperature. Dichloromethane (50 mL) was added. The mixture was washed with water (2×10 mL), dried ($Na_2SO_4$), filtered and concentrated in vacuo. The crude material (0.2 g of an oil) was further purified by preparative HPLC to give 0.101 g. $^1$H-NMR (300 MHz, $CD_3OD$): δ 7.34 (m, 1H), 7.14 (d, 1H), 7.07 (d, 1H), 6.99 (m, 1H), 4.58 (s, 2H), 4.45 (s, 2H), 3.70 (t, 2H), 3.56 (t, 2H), 3.30 (s, 3H).

Example 167

1-(3,4-Dichloro-benzyl)-3-[3-(2-methoxy-ethoxymethyl)-[1,2,4]thiadiazol-5-yl]-urea The title compound was prepared in a similar manner as Example 166 starting from 1-(3,4-Dichorobenzyl)-3-(3-(chloromethyl)-1,2,4-thiadiazol-5-yl)urea (Intermediate XXVI). $^1$H NMR (400 MHz, $CDCl_3$): δ 12.05 (br s, 1H), 8.14 (br t, 1H), 7.47 (d, 1H), 7.41 (d, 1H), 7.22 (dd, 1H), 4.61 (s, 2H), 4.44 (d, 2H), 3.56 (m, 2H), 3.38 (m, 2H), 3.20 (s, 3H). MS (ES+): M/Z 391 and 393 (M+1).

Example 168

1-(3,4-Dichloro-benzyl)-3-(3-{1-[(1,1-dioxo-tetrahydro-1l6-thiophen-3-yl)-methyl-amino]-methyl}-[1,2,4]thiadiazol-5-yl)-urea Prepared from 1-(3,4-Dichorobenzyl)-3-(3-(chloromethyl)-1,2,4-thiadiazol-5-yl)urea (Intermediate XXVI) and the corresponding amine under microwave conditions following the procedure detailed in Method C (see Example 76). $^1$H NMR (400 MHz, $CD_3OD$): δ 7.49-7.45 (m, 2H), 7.25 (dd, 1H), 4.41 (s, 2H), 3.80 (m, 2H), 3.54 (m, 1H), 3.37 (m, 1H), 3.24 (m, 1H), 3.10-2.99 (m, 2H), 2.48 (m, 1H), 2.35 (s, 3H), 2.11 (m, 1H). MS (ES+): M/Z 464 and 466 (M+1).

Example 169

1-(3-{1-[(1,1-Dioxo-tetrahydro-1l6-thiophen-3-yl)-methyl-amino]-methyl}-[1,2,4]thiadiazol-5-yl)-3-(3-fluoro-benzyl)-urea Prepared from 1-(3-Fluorobenzyl)-3-(3-(chloromethyl)-1,2,4-thiadiazol-5-yl)urea (Intermediate XXV) and the corresponding amine under microwave conditions following procedure in Method C (see Example 76). $^1$H NMR (400 MHz, CD$_3$OD): δ 7.34 (m, 1H), 7.14 (m, 1H), 7.06 (m, 1H), 6.98 (m, 1H), 4.43 (s, 2H), 3.80 (m, 2H), 3.55 (m, 1H), 3.38 (m, 1H), 3.26 (m, 1H), 3.10-3.00 (m, 2H), 2.48 (m, 1H), 2.36 (s, 3H), 2.12 (m, 1H).

Example 170

1-(3-{[(3,5-Dimethyl-isoxazol-4-ylmethyl)-methyl-amino]-methyl}-[1,2,4]thiadiazol-5-yl)-3-(3-fluoro-benzyl)-urea 1-(3-Fluoro-benzyl)-3-(3-methylaminomethyl-[1,2,4]thiadiazol-5-yl)-urea (Intermediate XXVII) was taken up in DCM and methanol with 3,5-Dimethyl-isoxazole-4-carbaldehyde (2 eq.) and acetic acid (several drops). Reaction was stirred for several hours at ambient temperature. Sodium cyanoborohydride (2 eq.) was added at once and the reaction was stirred overnight at ambient temperature. An additional equivalent of 3,5-Dimethyl-isoxazole-4-carbaldehyde and sodium cyanoborohydride (2 eq.) was added and stirred 4 more hours. Crude rxn mixture was loaded directly onto a silica plug and eluted with 10% saturated NH$_3$/MeOH in DCM. Purified by column chromatography (silica, DCM, 0-10% MeOH saturated with NH$_3$) to give the title compound. $^1$H NMR (400 MHz, DMSO): δ 11.45 (br s, 1H), 7.43-7.35 (m, 2H), 7.17-7.05 (m, 3H), 4.38 (d, 2H), 3.58 (s, 2H), 3.33 (s, 2H), 2.31 (s, 3H), 2.16 (s, 3H), 2.15 (s, 3H).

Example 171

1-(3-fluorobenzyl)-3-(3-((2-(methylsulfonyl)ethoxy)methyl)-1,2,4-thiadiazol-5-yl)urea Step 1: Sodium hydride (4 eq, 4 mmol, 0.19 g of a 50 wt-% oil) was suspended in THF (3 mL) and cooled to 0° C. 2-(methylthio)ethanol (3 eq, 3 mmol, 0.27 g) and 15-crown-5-ether (1 drop) were added and the mixture was stirred for 30 min. 1-(3-Fluorobenzyl)-3-(3-(chloromethyl)-1,2,4-thiadiazol-5-yl)urea (Intermediate XXV) (1.0 mmol, 0.3 g) was added and the mixture was stirred over night with temperature allowed to rise to ambient temperature. Ethanol (2 mL) was added and the mixture was concentrated in vacuo.

Step 2: The crude material from step 1 was dissolved in chloroform (6 mL), cooled to 0° C. and 3-chloro perbenzoic acid (3.2 eq, 3.2 mmol, 0.55 g) was added. After stirring for 3 h LC-MS indicated the formation of the sulfone as well as the sulfoxide. Sat. aq. NaHCO$_3$ (2 mmL) was added to quench the reaction. Water (10 mL) was added and the mixture was extracted with dichloromethane (2×50 mL). Combined organic layers were dried (Na$_2$SO$_4$), filtered and concentrated in vacuo. 0.5 g of the crude product were further purified by preparative HPLC to give 0.044 g of the title compound. Also isolated was 0.065 g of the sulfoxide shown in the following example. $^1$H-NMR (300 MHz, CD$_3$OD): δ 7.33 (m, 1H), 7.14 (d, 1H), 7.06 (d, 1H), 6.97 (m, 1H), 4.57 (s, 2H), 4.45 (s, 2H), 3.96 (t, 2H), 3.36 (t, 2H), 3.04 (s, 3H).

Example 172

1-(3-fluorobenzyl)-3-(3-((2-(methylsulfinyl)ethoxy)methyl)-1,2,4-thiadiazol-5-yl)urea See Step 2 of Example 171 for details of synthesis $^1$H-NMR (300 MHz, CD$_3$OD): δ 7.33 (m, 1H), 7.14 (d, 1H), 7.06 (d, 1H), 6.96 (m, 1H), 4.57 (s, 2H), 4.46 (s, 2H), 3.99-3.92 (m, 2H), 3.19-3.10 (m, 1H), 3.02-2.99 (m, 1H), 2.68 (s, 3H).

Example 173

1-(5-Bromo-4-((2-methoxyethoxy)methyl)thiazol-2-yl)-3-(3,4-dichlorobenzyl)urea

Bromine (120 μL, 0.12 mmol, lM in CH$_2$Cl$_2$) was added dropwise to a CH$_2$Cl$_2$ (5 mL) solution of 1-(3,4-dichlorobenzyl)-3-(4-((2-methoxyethoxy)methyl)thiazol-2-yl)urea (39 mg, 0.1 mmol). The bromination was instantaneous. The mixture was washed with dilute Na$_2$SO$_3$ solution, dried and evaporated to afford the title compound. $^1$H NMR (400 MHz, CDCl$_3$): δ 11.38 (1H, br), 7.70 (1H, br), 7.45 (d, 1H), 7.39 (d, 1H), 7.19 (dd, 1H), 4.50 (s, 2H), 4.39 (d, 2H), 3.53 (m, 2H), 3.38 (m, 2H), 3.20 (s, 3H). MS (ES+): M/Z 470 (M+H)$^+$.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A compound of the Formula (I):

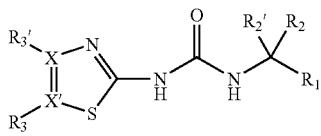

in which:

R$_1$ is selected from the group consisting of substituted aryl, unsubstituted aryl, substituted arylalkyl, unsubstituted arylalkyl, substituted heteroaryl and unsubstituted heteroaryl;

X and X' are independently selected from the group consisting of a C and N atom;

Y is selected from the group consisting of a O, S and N atom;

R$_2$ and R$_{2'}$ are independently selected from the group consisting of H, substituted linear, cyclic, or branched alkyl, unsubstituted linear, cyclic or branched alkyl, and perfluoroalkyl;

R$_3$ and R$_{3'}$ are independently selected from the group consisting of null, H, halogen, and

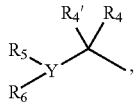

wherein one of R$_3$ or R$_{3'}$, but not both, is

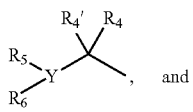

wherein R$_3$ or R$_{3'}$ is null when X or X', respectively, is N;

R$_4$ and R$_{4'}$ are independently selected from the group consisting of H, substituted linear, cyclic, or branched alkyl, unsubstituted linear, cyclic, or branched alkyl, perfluoroalkyl; and wherein when Y is O or S, R$_6$ is null, R$_5$ is selected from the group consisting of null, H, O, OH, substituted O-alkyl, unsubstituted O-alkyl, substituted aryl, unsubstituted aryl, substituted arylalkyl, unsubstituted arylalkyl, substituted linear, cyclic, or branched alkyl, unsubstituted linear, cyclic or branched alkyl, and perfluoroalkyl;

wherein when Y is N, R$_5$ is selected from the group consisting of null, H, O, OH, substituted O-alkyl, unsubstituted O-alkyl, substituted aryl, unsubstituted aryl, substituted arylalkyl, unsubstituted arylalkyl, substituted linear, cyclic, or branched alkyl, unsubstituted linear, cyclic or branched alkyl, and perfluoroalkyl, R$_6$ is selected from the group consisting of null, O, OH, substituted O-alkyl, unsubstituted O-alkyl, substituted aryl, unsubstituted aryl, substituted arylalkyl, unsubstituted arylalkyl, substituted linear, cyclic, or branched alkyl, unsubstituted linear, cyclic or branched alkyl, and perfluoroalkyl, R$_5$ and R$_6$ together can form a 4, 5, or 6 member saturated ring comprising carbon atoms or comprising at least one carbon atom and one or more heteroatoms selected from O and NR$_7$, wherein R$_7$ is selected from the group consisting of substituted or unsubstituted C$_{(1-6)}$alkyl, substituted or unsubstituted C$_{(1-6)}$acyl, substituted or unsubstituted aryl, substituted or unsubstituted heteroaryl, and wherein R$_5$, R$_6$, and NR$_7$ together can form a 4,4-, 4,5-, 5,5-, 5,6-, or 6,6-saturated bicyclic ring system comprising carbon atoms or comprising at least one carbon atom and one or more heteroatoms selected from O and N.

2. The compound of claim 1, wherein R$_1$ consists of a substituted phenyl group having one or more substituents independently selected from: halogen, cyano, (C1-6)alkyl, mono to perfluoro(C1-3)alkyl, (C3-7)cyclo alkyl, (C2-6)alkenyl, (C1-6)alkoxy, (C2-6)alkenoxy, hydroxy, amino, mono- or di-(C1-6)alkylamino, acylamino, nitro, carboxy, (C1-6) alkoxycarbonyl, (C1-6)alkenyloxycarbonyl, (C1-6)alkoxycarbonyl(C1-6)alkyl, carboxy(C1-6)alkyl, (C1-6)alkylcarbonyloxy, carboxy(C1-6)alkyloxy, (C1-6)alkoxycarbonyl (C1-6)alkoxy, (C1-6)alkylthio, (C1-6)alkylsulphinyl, (C1-6) alkylsulphonyl, sulphamoyl, mono- and di-(C1-6)- alkylsulphamoyl, and carbamoyl.

3. The compound of claim 1, wherein R$_1$ is a substituted phenyl or thiophene group selected from the group consisting of 3-fluorophenyl, 4-fluorophenyl, 3-chlorophenyl, 4-chlorophenyl, 3-bromophenyl, 4-bromophenyl, 3-iodophenyl, 4-iodophenyl, 3-methoxyphenyl, 4-methoxyphenyl, 3-methylphenyl, 4-methylphenyl, 3-trifluoromethylphenyl, 4-trifluoromethylphenyl, 3,4-methylendioxyphenyl, 3,4-difluorophenyl, 3,4-dichlorophenyl, 3,4-dibromophenyl, 3,4-dimethylphenyl, 3,4-(-CH₂CH₂CH₂-)phenyl, 3,4-(-OCH₂CH₂O-)phenyl, 3-chloro-4-fluorophenyl, benzo[1,3]dioxyl-5-yl, 3-cyanophenyl, thiophen-2-yl, thiophen-3-yl, 4,5-di-bromo-thiophen-2-yl, 5-chloro-thiophen-2-yl, and 5-bromo-thiophen-2-yl.

4. The compound of claim 1, wherein X and X' are selected from the group consisting of where X and X' are both C forming a thiazole, where X is N and X' is C forming a 3,4-thiadiazole, and where X is C and X' is N forming a 3,5-thiadiazole ring.

5. The compound of claim 1, wherein $R_2$ and $R_{2'}$ are independently selected from the group consisting of H and $C_{(1-6)}$ alkyl.

6. The compound of claim 1, wherein Y is selected from the group consisting of where Y is O forming an ether, where Y is S forming a thioether, and where Y is N forming an amine.

7. The compound of claim 1, wherein $R_{3'}$ is

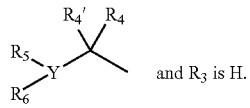 and $R_3$ is H.

8. The compound of claim 7, wherein $R_4$ and $R_{4'}$ are independently selected from the group consisting of H, substituted linear, cyclic or branched alkyl, unsubstituted linear, cyclic or branched alkyl, and perfluoroalkyl.

9. The compound of claim 7, wherein $R_5$ is selected from the group consisting of hydrogen, methyl, ethyl, hydroxyl, methoxy, carboxymethyl, hydroxymethyl, 2-methoxyethyl, butyl, phenoxyethyl, 3-methoxypropyl, 2-ethoxyethyl, 2-(dimethylamino)-ethyl, methylthioethyl, 2-(methylsulfone)ethyl, 2-(methylsulfoxyl)ethyl, 2-tert-butoxy-ethyl, 2-hydroxyethyl, phenyl, 2-(tert-butyl carbamate)-ethyl, 2-aminoethyl, 2-(morpholin-4-yl)-ethyl, 2-(acetamide)-ethyl, 2-(2-methoxyethoxy)ethyl, 2-(4-methyl-piperazin-1-yl)-ethyl, 2-(imidazol-1-yl)-ethyl, 2-(2-(2-methoxyethoxy)ethoxy)ethyl, 2-(1-methyl-1H-imidazol-2-ylsulfanyl)-ethyl, 2-(4-methyl-thiazol-5-yl)-ethyl, allyl, 2,3-dihydroxypropyl, 3-pyridin-2-yl-propyl, 2-pyridin-3-yl-ethyl, octahydroquinolizin-1-ylmethyl, 2-pyrrolidin-1-yl-ethyl, 1-methyl-piperidin-4-yl, 2-(2-oxooxazolidin-3-yl)ethyl, 2-(methylsulfonamido)ethyl, 3-methylcarboxylate-pyrazin-2-yl, 4-formyl-piperazin-1-ylmethyl, 3-methylpyrazin-2-yl, ethylphosphoramidic acid diethyl ester, 2-(carbamic acid methyl ester)ethyl, 2-(3-ethyl-ureido)-ethyl, acetic acid tert-butyl ester, acetic acid, 2-diethylamino-ethyl, 3-dimethylaminopropyl, 1,1-dioxo-tetrahydro-1-lambda⁶-thiophen-3-yl, 4-hydroxy-1,1-dioxo-tetrahydro-1-lambda⁶-thiophen-3-yl, N-(1,1-dioxo-tetrahydro-1-lambda⁶-thiophen-3-yl)-acetamide-, o-tolyl, pyridin-2-yl, 3,5-dimethylisoxazol-4-yl-methyl, 2,4-dimethoxy-benzyl, 3-(hydroxymethyl)-5-methyl-isoxazol-4-yl)methyl, 2,3,4-trimethoxy-benzyl, 4-methoxyphenyl, 4-Fluoro-phenyl, 4-acetamido-phenyl, 3,4-dimethoxy-phenyl, 2-(pyrazin-2-yl)ethyl, 4-methyl-4H-1,2,4-triazol-3-yl, 1,3,4-thiadiazol-2-yl, thiazol-2-yl, and 1-methyl-1H-tetrazol-5-yl, 4,5-dimethyl-4H-1,2,4-triazol-3-yl.

10. The compound of claim 7, wherein $R_5$ and $R_6$ together form a heterocycyl with a heteroatom selected from the group consisting of O and $NR_7$, wherein the heterocycyl is selected from the group consisting of 4-formyl-piperazin-1-yl, 4-methylpiperazin-1-yl, 4-ethylpiperazin-1-yl, 4-phenylpiperazin-1-yl, 4-pyrimidin-2-yl-piperazin-1-yl, 4-hexahydro-pyrrolo[1,2-a]imidazol-1-yl, morpholin-4-yl, 4-hydroxy-isoxazolidin-2-yl, and 1,1-dioxo-1-lamda⁶-thiomorpholin-4-yl.

11. The compound of claim 10, wherein $R_5$, $R_6$, and $R_7$ together form 4-hexahydro-pyrrolo[1,2-a]imidazol-1-yl.

12. A compound of Formula (Ia):

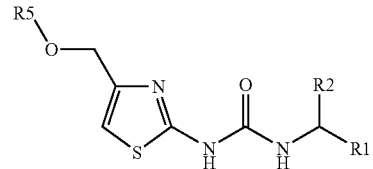

in which:

$R_5$ is selected from the group consisting of Me-, MeO(CH₂)₂—, CH₃(CH₂)₃—, PhO(CH₂)₂—, MeO(CH₂)₃—, EtO(CH₂)₂—, (CH₃)₂N(CH₂)₂—, CH₃S(CH₂)₂—, CH₃S(O)₂(CH₂)₂—, (CH₃)₃CO(CH₂)₂—, HO(CH₂)₂—, AcNH(CH₂)₂, BocNH(CH₂)₂, H₂N(CH₂)₂, Ph-, MeO(CH₂)₂O(CH₂)₂—, 4-Me-piperazin-1yl-(CH₂)₂—, 2-imidazol-1-yl-(CH₂)₂—, MeO(CH₂)₂O(CH₂)₂O(CH₂)₂—, (1-Me-1H-imidazol-2-yl)-S(CH₂)₂—, (4-Me-thiazol-5-yl)-(CH₂)₂—, Allyl-, HOCH₂CH(OH)CH₂—, (Pyridine-2-yl)-(CH₂)₃—, (Pyridine-3-yl)-(CH₂)₂—, (Octahydro-quinolizine-1-yl)CH₂—, (Pyrrolidin-1-yl)-(CH₂)₂—, 1-Me-piperidin-4-yl, 2-oxooxazolidin-3-yl, (methylsulfonamido)-(CH₂)₂—, 3-methylcarboxylate-pyrazin-2-yl, 3-Me-pyrazin-2-yl, CH₃S(O)₂NH(CH₂)₂—, (CH₃CH₂O)₂P(O)₂NH(CH₂)₂—, CH₃OC(O)NH(CH₂)₂—, CH₃CH₂NHC(O)NH(CH₂)₂— and Morpholin-4-yl-(CH₂)₂; and wherein $R_2$ is selected from the group consisting of H and CH₃; and wherein $R_1$ is selected from the group consisting of 3-fluorophenyl, 4-fluorophenyl, 3-chlorophenyl, 4-chlorophenyl, 3-bromophenyl, 4-bromophenyl, 3-iodophenyl, 4-iodophenyl, 3-methoxyphenyl, 4-methoxyphenyl, 3-methylphenyl, 4-methylphenyl, 3-trifluoromethylphenyl, 4-trifluoromethylphenyl, 3,4-methylendioxyphenyl, 3,4-difluorophenyl, 3,4-dichlorophenyl, 3,4-dibromophenyl, 3,4-dimethylphenyl, 3,4-(-CH₂CH₂CH₂-)phenyl, 3,4-(-OCH₂CH₂O-)phenyl, 3-chloro-4-fluorophenyl, benzo[1,3]dioxyl-5-yl, 3-cyanophenyl, thiophen-2-yl, thiophen-3-yl, 4,5-di-bromo-thiophen-2-yl, 5-chloro-thiophen-2-yl, and 5-bromo-thiophen-2-yl.

13. A compound of Formula (Ib):

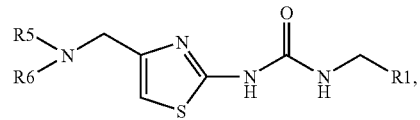

in which:

$R_5$ is selected from the group consisting of MeO(CH₂)₂, t-BuOC(O)NHCH₂CH₂, NH₂CH₂CH₂, MeOCH₂CH₂, (CH₃)₃COC(O)CH₂, HOC(O)CH₂, CH₃—, (CH₃CH₂)₂NCH₂CH₂—, (CH₃)₂NCH₂(CH₂)₂—, 1,1-dioxo-tetrahydro-1-lambda⁶-thiophen-3-yl, 4-hydroxy-1,1-dioxo-tetrahydro-1-lambda⁶-thiophen-3-yl, HOCH₂CH(OH)CH₂—, N-(1,1-dioxo-tetrahydro-1lambda⁶-thiophen-3-yl)-acetamide, o-tolyl-, pyridin-2-yl, (3,5-dimethylisoxazol-4-yl)-CH₂—, 2,4-dimethoxy-benzyl, 3-(hydroxymethyl)-5-methylisoxazol-4-yl)-CH₂—, 2,3,4-trimethoxy-benzyl-, 2,4-dimethoxy-benzyl, HO(CH₂)₂—, 3-Me-pyrazin-2-yl and (CH₃)₂NCH₂CH₂;

wherein R₆ is selected from the group consisting of CH₃, MeOCH₂CH₂, H, and CH₂CH₃; and wherein R₁ is selected from the group consisting of 3-fluorophenyl, 4-fluorophenyl, 3-chlorophenyl, 4-chlorophenyl, 3-bromophenyl, 4-bromophenyl, 3-iodophenyl, 4-iodophenyl, 3-methoxyphenyl, 4-methoxyphenyl, 3-methylphenyl, 4-methylphenyl, 3-trifluoromethylphenyl, 4-trifluoromethylphenyl, 3,4-methylendioxyphenyl, 3,4-difluorophenyl, 3,4-dichlorophenyl, 3,4-dibromophenyl, 3,4-dimethylphenyl, 3,4-(-CH₂CH₂CH₂-)phenyl, 3,4-(-OCH₂CH₂O-)phenyl, 3-chloro-4-fluorophenyl, benzo[1,3]dioxyl-5-yl, 3-cyanophenyl, thiophen-2-yl, thiophen-3-yl, 4,5-di-bromo-thiophen-2-yl, 5-chloro-thiophen-2-yl, and 5-bromo-thiophen-2-yl.

14. A compound of Formula (Ic):

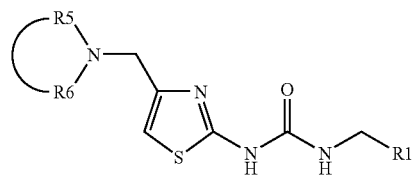

in which:

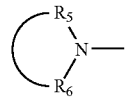

is selected from the group consisting of 4-formyl-piperazin-1-yl, 4-methylpiperazin-1-yl-, 4-ethylpiperazin-1-yl-, 4-phenylpiperazin-1-yl-, 4-pyrimidin-2-yl-piperazin-1-yl, hexahydro-pyrrolo[1,2-a]imidazole-1-yl, morpholin-4-yl, 4-hydroxyisoxazolidin-2-yl, and 1,1-dioxo-1-lambda⁶-thiomorpholin-4-yl and wherein R1 is selected from the group consisting of 3-fluorophenyl, 4-fluorophenyl, 3-chlorophenyl, 4-chlorophenyl, 3-bromophenyl, 4-bromophenyl, 3-iodophenyl, 4-iodophenyl, 3-methoxyphenyl, 4-methoxyphenyl, 3-methylphenyl, 4-methylphenyl, 3-trifluoromethylphenyl, 4-trifluoromethylphenyl, 3,4-methylendioxyphenyl, 3,4-difluorophenyl, 3,4-dichlorophenyl, 3,4-dibromophenyl, 3,4-dimethylphenyl, 3,4-(-CH₂CH₂CH₂-)phenyl, 3,4-(-OCH₂CH₂O-)phenyl, 3-chloro-4-fluorophenyl, benzo[1,3]dioxyl-5-yl, 3-cyanophenyl, thiophen-2-yl, thiophen-3-yl, 4,5-di-bromo-thiophen-2-yl, 5-chloro-thiophen-2-yl, and 5-bromo-thiophen-2-yl.

15. A compound of Formula (Id):

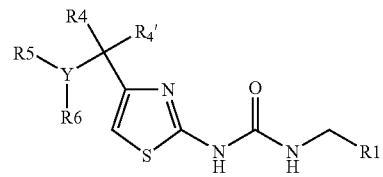

in which:

R₄ and R₄' are independently selected from the group consisting of H, O, and null;

wherein Y is selected from the group consisting of N and O; and wherein R₅ and R₆ are independently selected from the group consisting of O, OEt, OH, H, Et, CH₃, MeO(CH₂)₂—, and null; and wherein R₁ is selected from the group consisting of 3-fluorophenyl, 4-fluorophenyl, 3-chlorophenyl, 4-chlorophenyl, 3-bromophenyl, 4-bromophenyl, 3-iodophenyl, 4-iodophenyl, 3-methoxyphenyl, 4-methoxyphenyl, 3-methylphenyl, 4-methylphenyl, 3-trifluoromethylphenyl, 4-trifluoromethylphenyl, 3,4-methylendioxyphenyl, 3,4-difluorophenyl, 3,4-dichlorophenyl, 3,4-dibromophenyl, 3,4-dimethylphenyl, 3,4-(-CH₂CH₂CH₂-)phenyl, 3,4-(-OCH₂CH₂O-)phenyl, 3-chloro-4-fluorophenyl, benzo[1,3]dioxyl-5-yl, 3-cyanophenyl, thiophen-2-yl, thiophen-3-yl, 4,5-di-bromo-thiophen-2-yl, 5-chloro-thiophen-2-yl, and 5-bromo-thiophen-2-yl.

16. A compound of Formula (Ie):

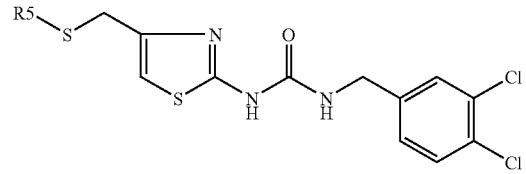

in which:

R₅ is selected from the group consisting of 4-MeO-Ph, 4-F-Ph, 4-acetamido-Ph, 3,4-dimethoxy-Ph, (Pyrazin-2-yl)-(CH₂)₂—, 4-methyl-4H-1,2,4-triazol-3-yl, 1,3,4-thiadiazol-2-yl, thiazol-2-yl, 1-methyl-1H-tetrazol-5-yl, and 4,5-dimethyl-4H-1,2,4-triazol-3-yl.

17. A compound of Formula (If):

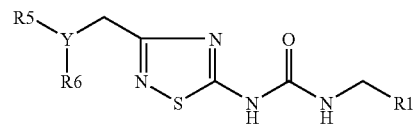

in which:

Y is selected from the group consisting of N and O; and wherein R₅ is selected from the group consisting of MeO(CH₂)₂—, 1,1-dioxo-tetrahydro-1-lambda⁶-thiophen-3-yl, 3,5-Dimethyl-isoxazol-4-ylmethyl-, CH₃S(O)₂(CH₂)₂—, and CH₃S(O)(CH₂)₂—; and wherein R₆ is selected from the group consisting of H, CH₃, and null when Y is O; and wherein R₁ is selected from the group consisting of 3-fluorophenyl, 4-fluorophenyl, 3-chlorophenyl, 4-chlorophenyl, 3-bromophenyl, 4-bromophenyl, 3-iodophenyl, 4-iodophenyl, 3-methoxyphenyl, 4-methoxyphenyl, 3-methylphenyl, 4-methylphenyl, 3-trifluoromethylphenyl, 4-trifluoromethylphenyl, 3,4-methylendioxyphenyl, 3,4-difluorophenyl, 3,4-dichlorophenyl, 3,4-dibromophenyl, 3,4-dimethylphenyl, 3,4-(-CH₂CH₂CH₂-)phenyl, 3,4-(-OCH₂CH₂O-)phenyl, 3-chloro-4-fluorophenyl, benzo[1,3]dioxyl-5-yl, 3-cyanophenyl, thiophen-2-yl, thiophen-3-yl, 4,5-di-bromo-thiophen-2-yl, 5-chloro-thiophen-2-yl, and 5-bromo-thiophen-2-yl.

18. A compound selected from the group consisting of:

1-(3,4-dichlorobenzyl)-3-(4-(methoxymethyl)thiazol-2-yl)urea;
1-(3,4-dichlorobenzyl)-3-(4-((2-methoxyethoxy)methyl)thiazol-2-yl)urea;
1-(3,4-dichlorobenzyl)-3-(4-(butoxymethyl)thiazol-2-yl)urea;
1-(3,4-dichlorobenzyl)-3-(4-((2-phenoxyethoxy)methyl)thiazol-2-yl)urea;
1-(3,4-dichlorobenzyl)-3-(4-((3-methoxypropoxy)methyl)thiazol-2-yl)urea;
1-(3,4-dichlorobenzyl)-3-(4-((2-ethoxyethoxy)methyl)thiazol-2-yl)urea;
1-(3,4-dichlorobenzyl)-3-(4-((2-(dimethylamino)ethoxy)methyl)thiazol-2-yl)urea;
1-(3,4-dichlorobenzyl)-3-(4-((2-(methylthio)ethoxy)methyl)thiazol-2-yl)urea;
1-(3,4-dichloro-benzyl)-3-[4-(2-methanesulfinyl-ethoxymethyl)-thiazol-2-yl]-urea;
1-(3,4-dichlorobenzyl)-3-(4-((2-(methylsulfonyl)ethoxy)methyl)thiazol-2-yl)urea;
1-(3-fluoro-benzyl)-3-[4-(2-methoxy-ethoxymethyl)-thiazol-2-yl]-urea;
1-[4-(2-tert-butoxy-ethoxymethyl)-thiazol-2-yl]-3-(3,4-dichloro-benzyl)-urea;
1-(3,4-dichloro-benzyl)-3-[4-(2-hydroxy-ethoxymethyl)-thiazol-2-yl]-urea;
1-(3,4-dichloro-benzyl)-3-(4-phenoxymethyl-thiazol-2-yl)-urea;
1-(3-fluoro-benzyl)-3-[4-(2-methanesulfonyl-ethoxymethyl)-thiazol-2-yl]-urea;
5-{2-[3-(3,4-dichloro-benzyl)-ureido]-thiazol-4-yl}-pyrrolidin-3-yl ester-urea;
Ethyl 2-(2-(3-(3,4-dichlorobenzyl)ureido)thiazol-4-yl)acetate-urea;
1-(3,4-dichlorobenzyl)-3-(4-(2-hydroxyethyl)thiazol-2-yl)urea;
1-(3-fluorobenzyl)-3-(4-(2-hydroxyethyl)thiazol-2-yl)urea;
Ethyl 2-(3-(3,4-dichlorobenzyl)ureido)thiazole-4-carboxylate-urea;
1-(3,4-dichlorobenzyl)-3-(4-(hydroxymethyl)thiazol-2-yl)urea;
1-(3-bromo-benzyl)-3-(4-{[(2-methoxy-ethyl)-methyl-amino]-methyl}-thiazol-2-yl)-urea;
1-(3-chloro-benzyl)-3-(4-{[(2-methoxy-ethyl)-methyl-amino]-methyl}-thiazol-2-yl)-urea;
1-(3-fluoro-benzyl)-3-(4-{[(2-methoxy-ethyl)-methyl-amino]-methyl}-thiazol-2-yl)-urea;
1-(3-chloro-4-fluoro-benzyl)-3-(4-{[(2-methoxy-ethyl)-methyl-amino]-methyl}-thiazol-2-yl)-urea;
1-(3,4-dimethyl-benzyl)-3-[4-(2-methoxy-ethoxymethyl)-thiazol-2-yl]-urea;
1-(3-bromo-benzyl)-3-[4-(2-methoxy-ethoxymethyl)-thiazol-2-yl]-urea;
1-(4-chloro-3-trifluoromethyl-benzyl)-3-[4-(2-methoxy-ethoxymethyl)-thiazol-2-yl]-urea;
1-benzo[1,3]dioxol-5-ylmethyl-3-[4-(2-methoxy-ethoxymethyl)-thiazol-2-yl]-urea;
1-(3-chloro-4-fluoro-benzyl)-3-[4-(2-methoxy-ethoxymethyl)-thiazol-2-yl]-urea;
1-(3-chloro-benzyl)-3-[4-(2-methoxy-ethoxymethyl)-thiazol-2-yl]-urea;
1-(3-iodo-benzyl)-3-[4-(2-methoxy-ethoxymethyl)-thiazol-2-yl]-urea;
1-(4-bromobenzyl)-3-(4-((2-methoxyethoxy)methyl)thiazol-2-yl)urea;
1-(1-(4-bromophenyl)ethyl)-3-(4-((2-methoxyethoxy)methyl)thiazol-2-yl)urea;
1-(4-chloro-3-fluoro-benzyl)-3-[4-(2-methoxy-ethoxymethyl)-thiazol-2-yl]-urea;
1-(3-bromo-4-chloro-benzyl)-3-[4-(2-methoxy-ethoxymethyl)-thiazol-2-yl]-urea;
1-(3,5-difluoro-benzyl)-3-[4-(2-methoxy-ethoxymethyl)-thiazol-2-yl]-urea;
1-[4-(2-methoxy-ethoxymethyl)-thiazol-2-yl]-3-(3,4,5-trifluoro-benzyl)-urea;
1-(4,5-dibromo-thiophen-2-ylmethyl)-3-[4-(2-methoxy-ethoxymethyl)-thiazol-2-yl]-urea;
1-(2,2-difluoro-benzo[1,3]dioxol-5-ylmethyl)-3-[4-(2-methoxy-ethoxymethyl)-thiazol-2-yl]-urea;
1-(3-chloro-5-fluoro-benzyl)-3-[4-(2-methoxy-ethoxymethyl)-thiazol-2-yl]-urea;
1-[4-(2-methoxy-ethoxymethyl)-thiazol-2-yl]-3-thiophen-3-ylmethyl-urea;
1-[4-(2-methoxy-ethoxymethyl)-thiazol-2-yl]-3-thiophen-2-ylmethyl-urea;
1-(5-bromo-thiophen-2-ylmethyl)-3-[4-(2-methoxy-ethoxymethyl)-thiazol-2-yl]-urea;
1-(5-chloro-thiophen-2-ylmethyl)-3-[4-(2-methoxy-ethoxymethyl)-thiazol-2-yl]-urea;
1-(4-fluoro-benzyl)-3-[4-(2-methoxy-ethoxymethyl)-thiazol-2-yl]-urea;
1-(3-chloro-benzyl)-3-[4-(2-methanesulfonyl-ethoxymethyl)-thiazol-2-yl]-urea;
1-(3-bromo-benzyl)-3-[4-(2-methanesulfonyl-ethoxymethyl)-thiazol-2-yl]-urea;
tert-butyl 2-((2-(3-(3,4-dichlorobenzyl)ureido)thiazol-4-yl)methoxy)-ethylcarbamate;
1-(3,4-dichlorobenzyl)-3-(4-((2-aminoethoxy)methyl)thiazol-2-yl)urea;
1-(3,4-dichloro-benzyl)-3-[4-(2-morpholin-4-yl-ethoxymethyl)-thiazol-2-yl]-urea;
N-(2-{2-[3-(3,4-dichloro-benzyl)-ureido]-thiazol-4-ylmethoxy}-ethyl)-acetamide;
1-(benzo[d][1,3]dioxol-5-ylmethyl)-3-(4-((2-(methylthio)ethoxy)methyl)thiazol-2-yl)urea;
1-(benzo[d][1,3]dioxol-5-ylmethyl)-3-(4-((2-(methylsulfoxyl)ethoxy)methyl)thiazol-2-yl)urea;
1-(benzo[d][1,3]dioxol-5-ylmethyl)-3-(4-((2-(methylsulfone)ethoxy)methyl)thiazol-2-yl)urea;
1-(3,4-dichlorobenzyl)-3-(4-((2-(2-methoxyethoxy)ethoxy)methyl)thiazol-2-yl)urea;
1-(3,4-dichlorobenzyl)-3-(4-((2-(4-methylpiperazin-1-yl)ethoxy)methyl)thiazol-2-yl)urea;
1-(3,4-dichlorobenzyl)-3-[4-(2-imidazol-1-yl-ethoxymethyl)-thiazol-2-yl]-urea;
1-(3,4-dichlorobenzyl)-3-(4-((2-(2-(2-methoxyethoxy)ethoxy)methyl)thiazol-2-yl)urea;

1-(3,4-dichloro-benzyl)-3-{4-[2-(1-methyl-1H-imidazol-2-ylsulfanyl)-ethoxymethyl]-thiazol-2-yl}-urea;
1-(3,4-dichloro-benzyl)-3-{4-[2-(4-methyl-thiazol-5-yl)-ethoxymethyl]-thiazol-2-yl}-urea;
1-(3,4-dichlorobenzyl)-3-(4-(allyloxymethyl)thiazol-2-yl)urea;
1-(3,4-dichlorobenzyl)-3-(4-((2,3-dihydroxypropoxy)methyl)thiazol-2-yl)urea;
1-(3,4-dichloro-benzyl)-3-[4-(3-pyridin-2-yl-propoxymethyl)-thiazol-2-yl]-urea;
1-(3,4-dichloro-benzyl)-3-[4-(2-pyridin-3-yl-ethoxymethyl)-thiazol-2-yl]-urea;
1-(3,4-dichloro-benzyl)-3-[4-(octahydro-quinolizin-1-yl-methoxymethyl)-thiazol-2-yl]-urea;
1-(3,4-dichlorobenzyl)-3-(4-((2-(pyrrolidin-1-yl)ethoxy)methyl)thiazol-2-yl)urea;
1-(3,4-dichloro-benzyl)-3-[4-(1-methyl-piperidin-4-yloxymethyl)-thiazol-2-yl]-urea;
1-(3,4-dichlorobenzyl)-3-(4-((2-(2-oxooxazolidin-3-yl)ethoxy)methyl)thiazol-2-yl)urea;
1-(3,4-dichlorobenzyl)-3-(4-((2-(methylsulfonamido)ethoxy)methyl)thiazol-2-yl)urea;
methyl 3-((2-(3-(3-fluorobenzyl)ureido)thiazol-4-yl)methoxy)pyrazine-2-carboxylate-urea;
1-(3-fluorobenzyl)-3-(4-((3-methylpyrazin-2-yloxy)methyl)thiazol-2-yl)urea;
1-(3,4-dichloro-benzyl)-3-[4-(4-formyl-piperazin-1-ylmethyl)-thiazol-2-yl]-urea;
[2-({2-[3-(3,4-dichloro-benzyl)-ureido]-thiazol-4-ylmethyl}-methyl-amino)-ethyl]-carbamic acid tert-butyl ester-urea;
1-(4-{[(2-amino-ethyl)-methyl-amino]-methyl}-thiazol-2-yl)-3-(3,4-dichloro-benzyl)-urea;
1-(3,4-dichlorobenzyl)-3-(4-((4-methylpiperazin-1-yl)methyl)thiazol-2-yl)urea;
1-(3,4-dichlorobenzyl)-3-(4-((4-ethylpiperazin-1-yl)methyl)thiazol-2-yl)urea;
1-(3,4-dichlorobenzyl)-3-(4-((4-phenylpiperazin-1-yl)methyl)thiazol-2-yl)urea;
1-(3,4-dichloro-benzyl)-3-[4-(4-pyrimidin-2-yl-piperazin-1-ylmethyl)-thiazol-2-yl]-urea;
1-(4-{[bis-(2-methoxy-ethyl)-amino]-methyl}-thiazol-2-yl)-3-(3,4-dichloro-benzyl)-urea;
({2-[3-(3,4-dichloro-benzyl)-ureido]-thiazol-4-ylmethyl}-methyl-amino)-acetic acid tert-butyl ester-urea;
({2-[3-(3,4-dichloro-benzyl)-ureido]-thiazol-4-ylmethyl}-methyl-amino)-acetic acid;
1-(3,4-dichloro-benzyl)-3-[4-(hexahydro-pyrrolo[1,2-a]imidazol-1-ylmethyl)-thiazol-2-yl]-urea;
1-(3,4-dichloro-benzyl)-3-{4-[(2-methoxy-ethylamino)-methyl]-thiazol-2-yl}-urea;
1-(3,4-dichloro-benzyl)-3-(4-{[(2-methoxy-ethyl)-methyl-amino]-methyl}-thiazol-2-yl)-urea;
1-(3,4-dichloro-benzyl)-3-(4-morpholin-4-ylmethyl-thiazol-2-yl)-urea;
1-(3,4-dichloro-benzyl)-3-(4-{[(2-dimethylamino-ethyl)-methyl-amino]-methyl}-thiazol-2-yl)-urea;
1-(3,4-dichloro-benzyl)-3-(4-{[ethyl-(2-methoxy-ethyl)-amino]-methyl}-thiazol-2-yl)-urea;
1-(3,4-dichlorobenzyl)-3-(4-((dimethylamino)methyl)thiazol-2-yl)urea;
1-(benzo[d][1,3]dioxol-5-ylmethyl)-3-(4-(((2-methoxyethyl)(methyl)amino)methyl)thiazol-2-yl)urea;
1-(benzo[d][1,3]dioxol-5-ylmethyl)-3-(4-(((2-(dimethylamino)ethyl)(methyl)amino)methyl)thiazol-2-yl)urea;
1-(3,4-dichloro-benzyl)-3-(4-{[(2-diethylamino-ethyl)-methyl-amino]-methyl}-thiazol-2-yl)-urea;
1-(3,4-dichloro-benzyl)-3-(4-{[(3-dimethylamino-propyl)-methyl-amino]-methyl}-thiazol-2-yl)-urea;
1-(3,4-dichloro-benzyl)-3-(4-{[(1,1-dioxo-tetrahydro-1-lambda$^6$-thiophen-3-yl)-methyl-amino]-methyl}-thiazol-2-yl)-urea;
1-(3,4-dichloro-benzyl)-3-(4-{[(4-hydroxy-1,1-dioxo-tetrahydro-1-lambda$^6$-thiophen-3-yl)-methyl-amino]-methyl}-thiazol-2-yl)-urea;
1-(3,4-dichloro-benzyl)-3-{4-[(4-hydroxy-1,1-dioxo-tetrahydro-1-lambda$^6$-thiophen-3-ylamino)-methyl]-thiazol-2-yl}-urea;
1-(4-{[(1,1-Dioxo-tetrahydro-1lambda$^6$-thiophen-3-yl)-methyl-amino]-methyl}-thiazol-2-yl)-3-(3-fluoro-benzyl)-urea;
1-(3,4-dichloro-benzyl)-3-(4-{[(2,3-dihydroxy-propyl)-methyl-amino]-methyl}-thiazol-2-yl)-urea;
1-(3,4-dichlorobenzyl)-3-(4-((4-hydroxyisoxazolidin-2-yl)methyl)thiazol-2-yl)urea;
1-(3,4-dichloro-benzyl)-3-[4-(1,1-dioxo-1-lambda$^6$-thiomorpholin-4-ylmethyl)-thiazol-2-yl]-urea;
2-({2-[3-(3,4-dichloro-benzyl)-ureido]-thiazol-4-ylmethyl}-methyl-amino)-N-(1,1-dioxo-tetrahydro-1lambda$^6$-thiophen-3-yl)-acetamide;
1-(3-fluoro-benzyl)-3-{4-[(methyl-o-tolyl-amino)-methyl]-thiazol-2-yl}-urea;
1-(3-fluoro-benzyl)-3-{4-[(methyl-pyridin-2-yl-amino)-methyl]-thiazol-2-yl}-urea;
1-(3,4-dichloro-benzyl)-3-(4-methylaminomethyl-thiazol-2-yl)-urea;
1-(3,4-dichlorobenzyl)-3-(4-((((3,5-dimethylisoxazol-4-yl)methyl)(methyl)amino)methyl)thiazol-2-yl)urea;
1-(3,4-dichloro-benzyl)-3-(4-{[(2,4-dimethoxy-benzyl)-methyl-amino]-methyl}-thiazol-2-yl)-urea;
1-(3-fluorobenzyl)-3-(4-((((3-(hydroxymethyl)-5-methyl-isoxazol-4-yl)methyl)(methyl)amino)methyl)thiazol-2-yl)urea;
1-(3,4-dichloro-benzyl)-3-{4-[(2,3,4-trimethoxy-benzylamino)-methyl]-thiazol-2-yl}-urea;
1-(3,4-dichloro-benzyl)-3-{4-[(2,4-dimethoxy-benzylamino)-methyl]-thiazol-2-yl}-urea;
1-(3,4-dichloro-benzyl)-3-{4-[(2-hydroxy-ethylamino)-methyl]-thiazol-2-yl}-urea;
2-(3-(3,4-dichlorobenzyl)ureido)-N-(2-methoxyethyl)-N-methylthiazole-4-carboxamide;
1-(3-fluorobenzyl)-3-(4-((methyl(3-methylpyrazin-2-yl)amino)methyl)thiazol-2-yl)urea;
1-(3,4-dichlorobenzyl)-3-(4-((2-(methylsulfonamido)ethoxy)methyl)thiazol-2-yl)urea;
Diethyl 2-((2-(3-(3,4-dichlorobenzyl)ureido)thiazol-4-yl)methoxy)ethylphosphor-amidate;
(2-{2-[3-(3,4-dichloro-benzyl)-ureido]-thiazol-4-ylmethoxy}-ethyl)-carbamic acid methyl ester;
1-(3,4-dichloro-benzyl)-3-{4-[2-(3-ethyl-ureido)-ethoxymethyl]-thiazol-2-yl}-urea;
1-(3,4-dichlorobenzyl)-3-(4-((4-methoxyphenylthio)methyl)thiazol-2-yl)urea;
1-(3,4-dichlorobenzyl)-3-(4-((4-fluorophenylthio)methyl)thiazol-2-yl)urea;
1-(3,4-dichlorobenzyl)-3-(4-((4-acetamidophenylthio)methyl)thiazol-2-yl)urea;
1-(3,4-dichlorobenzyl)-3-(4-((3,4-dimethoxyphenylthio)methyl)-thiazol-2-yl)urea;
1-(3,4-dichlorobenzyl)-3-(4-((2-(pyrazin-2-yl)ethylthio)methyl)thiazol-2-yl)urea;
1-(3,4-dichlorobenzyl)-3-(4-((4-methyl-4H-1,2,4-triazol-3-ylthio)methyl)thiazol-2-yl)urea;

1-(4-((1,3,4-thiadiazol-2-ylthio)methyl)thiazol-2-yl)-3-(3,4-dichlorobenzyl)urea;
1-(3,4-dichlorobenzyl)-3-(4-((thiazol-2-ylthio)methyl)thiazol-2-yl)urea;
1-(3,4-dichlorobenzyl)-3-(4-((1-methyl-1H-tetrazol-5-ylthio)methyl)thiazol-2-yl)urea;
1-(3,4-dichlorobenzyl)-3-(4-((4,5-dimethyl-4H-1,2,4-triazol-3-ylthio)methyl)thiazol-2-yl)urea;
1-(3,4-dichloro-benzyl)-3-(3-{[(2-methoxy-ethyl)-methyl-amino]-methyl}-[1,2,4]thiadiazol-5-yl)-urea;
1-(3-fluoro-benzyl)-3-(3-{[(2-methoxy-ethyl)-methyl-amino]-methyl}-[1,2,4]thiadiazol-5-yl)-urea;
1-(3-fluorobenzyl)-3-(3-((2-methoxyethoxy)methyl)-1,2,4-thiadiazol-5-yl)urea;
1-(3,4-dichloro-benzyl)-3-[3-(2-methoxy-ethoxymethyl)-[1,2,4]thiadiazol-5-yl]-urea;
1-(3,4-dichloro-benzyl)-3-(3-{[(1,1-dioxo-tetrahydro-1l6-thiophen-3-yl)-methyl-amino]-methyl}-[1,2,4]thiadiazol-5-yl)-urea;
1-(3-{[(1,1-dioxo-tetrahydro-1l6-thiophen-3-yl)-methyl-amino]-methyl}-[1,2,4]thiadiazol-5-yl)-3-(3-fluoro-benzyl)-urea;
1-(3-{[(3,5-dimethyl-isoxazol-4-ylmethyl)-methyl-amino]-methyl}-[1,2,4]thiadiazol-5-yl)-3-(3-fluoro-benzyl)-urea;
1-(3-fluorobenzyl)-3-(3-((2-(methylsulfonyl)ethoxy)methyl)-1,2,4-thiadiazol-5-yl)urea;
1-(3-fluorobenzyl)-3-(3-((2-(methylsulfinyl)ethoxy)methyl)-1,2,4-thiadiazol-5-yl)urea; and
1-(5-Bromo-4-((2-methoxyethoxy)methyl)thiazol-2-yl)-3-(3,4-dichlorobenzyl)urea.

19. A pharmaceutical composition comprising a therapeutically effective amount of a compound according to claim 1 or a pharmaceutically acceptable salt of a compound of claim 1.

20. A pharmaceutical composition comprising a therapeutically effective amount of a compound according to 18 or a pharmaceutically acceptable salt of a compound of claim 18.

21. A method to protect a patient from a bacterial infection which comprises administering a therapeutically effective amount of a compound of Formula (I) or a pharmaceutically acceptable salt of a compound of Formula (I) to a patient in need thereof.

22. A method to protect a patient from a bacterial infection which comprises administering a therapeutically effective amount of a compound of claim 18 or a pharmaceutically acceptable salt of a compound of claim 18 to a patient in need thereof.

23. A method of preparing the heterocyclic urea compound of claim 1, comprising:

a) providing a compound of the Formula (II):

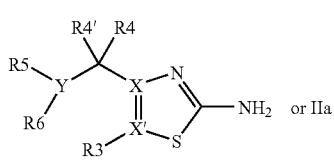

(II)

or IIa

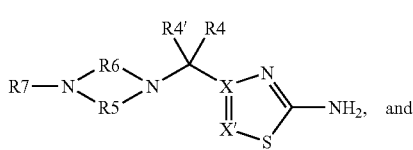

(IIa)

and b) reacting a compound of (a) with a compound of Formula (III):

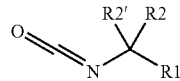

(III)

to generate a heterocyclic urea compound of the Formula (I):

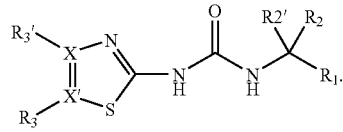

(I)

24. A method of preparing the heterocyclic urea compound of claim 1, comprising:

a) providing a phenyl carbamate compound of the Formula (IV):

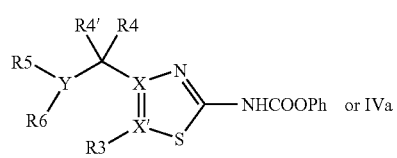

(IV)  or IVa

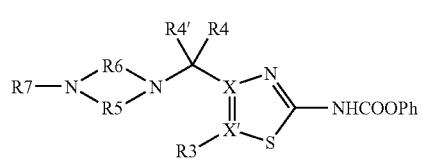

(IVa)

b) reacting a compound of (a) with compound of Formula (V):

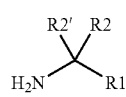

(V)

to generate a heterocyclic urea compound of the Formula (I):

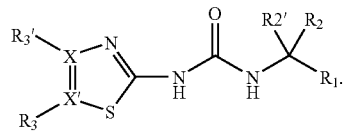

(I)

25. A method of preparing the heterocyclic urea compound of claim 1, comprising:

a) providing a chloromethyl compound of Formula (VI)

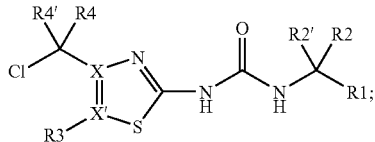
(VI)

b) reacting a compound of (a) with a compound selected from the group consisting of:

(i) an alcohol of Formula (VIIa),

(VIIa)

(ii) a mercaptan of Formula (VIIb),

(VIIb)

(iii) an amine of Formula (VIIc), and

(iv) an amine of Formula (VIId)

to generate a heterocyclic urea compound of the Formula (I):

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:

```
<223> OTHER INFORMATION: Synthetic

<400> SEQUENCE: 1
accagtgaga cgggcaaca                                                  19

<210> SEQ ID NO 2
<211> LENGTH: 33
<212> TYPE: DNA
<213> ORGANISM: Artificial Sequence
<220> FEATURE:
<223> OTHER INFORMATION: Synthetic

<400> SEQUENCE: 2
tgaattatag gccctgttgc ccgtctcact ggt                                  33
```